US009536633B2

(12) United States Patent
Higashimura et al.

(10) Patent No.: US 9,536,633 B2
(45) Date of Patent: Jan. 3, 2017

(54) METALLIC COMPOSITE AND COMPOSITION THEREOF

(75) Inventors: Hideyuki Higashimura, Tsukuba (JP);
Takayuki Iijima, Tsukuba (JP);
Masahiro Fujioka, Wakayama (JP);
Kenta Tanaka, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 1249 days.

(21) Appl. No.: 13/263,220

(22) PCT Filed: Apr. 6, 2010

(86) PCT No.: PCT/JP2010/056493
§ 371 (c)(1),
(2), (4) Date: Oct. 6, 2011

(87) PCT Pub. No.: WO2010/117075
PCT Pub. Date: Oct. 14, 2010

(65) Prior Publication Data
US 2012/0032121 A1    Feb. 9, 2012

(30) Foreign Application Priority Data

Apr. 10, 2009 (JP) ................. 2009-095657

(51) Int. Cl.
| H01B 1/00 | (2006.01) |
| B32B 9/04 | (2006.01) |
| B32B 9/00 | (2006.01) |
| H01B 1/12 | (2006.01) |
| B22F 1/00 | (2006.01) |
| B82Y 30/00 | (2011.01) |
| C07F 5/02 | (2006.01) |
| C09D 5/24 | (2006.01) |
| H01L 51/00 | (2006.01) |
| C08G 61/02 | (2006.01) |
| C08K 3/08 | (2006.01) |
| C08L 65/00 | (2006.01) |

(52) U.S. Cl.
CPC ............ H01B 1/128 (2013.01); B22F 1/0025 (2013.01); B22F 1/0062 (2013.01); B82Y 30/00 (2013.01); C07F 5/025 (2013.01); C08G 61/02 (2013.01); C08K 3/08 (2013.01); C09D 5/24 (2013.01); H01L 51/009 (2013.01); H01L 51/0039 (2013.01); H01L 51/0043 (2013.01); B22F 2999/00 (2013.01); C08G 2261/143 (2013.01); C08G 2261/145 (2013.01); C08G 2261/149 (2013.01); C08G 2261/1424 (2013.01); C08G 2261/1426 (2013.01); C08G 2261/3142 (2013.01); C08G 2261/411 (2013.01); C08G 2261/51 (2013.01); C08G 2261/95 (2013.01); C08G 2261/964 (2013.01); C08K 2201/016 (2013.01); C08L 65/00 (2013.01); Y02E 10/549 (2013.01); Y02P 70/521 (2015.11)

(58) Field of Classification Search
USPC ............. 428/411.1, 403, 328, 690; 252/500
See application file for complete search history.

(56) References Cited

U.S. PATENT DOCUMENTS

| 5,215,820 | A  | * | 6/1993  | Hosokawa et al. ........... 428/403 |
| 6,391,481 | B1 |   | 5/2002  | Jonas et al. |
| 2003/0153141 | A1 |   | 8/2003  | Carter et al. |
| 2005/0175861 | A1 |   | 8/2005  | Elschner et al. |
| 2008/0020208 | A1 | * | 1/2008  | Lee et al. .................... 428/411.1 |
| 2008/0143906 | A1 |   | 6/2008  | Allemand et al. |
| 2009/0247685 | A1 | * | 10/2009 | De La Vega et al. ........ 524/440 |

FOREIGN PATENT DOCUMENTS

| CN | 101085857 A | 12/2007 |
| GB | 2300196 A | 10/1996 |
| JP | 04-202707 A | 7/1992 |
| JP | 2000-91081 A | 3/2000 |
| JP | 2002-266007 A | 9/2002 |
| JP | 2004-149871 A | 5/2004 |
| JP | 200579064 A | 3/2005 |
| JP | 2005514729 A | 5/2005 |
| JP | 2005-232452 A | 9/2005 |
| JP | 2005-317394 A | 11/2005 |
| JP | 2006-77229 A | 3/2006 |
| JP | 200673273 A | 3/2006 |
| JP | 2006-233252 A | 9/2006 |
| JP | 2007-327058 A | 12/2007 |
| JP | 200856910 A | 3/2008 |

(Continued)

OTHER PUBLICATIONS

First Office Action issued Mar. 5, 2013 in Chinese Patent Application No. 201080016099.4 to Sumitomo Chemical Co., Ltd., with translation.
Extended European Search Report issued Apr. 25, 2014 in corresponding European Patent Application No. 10761774.8.
Second Office Action issued Oct. 28, 2013 in Chinese Patent Application No. 201080016099.4 with English translation.
Jung-Yong Lee et al., "Solution-Processed Metal Nanowire Mesh Transparent Electrodes", Nano Letters, vol. 8, No. 2, 2008, pp. 689-692.
Yugang Sun et al., "Uniform Silver Nanowires Synthesis by Reducing AgNO3 with Ethylene Glycol in the Presence of Seeds and Poly(Vinyl Pyrrolidone)", Chem. Mater., vol. 14, 2002, pp. 4736-4745.

(Continued)

*Primary Examiner* — Monique Peets
(74) *Attorney, Agent, or Firm* — Sughrue Mion, PLLC

(57) ABSTRACT

A metallic composite in which a conjugated compound having a molecular weight of 200 or more is adsorbed to a metallic nanostructure having an aspect ratio of 1.5 or more, for example, a metallic composite in which a compound having a group represented by the formula (I) or a repeating unit represented by the formula (II) or both of them is adsorbed to a metallic nanostructure having an aspect ratio of 1.5 or more, is useful for electronic devices such as a light-emitting device, a solar cell and an organic transistor.

25 Claims, 4 Drawing Sheets

(56) References Cited

FOREIGN PATENT DOCUMENTS

| | | | |
|---|---|---|---|
| JP | 2008-097949 A | | 4/2008 |
| JP | 2008-515654 | | 5/2008 |
| JP | 2009-070660 | * | 4/2009 |
| JP | 2009-205924 A | | 9/2009 |
| JP | 2010525526 A | | 7/2010 |
| JP | 2011-34711 | | 2/2011 |
| WO | 2004/029176 A1 | | 4/2004 |
| WO | 2006/124055 A2 | | 11/2006 |
| WO | 2007/002737 A2 | | 1/2007 |
| WO | 2008/131304 A1 | | 10/2008 |
| WO | 2011/013618 A1 | | 2/2011 |

OTHER PUBLICATIONS

Yugang Sun et al., "Polyol Synthesis of Uniform Silver Nanowires: A Plausible Growth Mechanism and the Supporting Evidence", Nano Letters, vol. 3, No. 7, 2003, pp. 955-960.

Kylee E. Korte et al., "Rapid synthesis of silver nanowires through a CuCl- or CuCl2-mediated polyol process", J. Mater. Chem., vol. 18, 2008, pp. 437-441.

Robert D. Miller, "Polysilane High Polymers", Chem. Rev. vol. 89, 1989, pp. 1359-1410.

Ken-Tsung Wong et al., "4,5-Diazafluorene-Incorported Ter(9,9-diarylfluorene): A Novel molecular Doping Strategy for Improving the Electron Injection Property of a Highly Efficient OLED Blue Emitter", Organic Letters, vol. 7, No. 10, 2005, pp. 1979-1982.

Piers Andrew and Adelina Ilie, "Functionalised Silver Nanowire Structures", Journal of Physics: Conference Series 61, 2007, pp. 36-40.

Communication from the Japanese Patent Office dated Oct. 27, 2015 in counterpart application No. 2014-261996.

Communication dated May 31, 2016 from the Japanese Patent Office issued in corresponding Application No. 2014-261996.

* cited by examiner

METALLIC COMPOSITE AND COMPOSITION THEREOF

CROSS REFERENCE TO RELATED APPLICATIONS

This application is a National Stage of International Application No. PCT/JP2010/056493 filed Apr. 6, 2010, claiming priority based on Japanese Patent Application No. 2009-095657 filed Apr. 10, 2009, the contents of all of which are incorporated herein by reference in their entirety.

TECHNICAL FIELD

The present invention relates to a metallic composite and a composition thereof.

BACKGROUND ART

A material containing a metal and an organic compound is attracting attention in recent years since the material is useful for an electrode material of an electronic device. The material containing a metal and an organic compound include a metallic composite in which a metal and an organic compound are complexed with each other and a composition in which a metallic composite and an organic compound are mixed. Specifically, it is disclosed in "Nano letters, vol. 2, pp. 689-692 (2008)" to prepare an electrode by an application method using a dispersion liquid in which a silver nanowire having polyvinyl pyrrolidone adsorbed thereto, as the metallic composite, is dispersed in a polar solvent such as water and methanol.

DISCLOSURE OF THE INVENTION

However, depending on the type of a layer other than an electrode or a substrate that constitutes an electronic device, a non-polar solvent may be used as a dispersion medium for an application method. In this case, the silver nanowire having polyvinyl pyrrolidone adsorbed thereto is not dispersed in a non-polar solvent but is aggregated, and therefore, such a silver nanowire is unusable. In addition, the silver nanowire is expected to provide further improvement in conductivity or charge injecting properties.

Thus, it is an object of the present invention to provide a metallic composite and a composition thereof that are excellent in dispersibility in a non-polar solvent, applicable also to an application method using a non-polar solvent, and excellent in conductivity and charge injecting properties.

The present invention provides a metallic composite in which a conjugated compound having a molecular weight of 200 or more is adsorbed to a metallic nanostructure having an aspect ratio of 1.5 or more, and a manufacturing method thereof. For the conjugated compound having a molecular weight of 200 or more, a compound having a group represented by the formula (I) below, or a repeating unit represented by the formula (II) below, or both of them is preferable:

$$—Ar^1—(R^1—(X^1)_{m^1})_{n^1} \quad (I)$$

wherein
Ar$^1$ is an (n$^1$+1) valent aromatic group,
R$^1$ is a direct bond or an (m$^1$+1) valent group,
X$^1$ is a hetero atom-containing group,
m$^1$ and n$^1$, which are the same as or different from each other, are an integer of 1 or more, and when R$^1$, X$^1$ and m$^1$ are plurally present, they each may be the same as or different from each other;

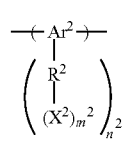

(II)

wherein
Ar$^2$ is an (n$^2$+2) valent aromatic group,
R$^2$ is a direct bond or an (m$^2$+1) valent group,
X$^2$ is a hetero atom-containing group,
m$^2$ and n$^2$, which are the same as or different from each other, are an integer of 1 or more, and
when R$^2$, X$^2$ and m$^2$ are plurally present, they each may be the same as or different from each other.

The present invention also provides a composition comprising the metallic composite and a conjugated compound having a molecular weight of 200 or more.

The present invention further provides an electrode material, an electronic device, and a layered structure, which contain the metallic composite.

The present invention provides a light-emitting device and a photoelectric conversion device, which employ the metallic composite or the composition as a cathode material.

The present invention also provides a conjugated compound comprising one or more structures represented by the formula (III) below, and comprising a repeating unit represented by the formula (II) below and/or a repeating unit represented by the formula (IV) below and/or a repeating unit represented by the formula (V) below.

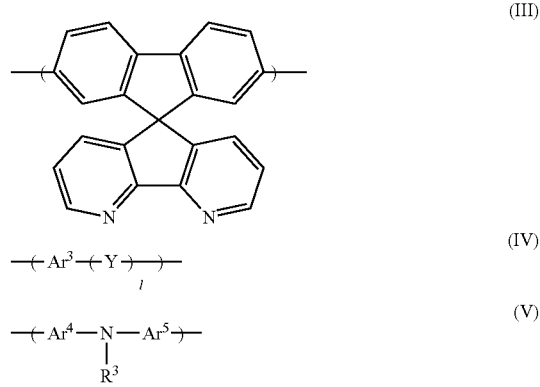

wherein Ar$^3$, Ar$^4$ and Ar$^5$ represent an aromatic group; Y represents a direct bond, an optionally substituted ethenylene group, an ethynylene group, or an optionally substituted azomethine group; l is an integer of 0 to 2; and R$^3$ represents an optionally substituted hydrocarbyl group.

EMBODIMENTS FOR CARRYING OUT THE INVENTION

Figure 1:
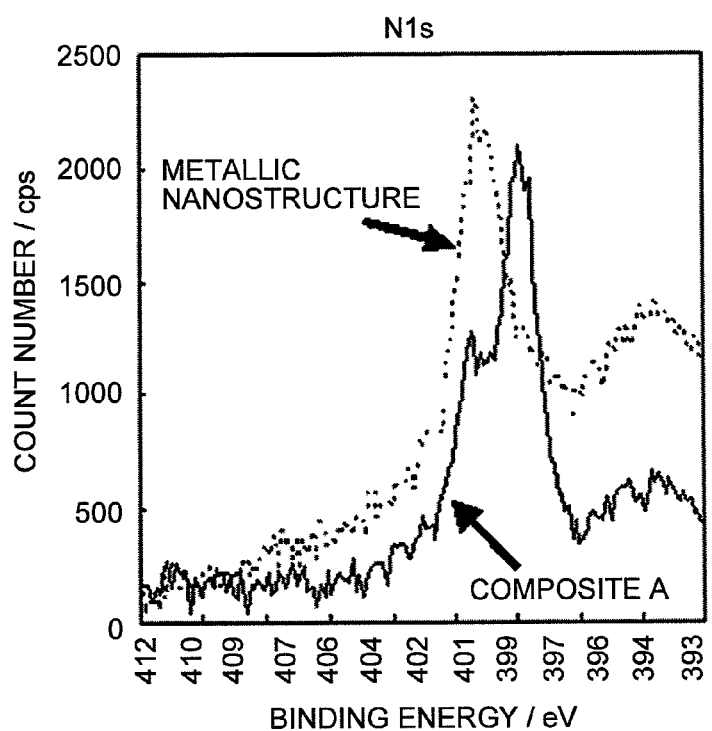
FIG. 1 shows N1s spectra measured by an X-ray photoelectron spectrometry for the composite A obtained in Example 1 and the silver nanostructure A obtained in Synthesis Example 1.

Hereinafter, the present invention is described.

The metallic composite of the present invention is a metallic composite in which a conjugated compound having a molecular weight of 200 or more is adsorbed to a metallic nanostructure having an aspect ratio of 1.5 or more.

In the present specification, "adsorption" means a chemical adsorption and/or a physical adsorption, and from the viewpoint of the adsorption strength, a chemically adsorbed metallic composite is preferred. The chemical adsorption is accompanied by a chemical bond such as a covalent bond, an ionic bond, a metallic bond, a coordination bond and a hydrogen bond between an adsorbate and an adsorbent. Here, the adsorbate is a conjugated compound and the adsorbent is a metallic nanostructure. On the other hand, in the physical adsorption, there is not confirmed a chemical bond between the adsorbate and the adsorbent, and the physical adsorption is a reversible adsorption caused by the physical van der Waals force and the like.

The aspect ratio of the metallic nanostructure means (the largest diameter)/(the smallest diameter), and when the aspect ratio has a distribution, the aspect ratio is an average value. The average value means an arithmetic average value.

From the viewpoint of dispersibility, the aspect ratio is preferably 2 or more, more preferably 5 or more, further preferably 10 or more. When the aspect ratio is less than 1.5, conductivity may be lowered.

The metallic nanostructure means a metal or metal oxide having a diameter of nano size, and the smallest diameter is 1 nm or more and less than 1,000 nm. From the viewpoint of easiness of the synthesis, the smallest diameter is preferably 800 nm or less, more preferably 600 nm or less, further preferably 300 nm or less.

The largest diameter of the metallic nanostructure is usually 1,000 nm or more. From the viewpoint of dispersibility, the largest diameter is preferably 1,300 nm or more, more preferably 1,600 nm or more, further preferably 2,000 nm or more. The largest diameter is usually 250,000 nm or less.

Examples of the shape of the metallic nanostructure may include anisotropic nanoparticle, nanowire, nanorod, and nanosheet. From the viewpoint of easiness of the synthesis, nanorod and nanowire are preferred.

The metal constituting the metallic nanostructure is, from the viewpoint of stability of the metal, preferably a transition metal, more preferably a metal of Group 11 of the Periodic Table, further preferably silver. These metals may be used in combination of two or more types thereof and may be oxidized.

In the present invention, two or more types of metallic nanostructures having aspect ratios different from each other may be used in combination thereof.

When two or more types of metallic nanostructures having aspect ratios different from each other are used, the content of a metallic nanostructure having an aspect ratio less than the half of an average value of aspect ratios is preferably 50% by weight or less, more preferably 40% by weight or less, further preferably 30% by weight or less, particularly preferably 10% by weight or less.

The molecular weight of the conjugated compound is, from the viewpoint of stability of the metallic composite, preferably $3.0 \times 10^2$ to $1.0 \times 10^8$, more preferably $5.0 \times 10^2$ to $1.0 \times 10^7$, further preferably $1.0 \times 10^3$ to $5.0 \times 10^6$. When the molecular weight of the conjugated compound is less than 200, the conjugated compound adsorbed to the metallic composite may be easily separated by evaporation or the like.

The metallic nanostructure of the present invention can be produced by a publicly known method such as a liquid phase method and a gas phase method, and as the metallic nanostructure, a commercially available product may be used as is. More specifically, examples of the method for manufacturing a gold nanostructure may include methods described in JP 2006-233252 A and the like. Examples of the method for manufacturing a silver nanostructure may include methods described in "Xia, Y. et al., Chem. Mater. (2002), 14, 4736-4745", "Xia, Y. et al., Nano Letters (2003), 3, 955-960", "Xia, Y. et al, J. Mater. Chem., (2008) 18, 437-441" and the like. Examples of the method for manufacturing a copper nanostructure may include methods described in JP 2002-266007 A and the like. Examples of the method for manufacturing a cobalt nanostructure may include methods described in JP 2004-149871 A and the like.

In the present specification, the conjugated compound means a compound having a conjugated system, and the conjugated compound is preferably a compound having a system in which a multiple bond (double bond, triple bond); an unshared electron pair that a nitrogen atom, an oxygen atom, a sulfur atom or a phosphorus atom has; a vacant p orbital that a boron atom has; or a σ-bonding d orbital that a silicon atom has aligns each via one single bond. From the viewpoint of electron transporting properties, the conjugated compound has a value calculated by an equation of {(number of atoms contained in a region, in which a multiple bond, an unshared electron pair that a nitrogen atom, an oxygen atom, a sulfur atom or a phosphorus atom has, a vacant p orbital that a boron atom has or a σ-bonding d orbital that a silicon atom has aligns each via one single bond, on the mother skeleton or backbone)/(number of all atoms on the mother skeleton or backbone)}×100% of preferably 50% or more, more preferably 60% or more, more preferably 70% or more, further preferably 80% or more, particularly preferably 90% or more. The conjugated compound is particularly preferably an aromatic compound. From the viewpoint of stability of the metallic composite, the conjugated compound preferably comprises a hetero atom.

The conjugated compound is preferably a compound comprising a group represented by the formula (I) below, or a repeating unit represented by the formula (II) below, or both of them:

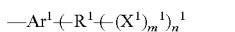   (I)

wherein
Ar$^1$ is an (n$^1$+1) valent aromatic group,
R$^1$ is a direct bond or an (m$^1$+1) valent group,
X$^1$ is a hetero atom-containing group,
m$^1$ and n$^1$, which are the same as or different from each other, are an integer of 1 or more, and
when R$^1$, X$^1$ and m$^1$ are plurally present, they each may be the same as or different from each other;

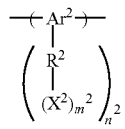   (II)

wherein
Ar$^2$ is an (n$^2$+2) valent aromatic group,
R$^2$ is a direct bond or an (m$^2$+1) valent group,
X$^2$ is a hetero atom-containing group,
m$^2$ and n$^2$, which are the same as or different from each other, are an integer of 1 or more, and
when R$^2$, X$^2$ and m$^2$ are plurally present, they each may be the same as or different from each other.

In the formula (I), the (n$^1$+1) valent aromatic group represented by Ar$^1$ means an atomic group remaining after removing (n$^1$+1) hydrogen atoms from a compound having an optionally substituted aromatic ring.

In the formula (II), the (n$^2$+2) valent aromatic group represented by Ar$^2$ means an atomic group remaining after removing (n$^2$+2) hydrogen atoms from a compound having an optionally substituted aromatic ring.

Examples of the compound having an aromatic ring may include compounds represented by the formulae (1) to (91) below. From the viewpoint of easiness of the synthesis, compounds represented by the formulae (1) to (12), (15) to (22), (24) to (31), (37) to (40), (43) to (46), (49), (50), and (59) to (76) are preferred; compounds represented by the formulae (1) to (3), (8) to (10), (15) to (21), (24) to (31), (37), (39), (43) to (45), (49), (50), and (59) to (76) are more preferred; compounds represented by the formulae (1) to (3), (8), (10), (15), (17), (21), (24), (30), (59), (60), and (61) are further preferred; compounds represented by the formulae (1) to (3), (8), (10), and (59) are particularly preferred; and compounds represented by the formulae (1), (8), and (59) are the most preferred.

(1)

(2)
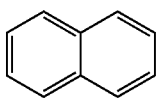

(3)
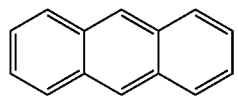

(4)
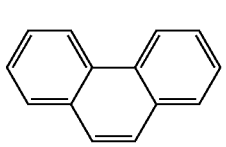

(5)
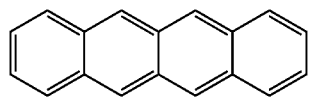

(6)
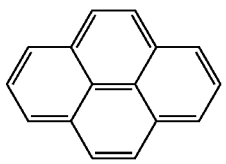

(7)
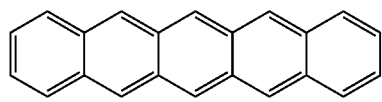

(8)
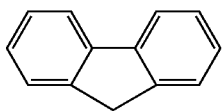

(9)
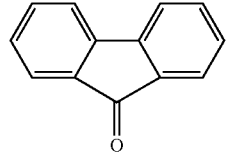

(10)
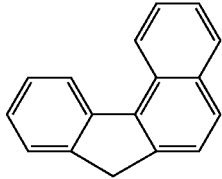

(11)
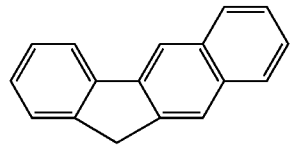

(12)
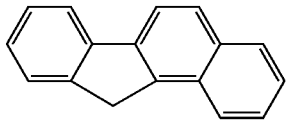

-continued
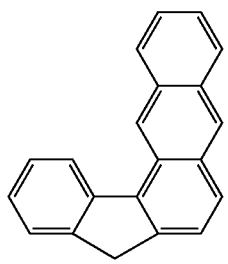
(13)
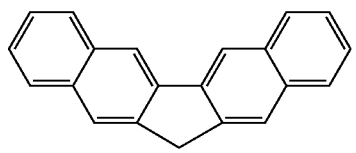
(14)
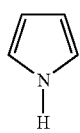
(15)
(16)
(17)
(18)
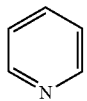
(19)
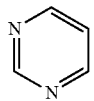
(20)
(21)
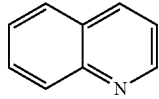
(22)
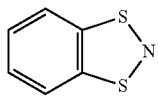
(23)
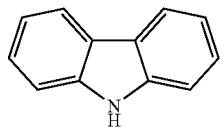
(24)
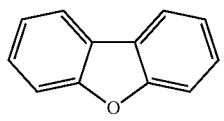
(25)
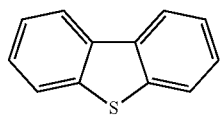
(26)
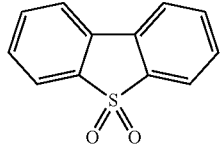
(27)
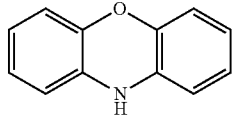
(28)
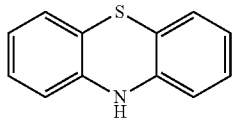
(29)
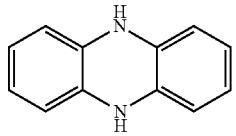
(30)
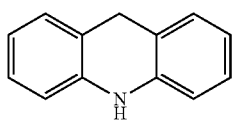
(31)
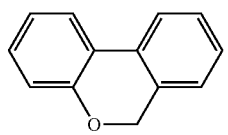
(32)

-continued
(33) 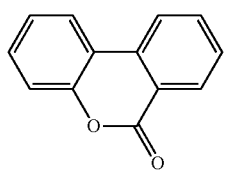
(34) 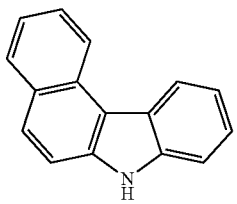
(35) 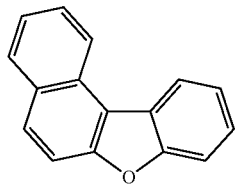
(36) 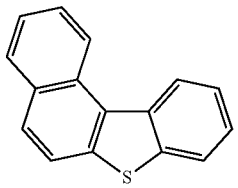
(37) 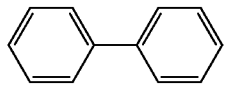
(38) 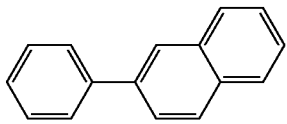
(39) 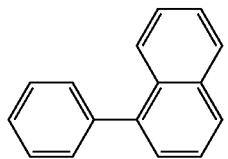
(40) 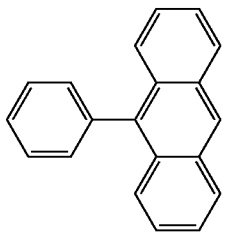
(41) 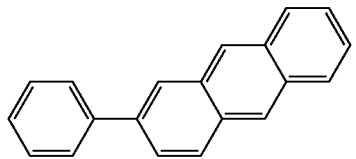
(42) 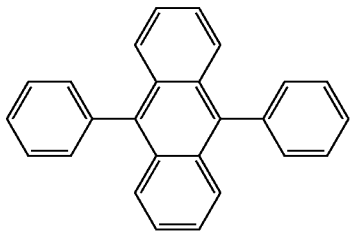
(43) 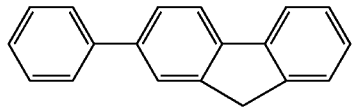
(44) 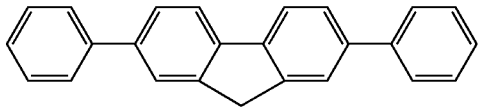
(45) 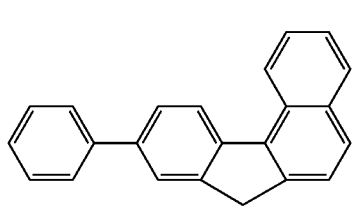
(46) 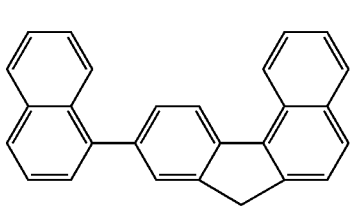
(47) 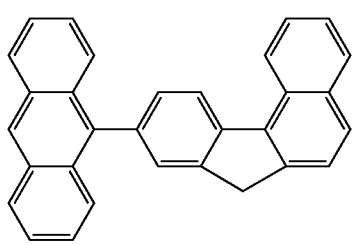
(48) 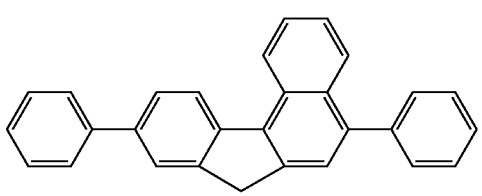

-continued
(49)
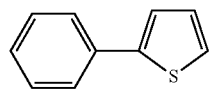
(50)
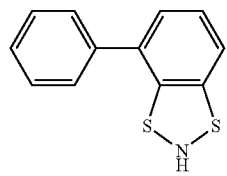
(51)
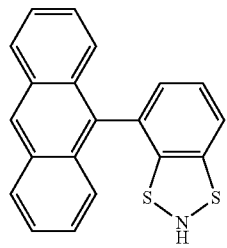
(52)
(53)
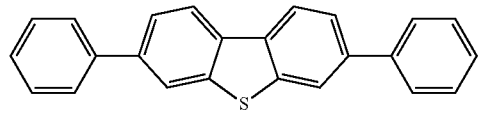
(54)
(55)
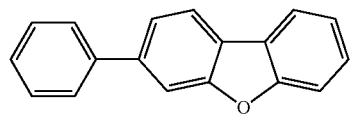
(56)
(57)
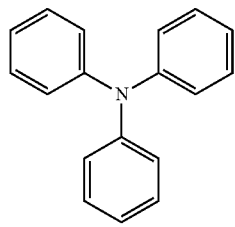
(58)
(59)
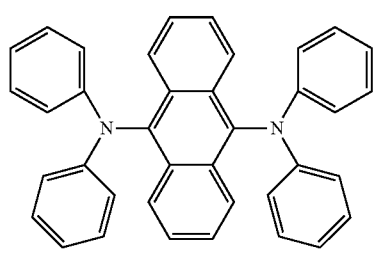
(60)
(61)
(62)
(63)
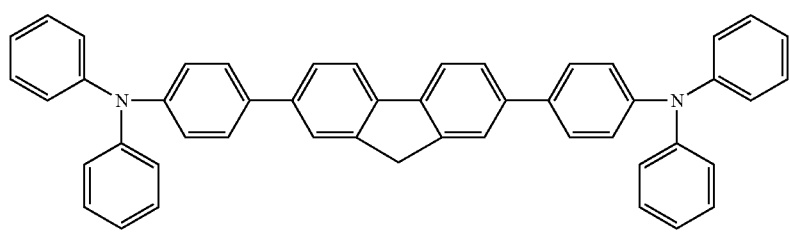

-continued
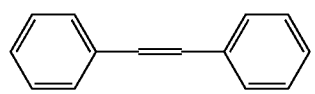 (64)
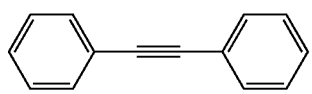 (65)
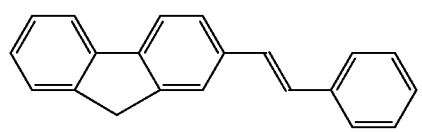 (66)
 (67)
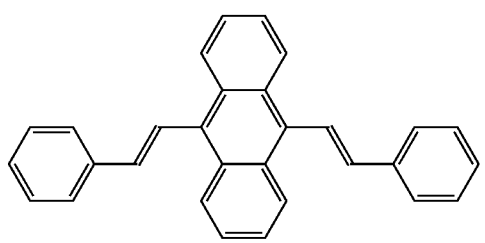
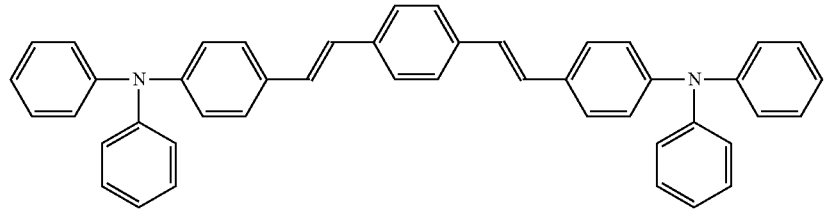 (68)
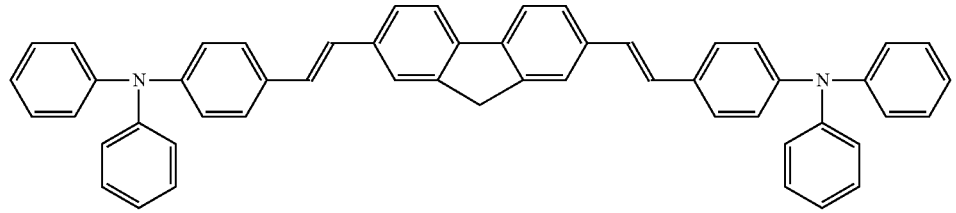 (69)
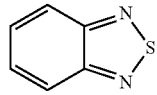 (70)
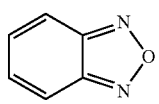 (71)
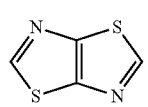 (72)
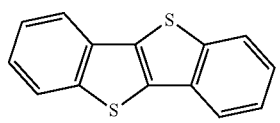 (73)
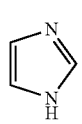 (74)
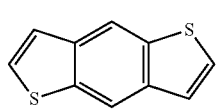 (75)
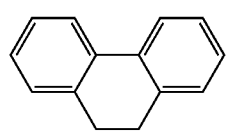 (76)
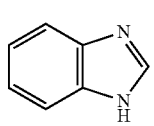 (77)
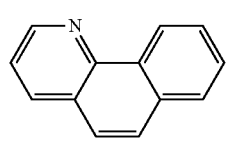 (78)
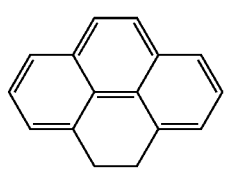 (79)
(80)
(81)

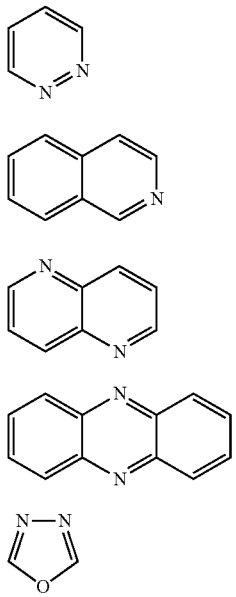
(82)
(84)
(86)
(88)
(90)

(83)

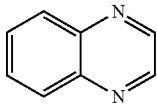
(85)

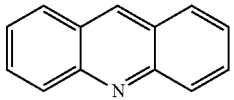
(87)

(89)

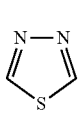
(91)

These compounds having an aromatic ring may be substituted with one or more substituents, and examples of the substituent may include a halogen atom, an optionally substituted hydrocarbyl group, a mercapto group, a mercaptocarbonyl group, a mercaptothiocarbonyl group, an optionally substituted hydrocarbylthio group, an optionally substituted hydrocarbylthiocarbonyl group, an optionally substituted hydrocarbyldithio group, a hydroxy group, an optionally substituted hydrocarbyloxy group, a carboxyl group, an optionally substituted hydrocarbylcarbonyl group, a cyano group, an amino group, an (optionally substituted hydrocarbyl)amino group, an (optionally substituted dihydrocarbyl)amino group, a phosphino group, an (optionally substituted hydrocarbyl)phosphino group, an (optionally substituted dihydrocarbyl)phosphino group, a heterocyclic group, a formyl group, an optionally substituted hydrocarbyloxycarbonyl group, an optionally substituted hydrocarbylcarbonyloxy group, a nitro group, a group represented by formula: —OP(=O) (OH)$_2$, a phosphono group, a carbamoyl group, an (optionally substituted hydrocarbyl)carbamoyl group, an (optionally substituted dihydrocarbyl)carbamoyl group, a group represented by formula: —C(=S)NR$_2$, a group represented by formula: —B(OH)$_2$, a group represented by formula: —BR$_2$, a boric acid ester group, a group represented by formula: —Si(OR)$_3$, a sulfo group, an optionally substituted hydrocarbylsulfo group, an optionally substituted hydrocarbylsulfonyl group, a sulfino group, an optionally substituted hydrocarbylsulfino group, a group represented by formula: —NRC(=O)OR, a group represented by formula: —NRC(=O)SR, a group represented by formula: —NRC(=S)OR, a group represented by formula: —NRC(=S)SR, a group represented by formula: —OC(=O)NR$_2$, a group represented by formula: —SC(=O)NR$_2$, a group represented by formula: —OC(=S)NR$_2$, a group represented by formula: —SC(=S)NR$_2$, a group represented by formula: —NRC(=O)NR$_2$, a group represented by formula: —NRC(=S)NR$_2$, a hydrocarbyl group having two or more ether bonds, a hydrocarbyl group having two or more ester bonds, a hydrocarbyl group having two or more amido bonds, a group represented by formula: —SM, a group represented by formula: —C(=O)SM, a group represented by formula: —CS$_2$M, a group represented by formula: —OM, a group represented by formula: —CO$_2$M, a group represented by formula: —NM$_2$, a group represented by formula: —NHM, a group represented by formula: —NRM, a group represented by formula: —PO$_3$M, a group represented by formula: —OP(=O)(OM)$_2$, a group represented by formula: —P(=O)(OM)$_2$, a group represented by formula: —C(=O)NM$_2$, a group represented by formula: —C(=O)NHM, a group represented by formula: —C(=O)NRM, a group represented by formula: —C(=S)NHM, a group represented by formula: —C(=S)NRM, a group represented by formula: —C(=S)NM$_2$, a group represented by formula: —B(OM)$_2$, a group represented by formula: —BR$_3$M, a group represented by formula: —B(OR)$_3$M, a group represented by formula: —SO$_3$M, a group represented by formula: —SO$_2$M, a group represented by formula: —NRC(=O)OM, a group represented by formula: —NRC(=O)SM, a group represented by formula: —NRC(=S)OM, a group represented by formula: —NRC(=S)SM, a group represented by formula: —OC(=O)NM$_2$, a group represented by formula: —OC(=O)NRM, a group represented by formula: —OC(=S)NM$_2$, a group represented by formula: —OC(=S)NRM, a group represented by formula: —SC(=O)NM$_2$, a group represented by formula: —SC(=O)NRM, a group represented by formula: —SC(=S)NM$_2$, a group represented by formula: —SC(=S)NRM, a group represented by formula: —NRC(=O)NM$_2$, a group represented by formula: —NRC(=O)NRM, a group represented by formula: —NRC(=S)NM$_2$, a group represented by formula: —NRC(=S)NRM, a group represented by formula: —NR$_3$M', a group represented by formula: —PR$_3$M', a group represented by formula: —OR$_2$M', a group represented by formula: —SR$_2$M', a group represented by formula: —IRM', and a heterocyclic group having a cationized nitrogen atom within the heterocycle, wherein R represents a hydrogen atom or an optionally substituted hydrocarbyl group; M represents a metal cation or an optionally substituted ammonium cation; and M' represents an anion. These substituents may be bonded to each other to form a ring.

Among these substituents, preferred examples thereof may include a halogen atom, an optionally substituted hydrocarbyl group, a mercapto group, an optionally substituted hydrocarbylthio group, an optionally substituted hydrocarbyldithio group, a hydroxy group, an optionally substituted hydrocarbyloxy group, a carboxyl group, an optionally substituted hydrocarbylcarbonyl group, a cyano group, an amino group, an (optionally substituted hydrocarbyl)amino group, an optionally substituted dihydrocarbylamino group, a phosphono group, a sulfo group, a heterocyclic group, a group represented by formula: —CO$_2$M, a group represented by formula: —PO$_3$M, a group represented by formula: —SO$_3$M, and a group represented by formula: —NR$_3$M'. More preferred examples thereof may include a halogen atom, an optionally substituted hydrocarbyl group, a mercapto group, a hydroxy group, a carboxyl group, a cyano group, an amino group, a group represented by formula: —P(=O) (OH)$_2$, a sulfo group, a heterocyclic group, a group represented by formula: —CO$_2$M, a group represented by formula: —PO$_3$M, and a group represented by formula: —NR$_3$M'. Further preferred examples thereof may include an optionally substituted hydrocarbyl group, a mercapto group, a carboxyl group, an optionally substituted pyridyl group, and a group represented by formula: —CO$_2$M.

Examples of the halogen atom as a substituent may include a fluorine atom, a chlorine atom, a bromine atom and an iodine atom, and a fluorine atom, a chlorine atom and a bromine atom are preferred.

Examples of the optionally substituted hydrocarbyl group as a substituent may include: $C_{1-50}$ alkyl groups such as a methyl group, an ethyl group, a propyl group, an isopropyl group, a butyl group, an isobutyl group, a tert-butyl group, a pentyl group, a hexyl group, a nonyl group, a dodecyl group, a pentadecyl group, an octadecyl group and a docosyl group; $C_{3-50}$ saturated cyclic hydrocarbon groups such as a cyclopropyl group, a cyclobutyl group, a cyclobutyl group, a cyclopentyl group, a cyclohexyl group, a cyclononyl group, a cyclododecyl group, a norbonyl group and an adamantyl group; $C_{2-50}$ alkenyl groups such as an ethenyl group, a propenyl group, a 3-butenyl group, a 2-butenyl group, a 2-pentenyl group, a 2-hexenyl group, a 2-nonenyl group and a 2-dodecenyl group; $C_{6-50}$ aryl groups such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-tert-butylphenyl group, a 4-hexylphenyl group, a 4-cyclohexylphenyl group, a 4-adamantylphenyl group and a 4-phenylphenyl group; and $C_{7-50}$ aralkyl groups such as a phenylmethyl group, a 1-phenyleneethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group and a 6-phenyl-1-hexyl group. $C_{1-50}$ alkyl groups and $C_{6-50}$ aryl groups are preferred, $C_{1-12}$ alkyl groups and $C_{6-18}$ aryl groups are preferred, and $C_{1-6}$ alkyl groups and $C_{6-12}$ aryl groups are more preferred.

The optionally substituted hydrocarbylthio group, the optionally substituted hydrocarbylthiocarbonyl group, the optionally substituted hydrocarbyldithio group, the optionally substituted hydrocarbyloxy group, the optionally substituted hydrocarbylcarbonyl group, the optionally substituted hydrocarbyloxycarbonyl group and the optionally substituted hydrocarbylcarbonyloxy group as a substituent are a thio group, a thiocarbonyl group, a dithio group, an oxy group, a carbonyl group, an oxycarbonyl group and a carbonyloxy group in which a part of or all of (particularly 1 to 3, more particularly 1 or 2) hydrogen atoms constituting each group are substituted with the hydrocarbyl group.

The hydrocarbylamino group, the dihydrocarbylamino group, the hydrocarbylphosphino group and the dihydrocarbylphosphino group as a substituent are an amino group or a phosphino group in which one or two hydrogen atoms constituting each group are substituted with the hydrocarbyl group.

The hydrocarbylcarbamoyl group and the dihydrocarbylcarbamoyl group as a substituent are a carbamoyl group in which one or two hydrogen atoms constituting each group are substituted with the hydrocarbyl group.

The group represented by formula: —BR$_2$ and the group represented by formula: —Si(OR)$_3$ as a substituent are a group in which R is a hydrogen atom or the hydrocarbyl group, and preferred examples of the hydrocarbyl group are the same as described above.

Examples of the boric acid ester group as a substituent may include groups represented by the following formulae:

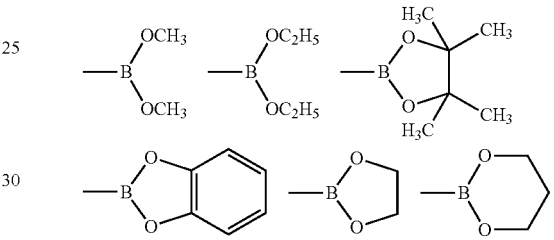

The hydrocarbylsulfo group, the hydrocarbylsulfonyl group and the hydrocarbylsulfino group as a substituent are a sulfo group, a sulfonyl group and a sulfino group in which one or two hydrogen atoms constituting each group are substituted with the hydrocarbyl group.

The group represented by formula: —NRC(=O)OR, the group represented by formula: —NRC(=O)SR, the group represented by formula: —NRC(=S)OR, the group represented by formula: —NRC(=S)SR, the group represented by formula: —OC(=O)NR$_2$, the group represented by formula: —SC(=O)NR$_2$, the group represented by formula: —OC(=S)NR$_2$, the group represented by formula: —SC(=S)NR$_2$, a group represented by formula: —NRC(=O)NR$_2$ and a group represented by formula: —NRC(=S)NR$_2$ as a substituent are a group in which R is a hydrogen atom or the hydrocarbyl group, and preferred examples of the hydrocarbyl group are the same as described above.

The heterocyclic group as a substituent is an atomic group remaining after removing one hydrogen atom from an optionally substituted hetero ring. Examples of the hetero ring may include: a monocyclic hetero ring such as a pyridine ring, a 1,2-diazine ring, a 1,3-diazine ring, a 1,4-diazine ring, a 1,3,5-triazine ring, a furan ring, a pyrrole ring, a thiophene ring, a pyrazole ring, an imidazole ring, an oxazole ring, a thiazole ring, an oxadiazole ring, a thiadiazole ring and an azadiazole ring; a fused multicyclic hetero ring in which two or more rings selected from monocyclic aromatic rings are fused; and a crosslinkage-having multicyclic aromatic ring having a structure in which two hetero rings, or one hetero ring and one aromatic ring are crosslinked through a divalent group such as a methylene group, an ethylene group and a carbonyl group. Among them, a pyridine ring, a 1,2-diazine ring, a 1,3-diazine ring, a 1,4- diazine ring, and a 1,3,5-triazine ring are preferred, and a pyridine ring and a 1,3,5-triazine ring are more preferred.

Examples of the hydrocarbyl group having two or more ether bonds as a substituent may include groups represented by the following formulae:

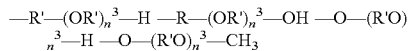

wherein R' represents an optionally substituted hydrocarbondiyl group and R's may be the same as or different from each other; and $n^3$ is an integer of 2 or more.

Examples of the hydrocarbondiyl group may include: optionally substituted $C_{1-50}$ saturated hydrocarbondiyl groups such as a methylene group, an ethylene group, a propylene group, a trimethylene group, a 1,2-butylene group, a 1,3-butylene group, a tetramethylene group, a pentamethylene group, a hexamethylene group, a nonamethylene group, a dodecamethylene group, and a group in which at least one hydrogen atom in these groups is substituted with a substituent; $C_{2-50}$ unsaturated hydrocarbondiyl groups having a substituent or no substituent including optionally substituted $C_{2-50}$ alkenylene groups such as an ethenylene group, a propenylene group, a 3-butenylene group, a 2-butenylene group, a 2-pentenylene group, a 2-hexenylene group, a 2-nonenylene group, a 2-dodecenylene group and a group in which at least one hydrogen atom in these groups is substituted with a substituent, and an ethynylene group; optionally substituted $C_{3-50}$ saturated cyclic hydrocarbondiyl groups such as a cyclopropylene group, a cyclobutylene group, a cyclopentylene group, a cyclohexylene group, a cyclononylene group, a cyclododecylene group, a norbornylene group, an adamantylene group, and a group in which at least one hydrogen atom in these groups is substituted with a substituent; and optionally substituted $C_{6-50}$ arylene groups such as a 1,3-phenylene group, a 1,4-phenylene group, a 1,4-naphthylene group, a 1,5-naphthylene group, a 2,6-naphthylene group, a biphenyl-4,4'-di-yl group, and a group in which at least one hydrogen atom in these groups is substituted with a substituent. When the hydrocarbyl group having an ether bond are plurally present, these groups may combine together to form a ring.

Examples of the hydrocarbyl group having two or more ester bonds as a substituent may include groups represented by the following formulae:

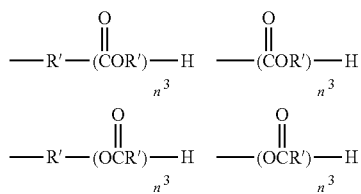

wherein R' and $n^3$ are the same as defined above.

Examples of the hydrocarbyl group having two or more amido bonds as a substituent may include groups represented by the following formulae:

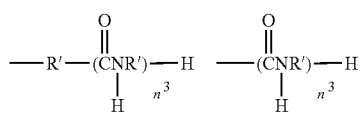

wherein R' and $n^3$ are the same as defined above.

In the group represented by formula: —SM, the group represented by formula: —C(=O)SM, the group represented by formula: —CS$_2$M, the group represented by formula: —OM, the group represented by formula: —CO$_2$M, the group represented by formula: —NM$_2$, the group represented by formula: —NHM, the group represented by formula: —NRM, the group represented by formula: —PO$_3$M, the group represented by formula: —OP(=O)(OM)$_2$, the group represented by formula: —P(=O)(OM)$_2$, the group represented by formula: —C(=O)NM$_2$, the group represented by formula: —C(=O)NRM, the group represented by formula: —C(=S)NRM, the group represented by formula: —C(=S)NM$_2$, the group represented by formula: —B(OM)$_2$, the group represented by formula: —BR$_3$M, the group represented by formula: —B(OR)$_3$M, the group represented by formula: —SO$_3$M, the group represented by formula: —SO$_2$M, the group represented by formula: —NRC(=O)OM, the group represented by formula: —NRC(=O)SM, the group represented by formula: —NRC(=S)OM, the group represented by formula: —NRC(=S)SM, the group represented by formula: —OC(=O)NM$_2$, the group represented by formula: —OC(=O)NRM, the group represented by formula: —OC(=S)NM$_2$, the group represented by formula: —OC(=S)NRM, the group represented by formula: —SC(=O)NM$_2$, the group represented by formula: —SC(=O)NRM, the group represented by formula: —SC(=S)NM$_2$, the group represented by formula: —SC(=S)NRM, the group represented by formula: —NRC(=O)NM$_2$, the group represented by formula: —NRC(=O)NRM, the group represented by formula: —NRC(=S)NM$_2$, and the group represented by formula: —NRC(=S)NRM, M represents a metal cation or an optionally substituted ammonium cation, and R represents a hydrogen atom or a hydrocarbyl group such as an alkyl group, a cycloalkyl group, an aryl group and an aralkyl group.

For the metal cation, a monovalent, divalent, or trivalent ion is preferred, and examples thereof may include metal ions such as Li, Na, K, Cs, Be, Mg, Ca, Ba, Ag, Al, Bi, Cu, Fe, Ga, Mn, Pb, Sn, Ti, V, W, Y, Yb, Zn and Zr. Among them, Li, Na, K and Cs are preferred.

Examples of the substituent that the ammonium cation may have may include $C_{1-10}$ alkyl groups such as a methyl group, an ethyl group, a propyl group, an isopropyl group, a butyl group, an isobutyl group and a tert-butyl group.

In the group represented by formula: —SM, the group represented by formula: —C(=O)SM, the group represented by formula: —CS$_2$M, the group represented by formula: —OM, the group represented by formula: —CO$_2$M, the group represented by formula: —NM$_2$, the group represented by formula: —NHM, the group represented by formula: —NRM, the group represented by formula: —PO$_3$M, the group represented by formula: —OP(=O)(OM)$_2$, the group represented by formula: —P(=O)(OM)$_2$, the group represented by formula: —C(=O)NM$_2$, the group represented by formula: —C(=O)NRM, the group represented by formula: —C(=S)NRM, the group represented by formula: —C(=S)NM$_2$, the group represented by formula: —B(OM)$_2$, the group represented by formula: —BR₃M, the group represented by formula: —B(OR)₃M, the group represented by formula: —SO₃M, the group represented by formula: —SO₂M, the group represented by formula: —NRC(=O)OM, the group represented by formula: —NRC(=O)SM, the group represented by formula: —NRC(=S)OM, the group represented by formula: —NRC(=S)SM, the group represented by formula: —OC(=O)NM₂, the group represented by formula: —OC(=O)NRM, the group represented by formula: —OC(=S)NM₂, the group represented by formula: —OC(=S)NRM, the group represented by formula: —SC(=O)NM₂, the group represented by formula: —SC(=O)NRM, the group represented by formula: —SC(=S)NM₂, the group represented by formula: —SC(=S)NRM, the group represented by formula: —NRC(=O)NM₂, the group represented by formula: —NRC(=O)NRM, the group represented by formula: —NRC(=S)NM₂, and the group represented by formula: —NRC(=S)NRM, a metal cation other than M may coexist or an anion may coexist so as to neutralize the charge of the whole group.

Examples of the anion may include F⁻, Cl⁻, Br⁻, I⁻, OH⁻, ClO⁻, ClO₂⁻, ClO₃⁻, ClO₄⁻, SCN⁻, CN⁻, NO₃⁻, SO₄²⁻, HSO₄⁻, PO₄³⁻, HPO₄²⁻, H₂PO₄⁻, BF₄⁻, PF₆⁻, CH₃SO₃⁻, CF₃SO₃⁻, [(CF₃SO₂)₂N]⁻, tetrakis(imidazolyl) borate anion, 8-quinolinolato anion, 2-methyl-8-quinolinolato anion, and 2-phenyl-8-quinolinolato anion.

In the group represented by formula: —NR₃M', the group represented by formula: —PR₃M', the group represented by formula: —OR₂M', the group represented by formula: —SR₂M', and the group represented by formula: —IRM', R represents a hydrogen atom or a hydrocarbyl group such as an alkyl group, a cycloalkyl group, an aryl group and an aralkyl group, and M' represents an anion. The anion is the same as described above.

The ammonium cation optionally having a substituent represented by M include an ammonium cation having a cationized nitrogen atom within a hetero ring, and specific examples thereof may include atomic groups remaining after removing hydrogen atoms on aromatic rings represented by the formulae (n-1) to (n-13) below. These hetero rings may have a substituent. Examples of the substituent may include the substituents exemplified with respect to Ar¹ and Ar² above. From the viewpoint of easiness of the synthesis, the hetero rings represented by the formulae (n-1), (n-5), (n-7), (n-9), (n-11) and (n-13) are preferred, the hetero rings represented by the formulae (n-1), (n-5), (n-11) and (n-13) are more preferred, and the hetero rings represented by the formulae (n-1), (n-5) and (n-13) are further preferred.

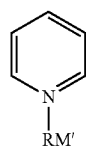
(n-1)

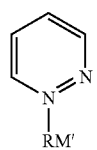
(n-2)

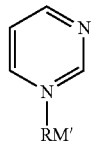
(n-3)

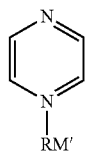
(n-4)

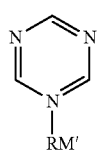
(n-5)

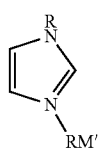
(n-6)

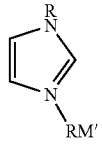
(n-7)

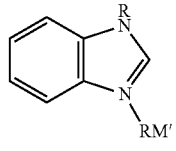
(n-8)

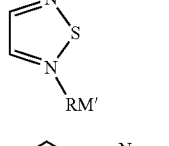
(n-9)

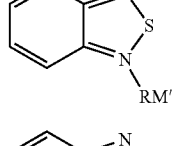
(n-10)

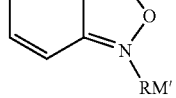
(n-11)

(n-12)

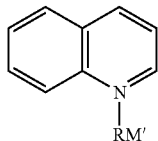
(n-13)

wherein R represents a hydrogen atom or an optionally substituted hydrocarbyl group, and M' represents an anion. R and M' are the same as defined above.

In the formulae (I) and (II), the hetero atom-containing groups represented by $X^1$ and $X^2$ are, from the viewpoints of the adsorptivity and the dispersibility in a solvent, preferably a group containing at least one hetero atom selected from the group consisting of a sulfur atom, an oxygen atom, a nitrogen atom and a phosphorus atom, more preferably a mercapto group, a mercaptocarbonyl group, a mercaptothiocarbonyl group, an optionally substituted hydrocarbylthio group, an optionally substituted hydrocarbylthiocarbonyl group, an optionally substituted hydrocarbyldithio group, a hydroxy group, an optionally substituted hydrocarbyloxy group, a carboxyl group, an optionally substituted hydrocarbylcarbonyl group, a cyano group, an amino group, an (optionally substituted hydrocarbyl)amino group, an optionally substituted dihydrocarbylamino group, a phosphino group, an optionally substituted hydrocarbylphosphino group, an optionally substituted dihydrocarbylphosphino group, a phosphono group, a sulfo group, and a heterocyclic group (these groups are called "Group 1a"), further preferably a mercapto group, an optionally substituted hydrocarbylthio group, an optionally substituted hydrocarbyldithio group, a hydroxy group, an optionally substituted hydrocarbyloxy group, a carboxyl group, an optionally substituted hydrocarbylcarbonyl group, a cyano group, an amino group, an (optionally substituted hydrocarbyl)amino group, an optionally substituted dihydrocarbylamino group, a group represented by formula: —P(=O) (OH)$_2$, a sulfo group, and a heterocyclic group, particularly preferably a mercapto group, a hydroxy group, a carboxyl group, a cyano group, an amino group, a group represented by formula: —P(=O) (OH)$_2$, a sulfo group, and a heterocyclic group, and the most preferably a mercapto group, a carboxyl group, and a pyridyl group. These groups may combine together to form a ring.

Examples of the group preferred from the viewpoints of the adsorptivity and the dispersibility in a solvent may include a halogen atom, a formyl group, an optionally substituted hydrocarbyloxycarbonyl group, an optionally substituted hydrocarbylcarbonyloxy group, a nitro group, a group represented by formula: —OP(=O) (OH)$_2$, a phosphono group, a carbamoyl group, an (optionally substituted hydrocarbyl)carbamoyl group, an optionally substituted dihydrocarbylcarbamoyl group, a group represented by formula: —C(=S)NR$_2$, a group represented by formula: —B(OH)$_2$, a group represented by formula: —BR$_2$, a boric acid ester group, a group represented by formula: —Si (OR)$_3$, an optionally substituted hydrocarbylsulfo group, an optionally substituted hydrocarbylsulfonyl group, a sulfino group, an optionally substituted hydrocarbylsulfino group, a group represented by formula: —NRC(=O)OR, a group represented by formula: —NRC(=O)SR, a group represented by formula: —NRC(=S)OR, a group represented by formula: —NRC(=S)SR, a group represented by formula: —OC(=O)NR$_2$, a group represented by formula: —SC(=O)NR$_2$, a group represented by formula: —OC(=S) NR$_2$, a group represented by formula: —SC(=S)NR$_2$, a group represented by formula: —NRC(=O)NR$_2$, and a group represented by formula: —NRC(=S)NR$_2$ (these groups are called "Group 1b"). These groups (Group 1a and Group 1b) preferred from the viewpoints of the adsorptivity and the dispersibility in a solvent are called "Group 1".

From the viewpoint of the conductivity or the charge injecting properties of the metallic composite, a hydrocarbyl group having two or more ether bonds, a hydrocarbyl group having two or more ester bonds, a hydrocarbyl group having two or more amido bonds, a group represented by formula: —SM, a group represented by formula: —C(=O)SM, a group represented by formula: —CS$_2$M, a group represented by formula: —OM, a group represented by formula: —CO$_2$M, a group represented by formula: —NM$_2$, a group represented by formula: —NHM, a group represented by formula: —NRM, a group represented by formula: —PO$_3$M, a group represented by formula: —OP(=O) (OM)$_2$, a group represented by formula: —P(=O) (OM)$_2$, a group represented by formula: —C(=O)NM$_2$, a group represented by formula: —C(=O)NHM, a group represented by formula: —C(=O)NRM, a group represented by formula: —C(=S) NHM, a group represented by formula: —C(=S)NRM, a group represented by formula: —C(=S)NM$_2$, a group represented by formula: —B(OM)$_2$, a group represented by formula: —BR$_3$M, a group represented by formula: —B(OR)$_3$M, a group represented by formula: —SO$_3$M, a group represented by formula: —SO$_2$M, a group represented by formula: —NRC(=O)OM, a group represented by formula: —NRC(=O)SM, a group represented by formula: —NRC(=S)OM, a group represented by formula: —NRC (=S)SM, a group represented by formula: —OC(=O)NM$_2$, a group represented by formula: —OC(=O)NRM, a group represented by formula: —OC(=S)NM$_2$, a group represented by formula: —OC(=S)NRM, a group represented by formula: —SC(=O)NM$_2$, a group represented by formula: —SC(=O)NRM, a group represented by formula: —SC (=S)NM$_2$, a group represented by formula: —SC(=S) NRM, a group represented by formula: —NRC(=O)NM$_2$, a group represented by formula: —NRC(=O)NRM, a group represented by formula: —NRC(=S)NM$_2$, a group represented by formula: —NRC(=S)NRM, a group represented by formula: —NR$_3$M', a group represented by formula: —PR$_3$M', a group represented by formula: —OR$_2$M', a group represented by formula: —SR$_2$M', and a group represented by formula: —IRM'. These groups are called "Group 2". These groups may combine together to form a ring. Among them, a group represented by formula: —OM, a group represented by formula: —CO$_2$M, a group represented by formula: —PO$_3$M$_2$, a group represented by formula: —SO$_3$M, and a group represented by formula: —NR$_3$M' are more preferred; a group represented by formula: —CO$_2$M, a group represented by formula: —P(=O) (OM)$_2$, a group represented by formula: —SO$_3$M, and a group represented by formula: —NR$_3$M' are further preferred; a group represented by formula: —CO$_2$M, a group represented by formula: —PO$_3$M$_2$, and a group represented by formula: —NR$_3$M' are particularly preferred; and a group represented by formula: —CO$_2$M is the most preferred.

M, R and M' are the same as defined above.

In the formula (I), examples of the ($m^1$+1) valent group represented by $R^1$ may include atomic groups remaining after removing $m^1$ hydrogen atoms from the optionally substituted hydrocarbyl group or the heterocyclic group, and these groups may combine together to form a ring. The ($m^1$+1) valent group represented by $R^1$ is preferably an atomic group remaining after removing $m^1$ hydrogen atoms from an optionally substituted alkyl group, an atomic group remaining after removing $m^1$ hydrogen atoms from an optionally substituted aryl group, an atomic group remaining after removing $m^1$ hydrogen atoms from a heterocyclic group, an atomic group remaining after removing $m^1$ hydrogen atoms from an alkyl group substituted with a heterocyclic group, and an atomic group remaining after removing $m^1$ hydrogen atoms from an aryl group substituted with a heterocyclic group, more preferably an atomic group remaining after removing $m^1$ hydrogen atoms from a $C_{1-6}$ alkyl group, an atomic group remaining after removing $m^1$ hydrogen atoms from a phenyl group, an atomic group remaining after removing $m^1$ hydrogen atoms from a triazinyl group, an atomic group remaining after removing $m^1$ hydrogen atoms from an alkyl group substituted with a triazinyl group, and an atomic group remaining after removing $m^1$ hydrogen atoms from an aryl group substituted with a triazinyl group, further preferably an atomic group remaining after removing $m^1$ hydrogen atoms from a hexyl group, an atomic group remaining after removing $m^1$ hydrogen atoms from a phenyl group, and an atomic group remaining after removing $m^1$ hydrogen atoms from a phenyl group substituted with a triazinyl group.

In the formula (II), examples of the $(m^2+1)$ valent group represented by $R^2$ may include an atomic group remaining after removing $m^2$ hydrogen atoms from the optionally substituted hydrocarbyl group or the heterocyclic group, and these groups may combine together to form a ring. The $(m^2+1)$ valent group represented by $R^2$ is preferably an atomic group remaining after removing $m^2$ hydrogen atoms from an optionally substituted alkyl group, an atomic group remaining after removing $m^2$ hydrogen atoms from an optionally substituted aryl group, an atomic group remaining after removing $m^2$ hydrogen atoms from a heterocyclic group, an atomic group remaining after removing $m^2$ hydrogen atoms from an alkyl group substituted with a heterocyclic group, and an atomic group remaining after removing $m^2$ hydrogen atoms from an aryl group substituted with a heterocyclic group, more preferably an atomic group remaining after removing $m^2$ hydrogen atoms from a $C_{1-6}$ alkyl group, an atomic group remaining after removing $m^2$ hydrogen atoms from a phenyl group, an atomic group remaining after removing $m^2$ hydrogen atoms from a triazinyl group, an atomic group remaining after removing $m^2$ hydrogen atoms from an alkyl group substituted with a triazinyl group, and an atomic group remaining after removing $m^2$ hydrogen atoms from an aryl group substituted with a triazinyl group, further preferably an atomic group remaining after removing $m^2$ hydrogen atoms from a hexyl group, an atomic group remaining after removing $m^2$ hydrogen atoms from a phenyl group, and an atomic group remaining after removing $m^2$ hydrogen atoms from a phenyl group substituted with a triazinyl group.

The conjugated compound has preferably at least one type of the Group 1 and at least one type of the Group 2.

The conjugated compound has preferably at least one of the Group 1 or a repeating unit containing the Group 1, and at least one of the Group 2 or a repeating unit containing the Group 2.

It is particularly preferable that the conjugated compound has at least one repeating unit containing the Group 1 and at least one repeating unit containing the Group 2.

Specific examples of the conjugated compound of the present invention may include conjugated compounds having a repeating unit represented by the formulae (a-1) to (a-35), (b-1) to (b-39), (c-1) to (c-37), (d-1) to (d-47), (e-1) to (e-16), (f-1) to (f-35), and (g-1) to (g-24) below, wherein $n^3$ represents an integer of 2 or more, preferably an integer of 2 to 30, more preferably an integer of 2 to 20, and further preferably an integer of 6 to 10; $n^4$ represents an integer of 1 or more, preferably an integer of 1 to 10, and further preferably an integer of 2 to 6; and R represents a hydrogen atom or a hydrocarbyl group, preferably a $C_{1-6}$ alkyl group, and further preferably a methyl group, an ethyl group, a propyl group and a butyl group.

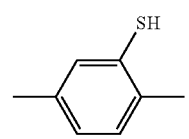
(a-1)

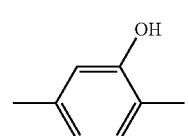
(a-2)

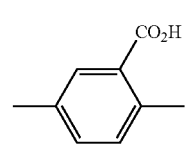
(a-3)

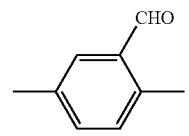
(a-4)

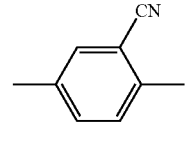
(a-5)

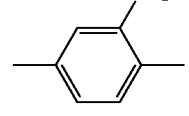
(a-6)

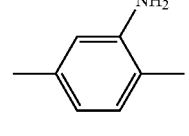
(a-7)

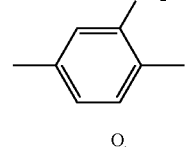
(a-8)

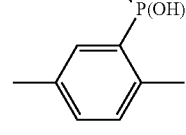
(a-9)

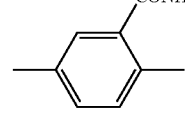
(a-10)

(a-11) 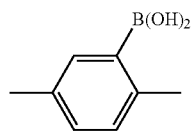
(a-12) 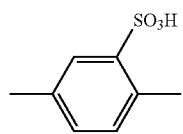
(a-13) 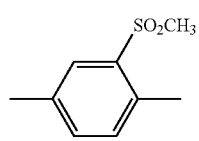
(a-14) 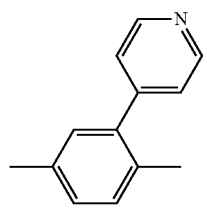
(a-15) 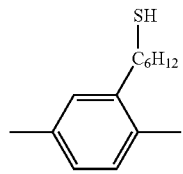
(a-16) 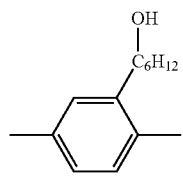
(a-17) 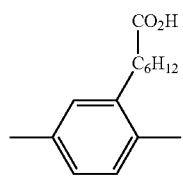
(a-18) 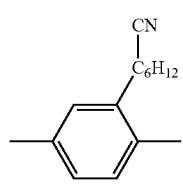
(a-19) 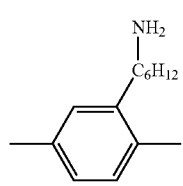
(a-20) 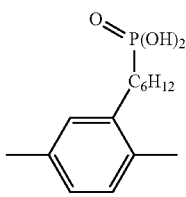
(a-21) 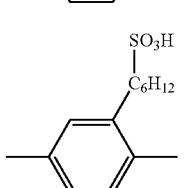
(a-22) 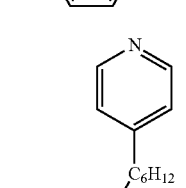
(a-23) 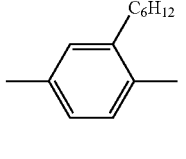
(a-24) 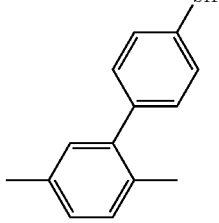
(a-25) 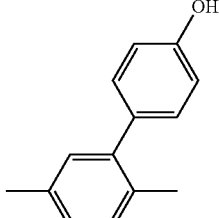
(a-26) 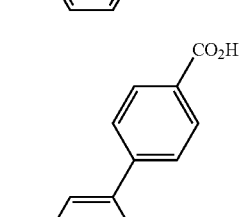

(a-27) 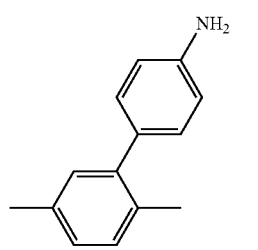
(a-28) 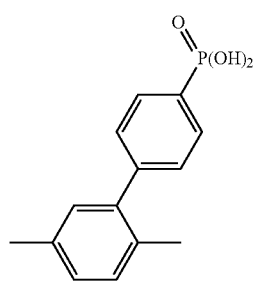
(a-29) 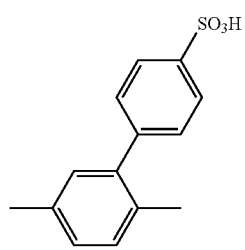
(a-30) 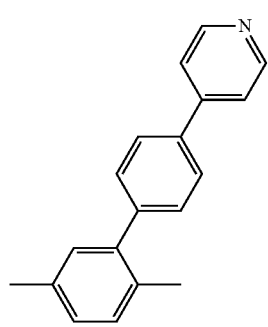
(a-31) 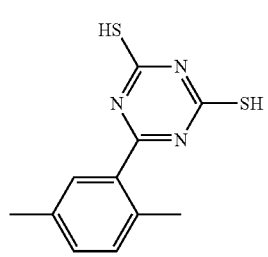
(a-32) 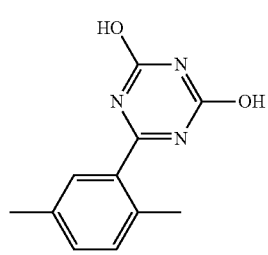
(a-33) 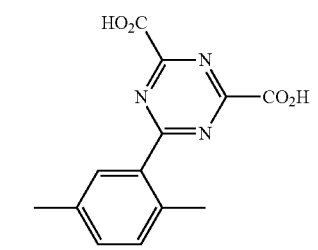
(a-34) 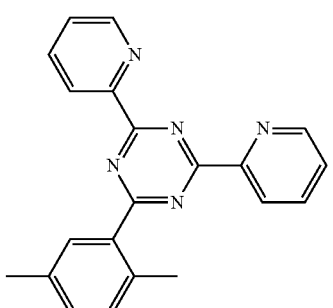
(a-35) 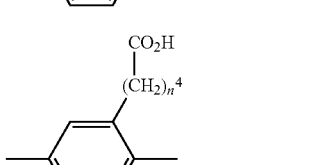
(b-1) 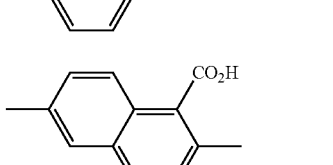
(b-2) 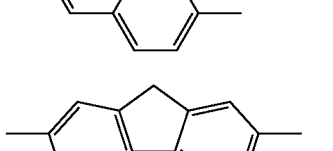
(b-3) 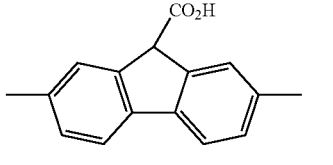
(b-4) 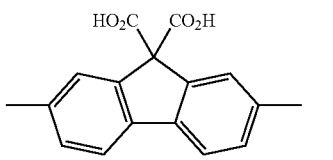
(b-5) 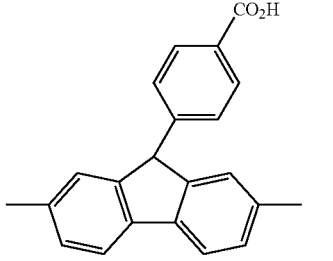

-continued
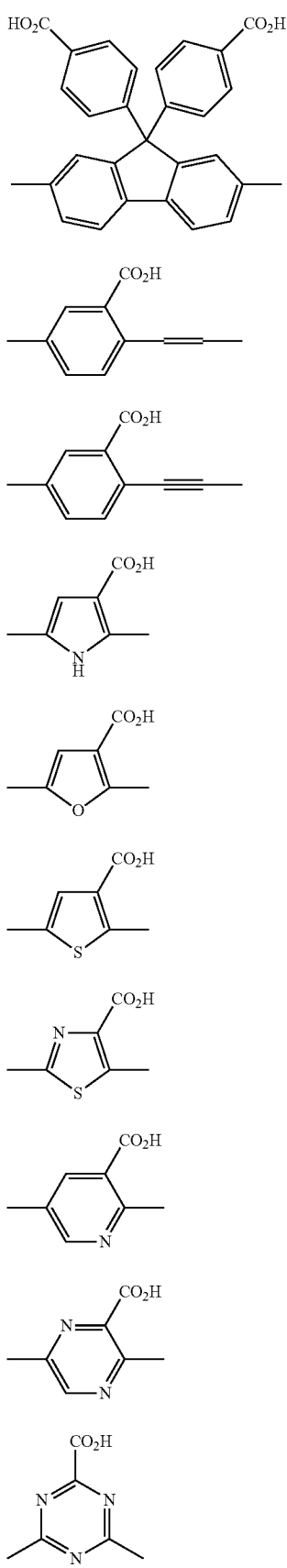
(b-6)
(b-7)
(b-8)
(b-9)
(b-10)
(b-11)
(b-12)
(b-13)
(b-14)
(b-15)
-continued
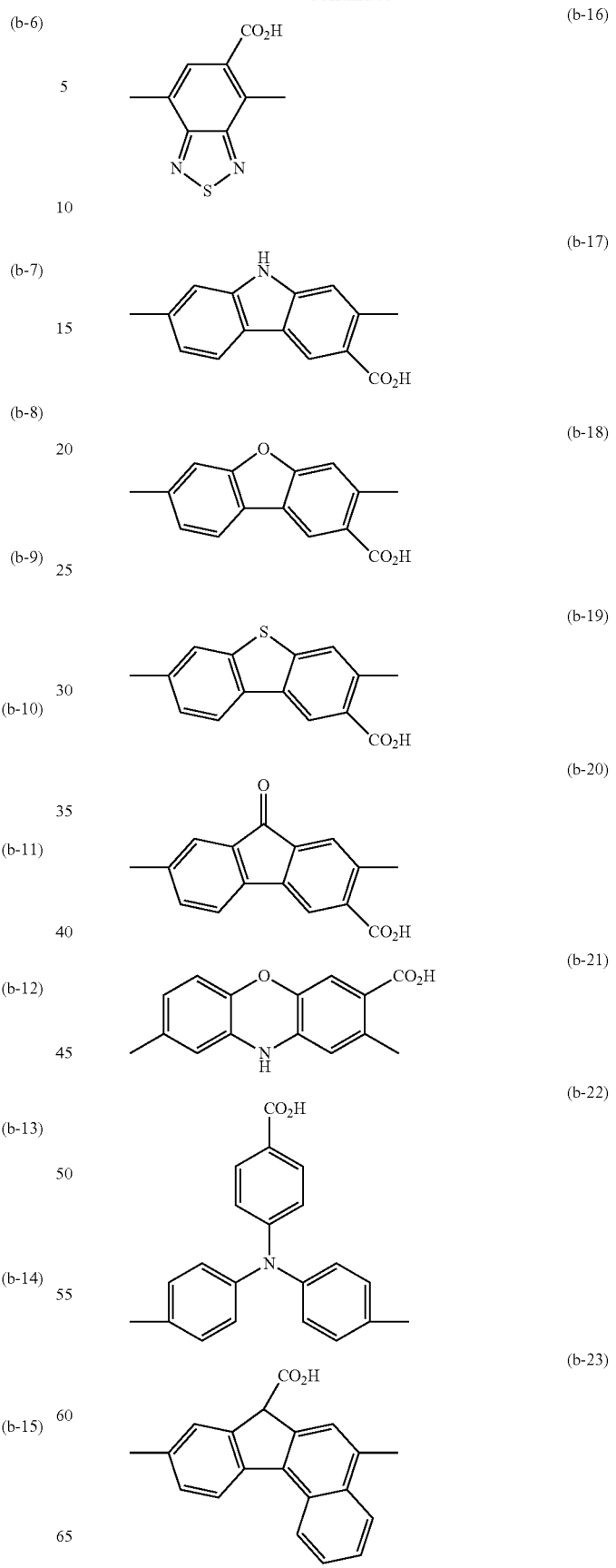
(b-16)
(b-17)
(b-18)
(b-19)
(b-20)
(b-21)
(b-22)
(b-23)

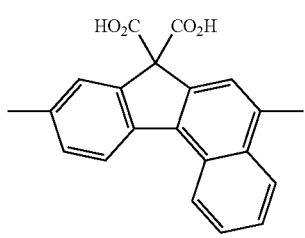
(b-24)
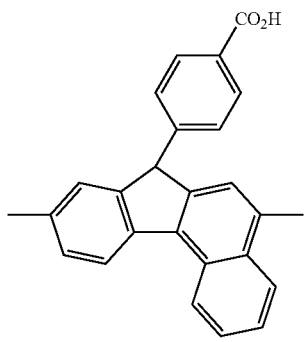
(b-25)
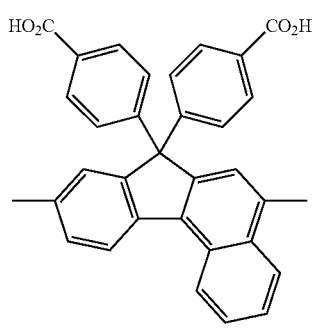
(b-26)
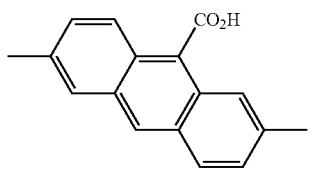
(b-27)
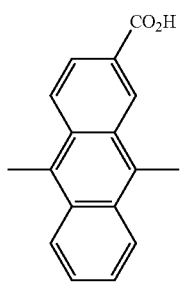
(b-28)
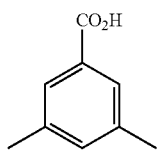
(b-29)
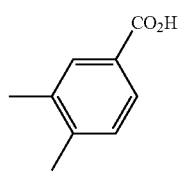
(b-30)
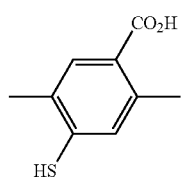
(b-31)
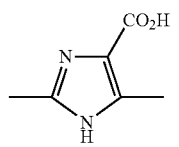
(b-32)
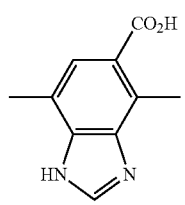
(b-33)
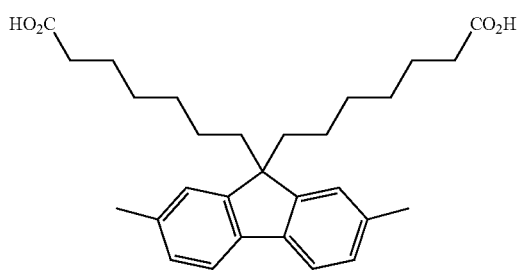
(b-34)
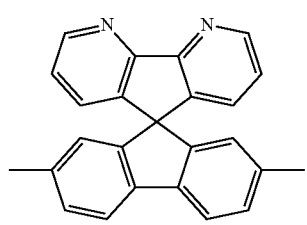
(b-35)
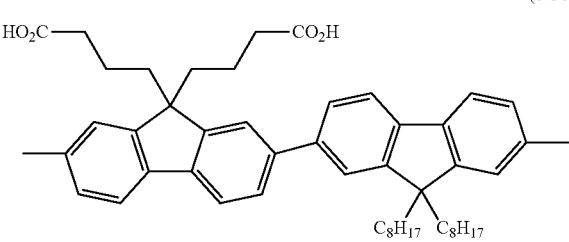
(b-36)

(b-37)
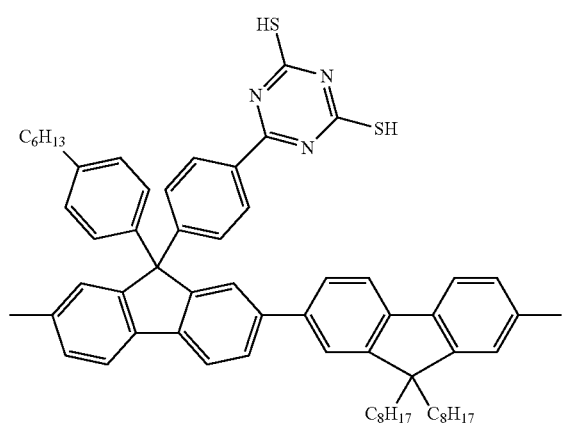
(b-38)
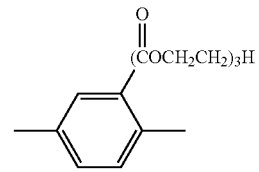
(b-39)
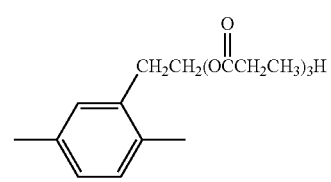
(c-1)
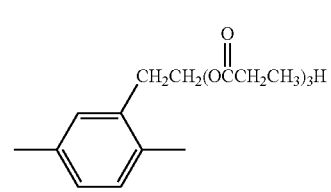
(c-2)
(c-3)
(c-4)
(c-5)
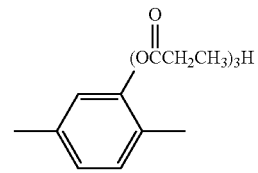
(c-6)
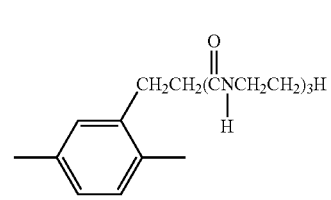
(c-7)
(c-8)
(c-9)
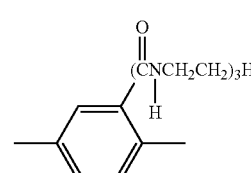
(c-10)
(c-11)
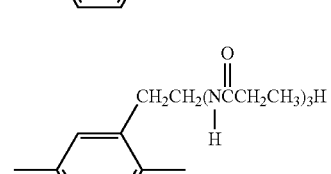
(c-12)
(c-13)
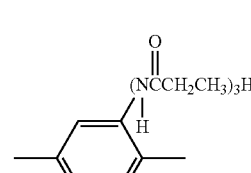
(c-14)
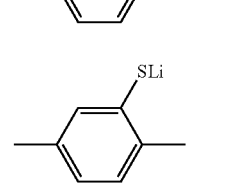

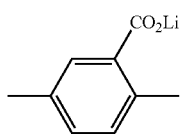 (c-15)
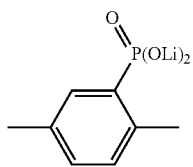 (c-16)
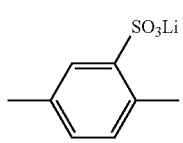 (c-17)
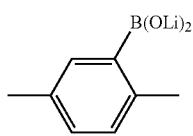 (c-18)
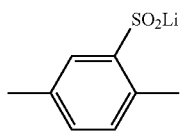 (c-19)
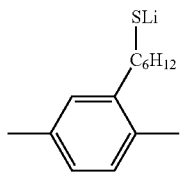 (c-20)
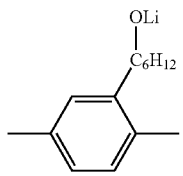 (c-21)
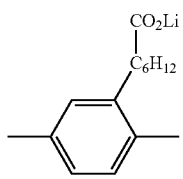 (c-22)
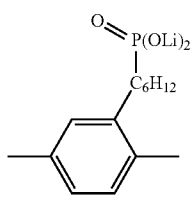 (c-23)
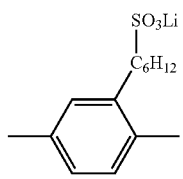 (c-24)
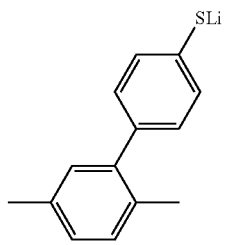 (c-25)
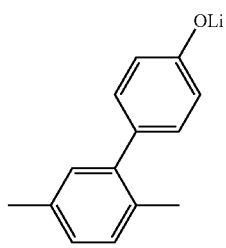 (c-26)
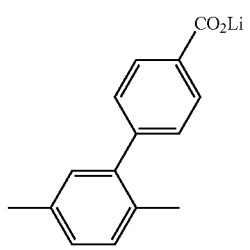 (c-27)
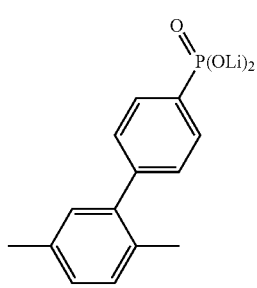 (c-28)
(c-29)

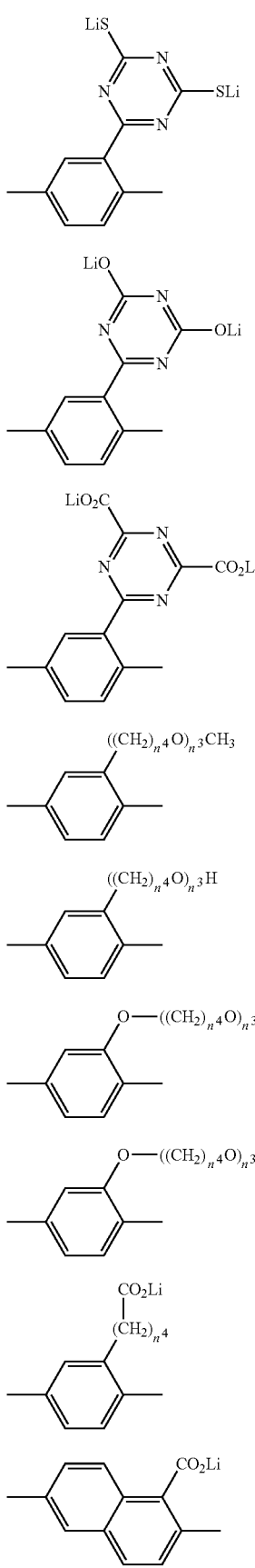
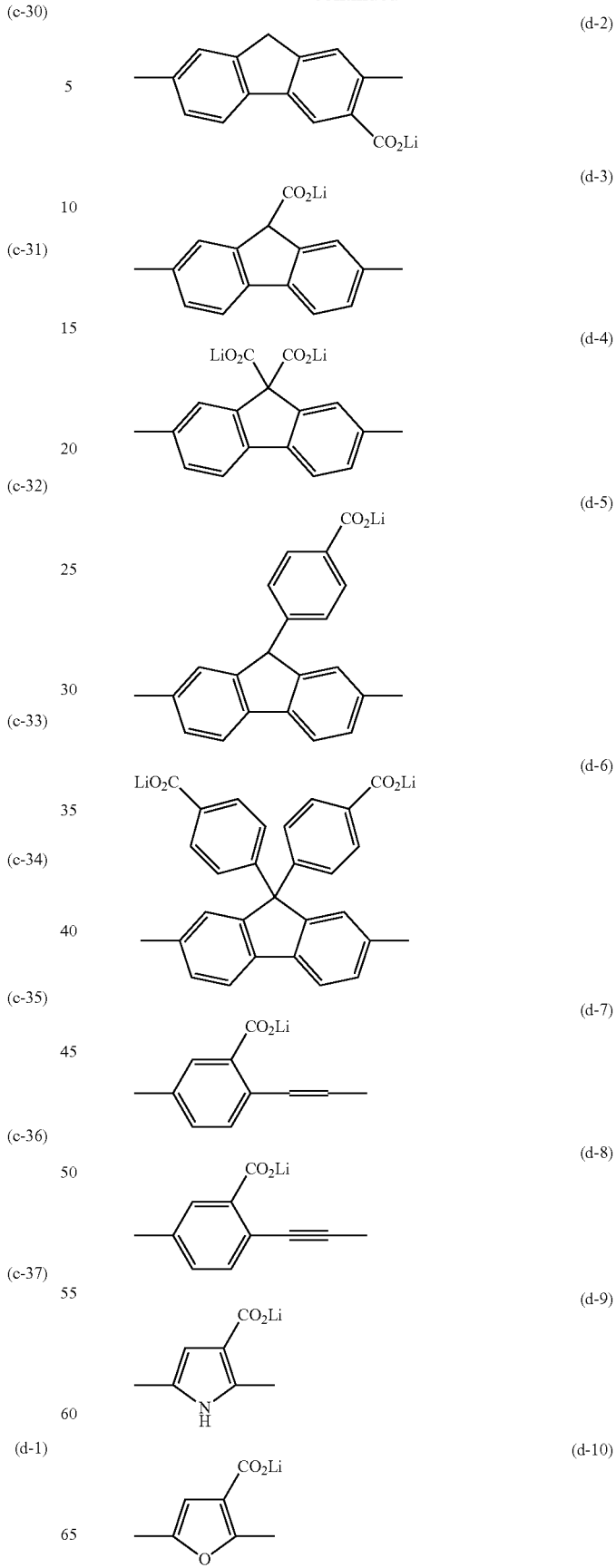

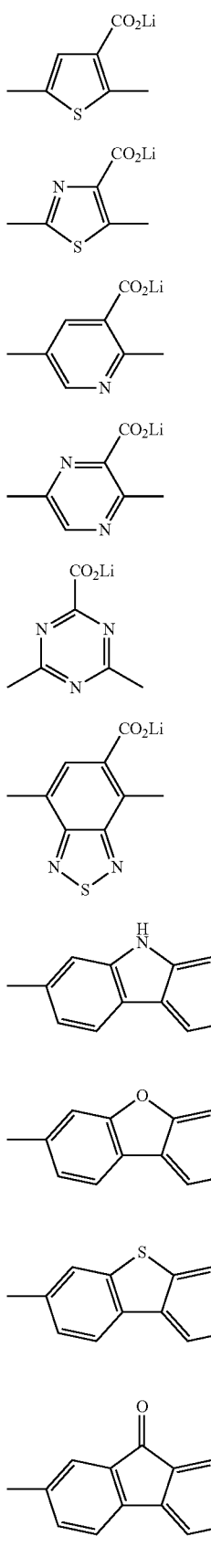
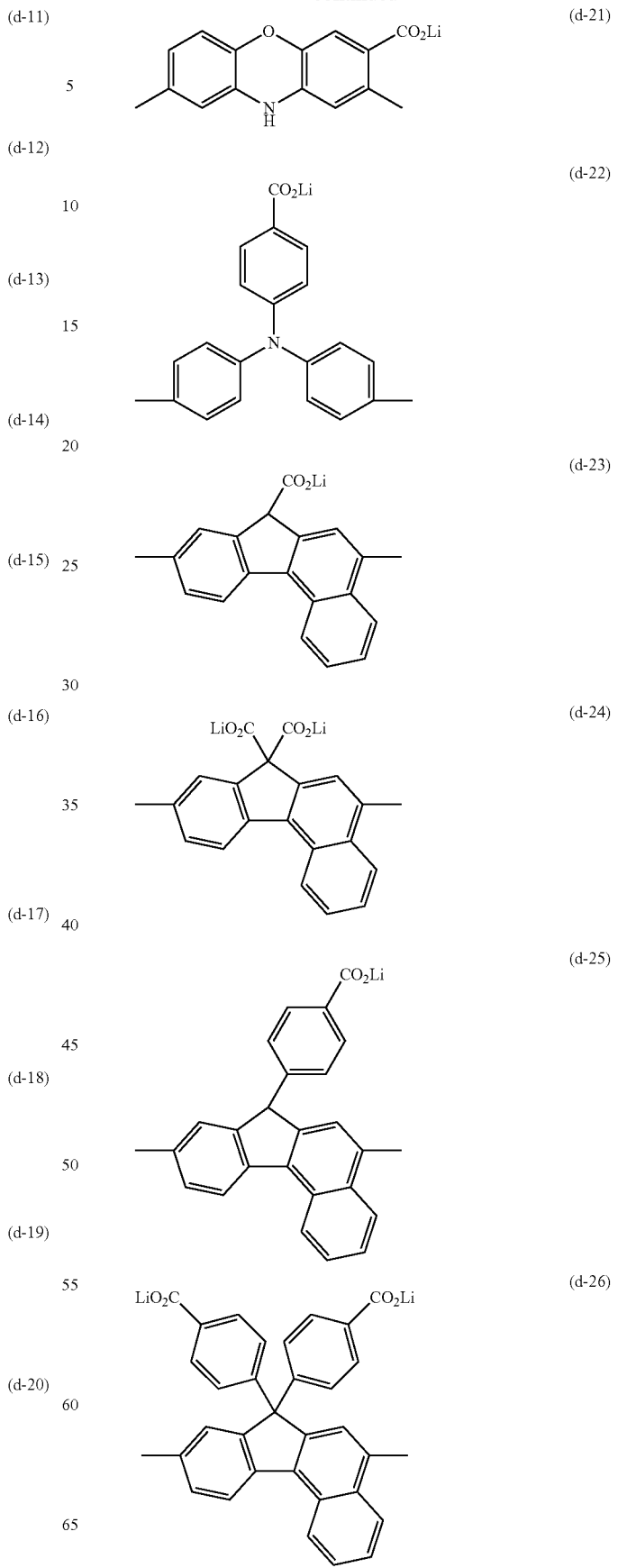

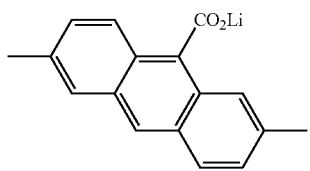 (d-27)
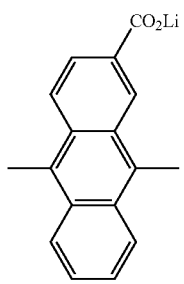 (d-28)
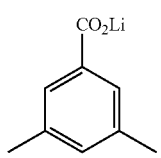 (d-29)
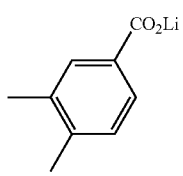 (d-30)
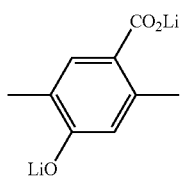 (d-31)
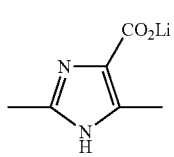 (d-32)
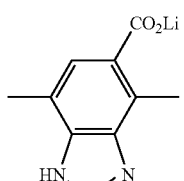 (d-33)
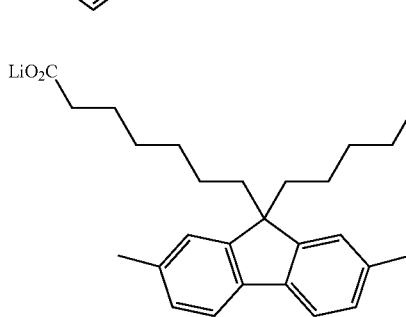 (d-34)
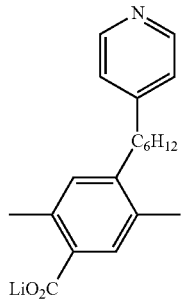 (d-35)
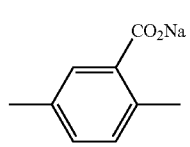 (d-36)
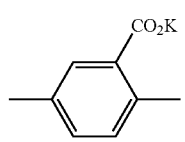 (d-37)
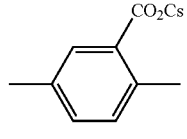 (d-38)
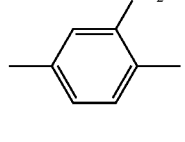 (d-39)
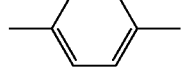 (d-40)
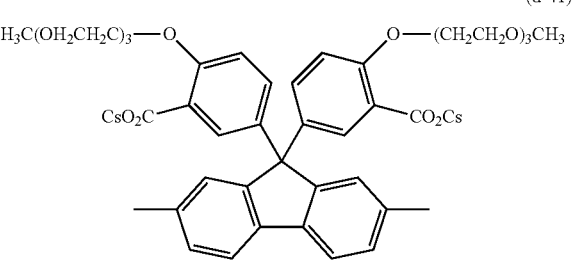 (d-41)
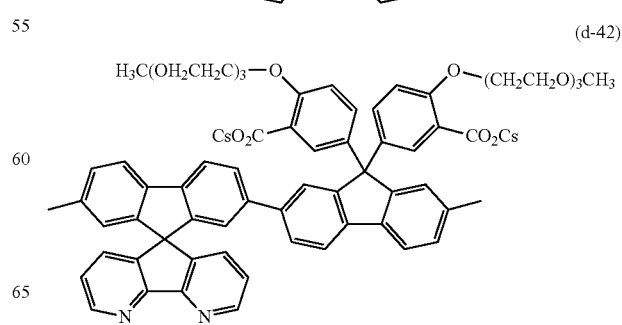 (d-42)

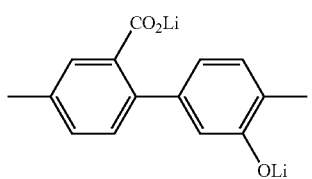 (d-43)
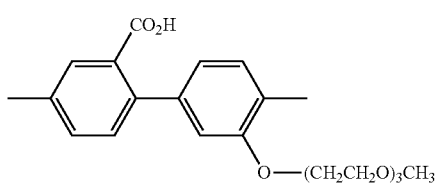 (d-44)
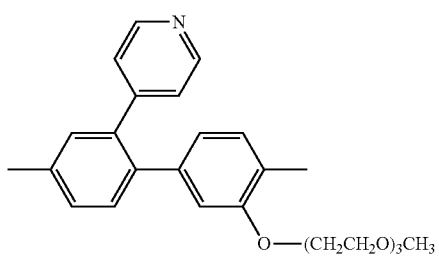 (d-45)
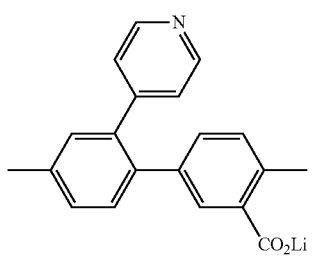 (d-46)
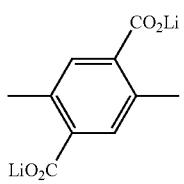 (d-47)
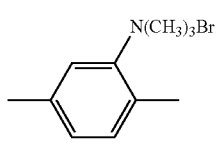 (e-1)
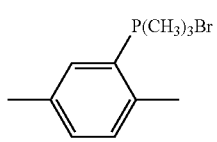 (e-2)
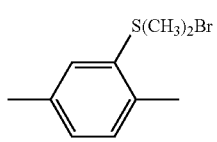 (e-3)
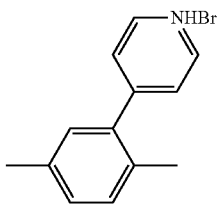 (e-4)
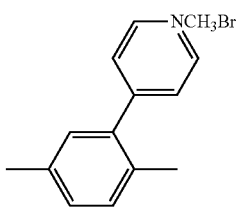 (e-5)
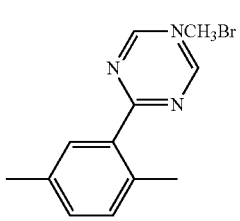 (e-6)
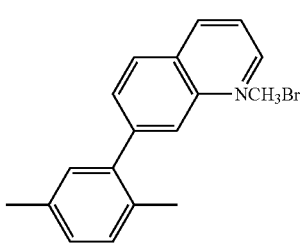 (e-7)
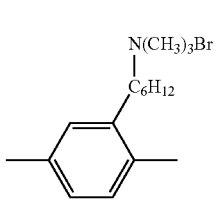 (e-8)
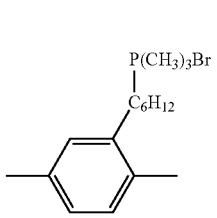 (e-9)
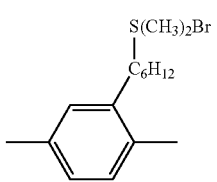 (e-10)

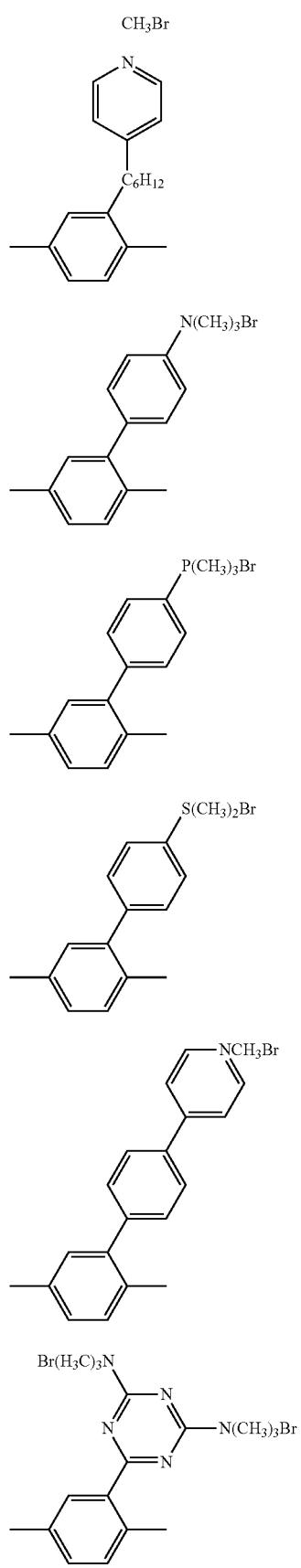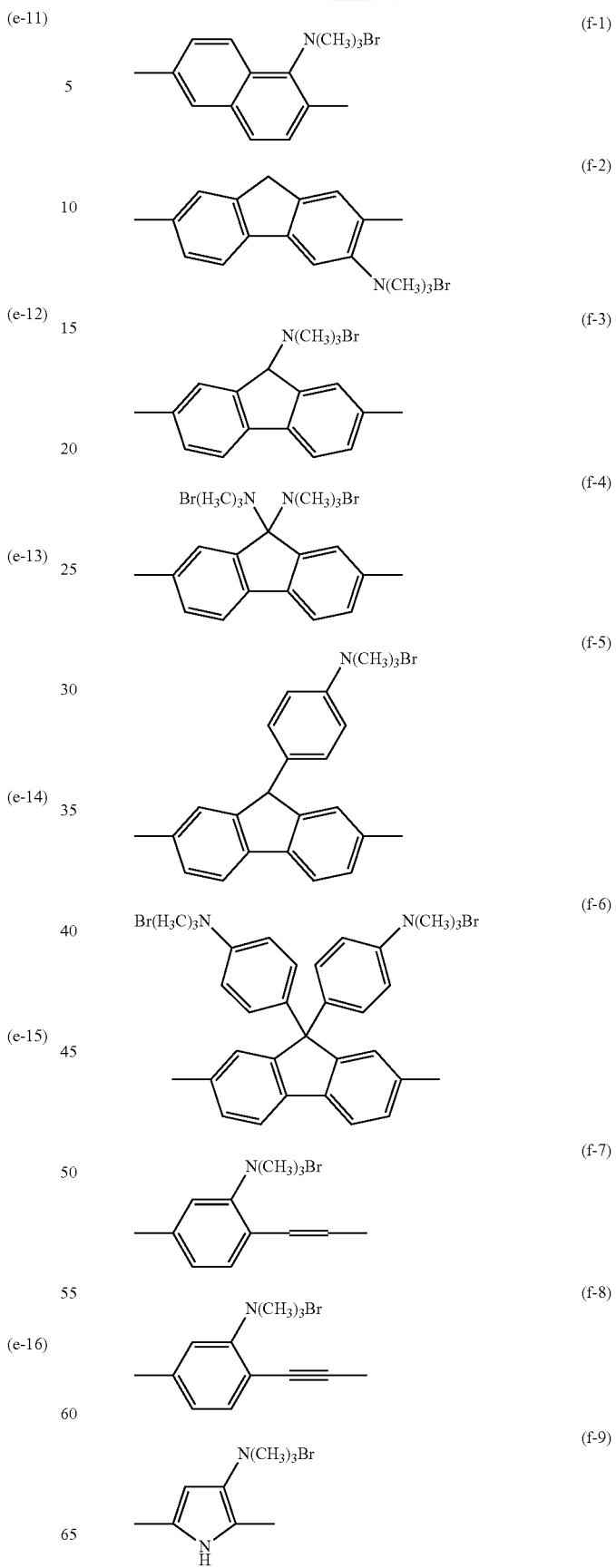

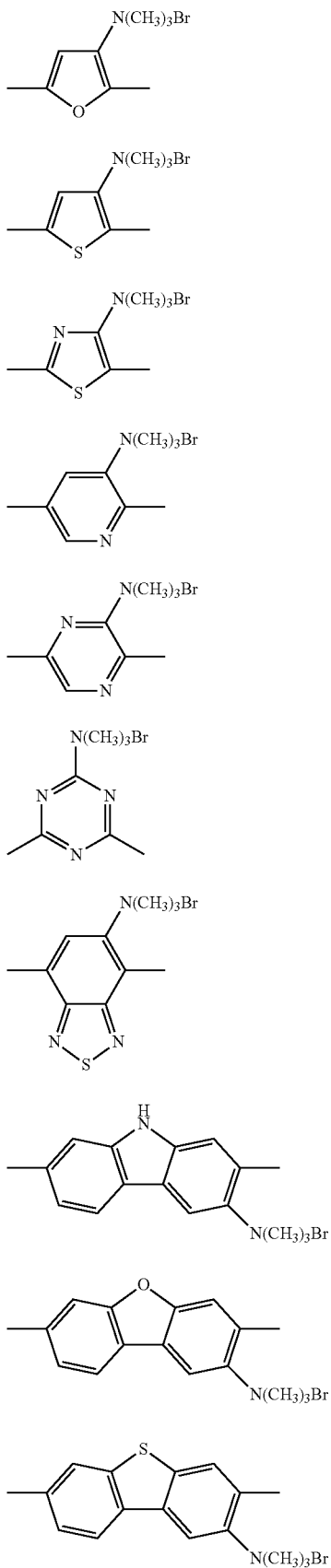
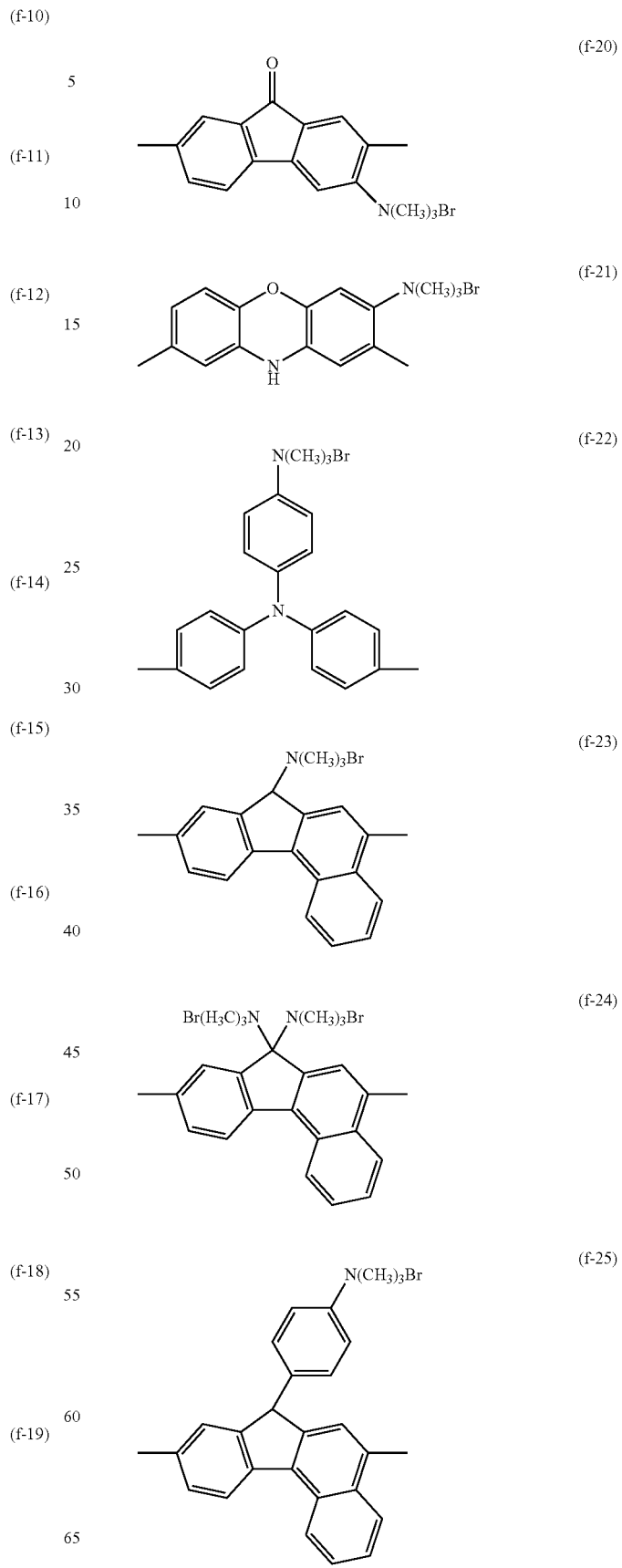

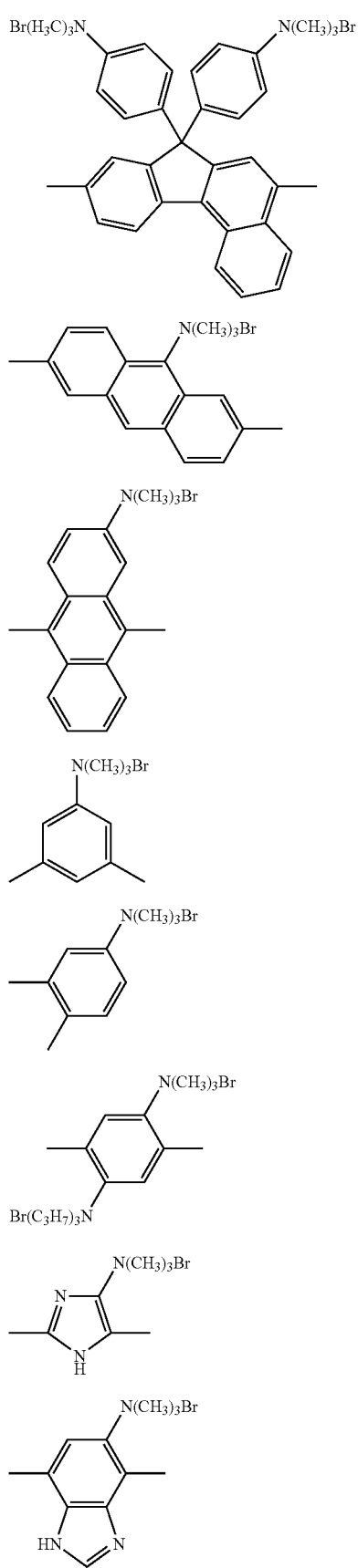
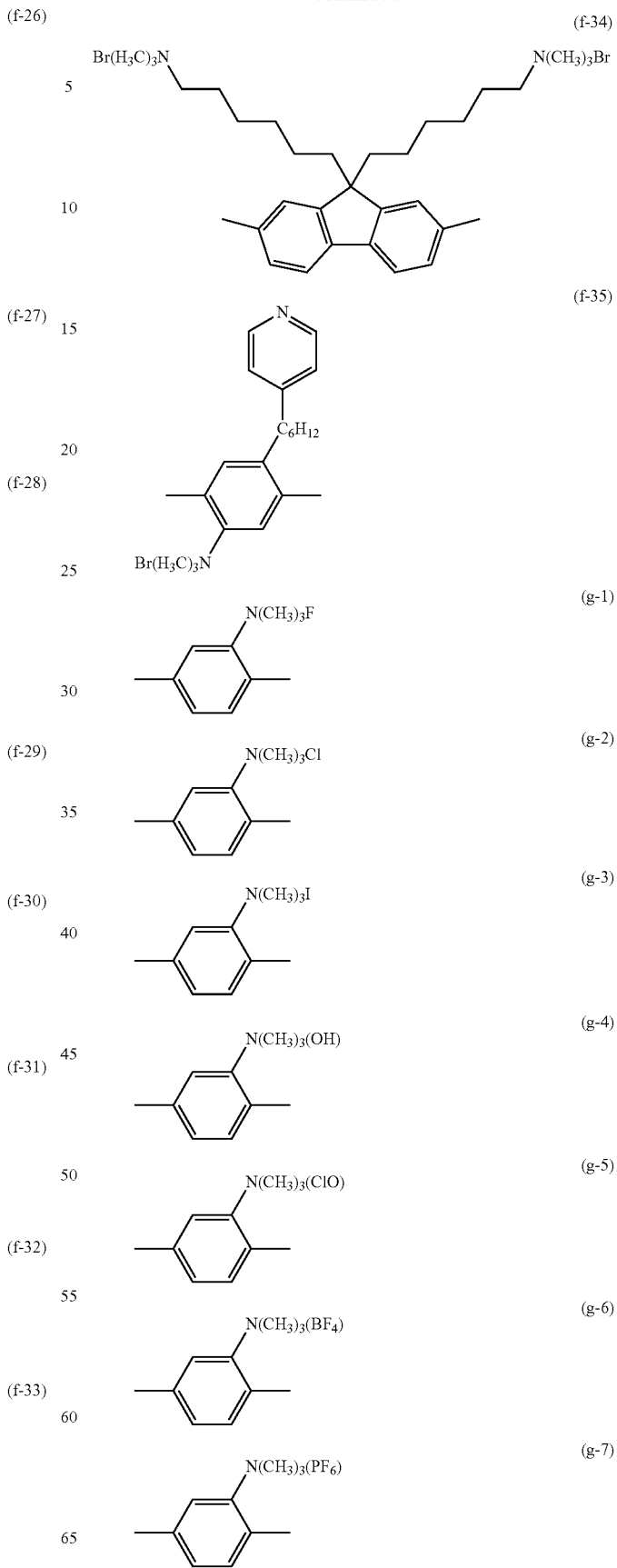

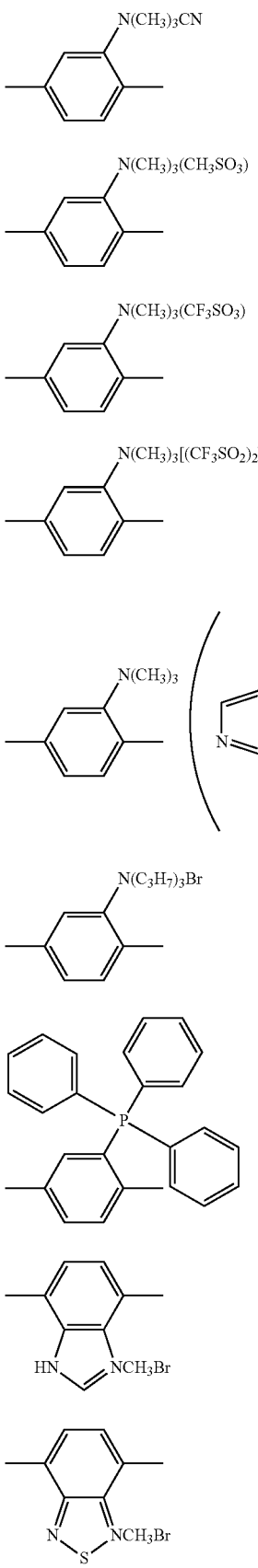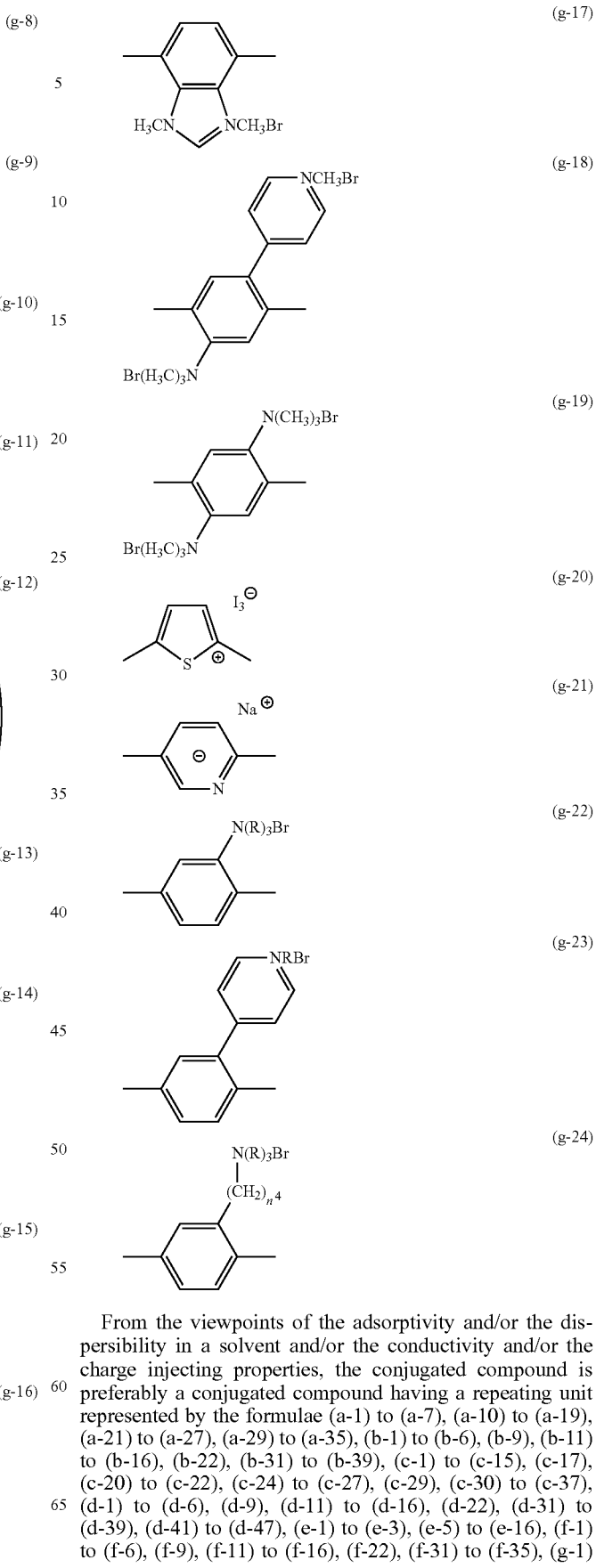

From the viewpoints of the adsorptivity and/or the dispersibility in a solvent and/or the conductivity and/or the charge injecting properties, the conjugated compound is preferably a conjugated compound having a repeating unit represented by the formulae (a-1) to (a-7), (a-10) to (a-19), (a-21) to (a-27), (a-29) to (a-35), (b-1) to (b-6), (b-9), (b-11) to (b-16), (b-22), (b-31) to (b-39), (c-1) to (c-15), (c-17), (c-20) to (c-22), (c-24) to (c-27), (c-29), (c-30) to (c-37), (d-1) to (d-6), (d-9), (d-11) to (d-16), (d-22), (d-31) to (d-39), (d-41) to (d-47), (e-1) to (e-3), (e-5) to (e-16), (f-1) to (f-6), (f-9), (f-11) to (f-16), (f-22), (f-31) to (f-35), (g-1)

to (g-13), and (g-16) to (g-24), more preferably a conjugated compound having a repeating unit represented by the formulae (a-1) to (a-3), (a-5), (a-7), (a-10), (a-12), (a-14) to (a-19), (a-21) to (a-27), (a-29) to (a-33), (b-1) to (b-6), (b-9), (b-11), (b-13), (b-15), (b-16), (b-22), (b-34) to (b-39), (c-1) to (c-15), (c-17), (c-20) to (c-22), (c-24) to (c-27), (c-29) to (c-32), (c-34) to (c-37), (d-1) to (d-6), (d-9), (d-11), (d-13), (d-15), (d-16), (d-22), (d-31) to (d-39), (d-41), (d-42), (d-47), (e-1), (e-5) to (e-8), (e-11), (e-12), (e-15), (e-16), (f-1) to (f-6), (f-9), (f-11), (f-13), (f-15), (f-16), (f-22), (f-31), (f-34), (f-35), (g-1) to (g-3), (g-6) to (g-13), and (g-16) to (g-24), further preferably a conjugated compound having a repeating unit represented by the formulae (a-1), (a-3), (a-7), (a-10), (a-14), (a-15), (a-17), (a-19), (a-22), (a-23), (a-25) to (a-27), (a-30), (a-31), (b-1), (b-2), (b-5), (b-6), (b-9), (b-11), (b-13), (b-22), (b-34) to (b-39), (c-1) to (c-4), (c-13) (c-15), (c-20) to (c-22), (c-25) to (c-27), (c-30) to (c-32), (d-1), (d-2), (d-5), (d-6), (d-9), (d-11), (d-13), (d-22), (d-31) to (d-38), (d-41), (d-42), (d-47), (e-1), (e-5), (e-7), (e-8), (e-11), (e-12), (e-15), (e-16), (f-1), (f-2), (f-5), (f-6), (f-9), (f-11), (f-13), (f-22), (f-31), (f-34), (f-35), (g-1) to (g-3), (g-6), (g-7), (g-9) to (g-13), and (g-18) to (g-21), particularly preferably a conjugated compound having a repeating unit represented by the formulae (a-3), (a-14), (a-22), (a-17), (a-25), (a-30), (a-31), (b-6), (b-22), (b-34) to (b-37), (b-39), (c-1) to (c-4), (c-15), (c-22), (c-27), (d-6), (d-22), (d-34) to (d-38), (d-41), (d-42), (e-1), (e-5), (e-8), (e-12), (e-15), (f-6), (f-34), (g-2), (g-6), (g-7), (g-10) to (g-12), and (g-18) to (g-21), especially preferably a conjugated compound having a repeating unit represented by the formulae (b-6), (b-34), (b-35), (b-37), (c-1) to (c-4), (d-6), (d-34), (d-36) to (d-38), (d-41), (d-42), (f-6), (f-34), (g-2), and (g-10) to (g-12), and the most preferably a conjugated compound having a repeating unit represented by the formulae (b-6), (b-34), (b-37), (c-1) to (c-4), (d-38), (d-41), and (d-42).

Among the above examples of the conjugated compound having the repeating unit, an example in which one of two bonds is replaced by a hydrogen atom is an example for a group represented by the formula (I).

When the conjugated compound is a compound having a group represented by the formula (I), or a repeating unit represented by the formula (II), or both of them, the conjugated compound may further have a repeating unit different from a repeating unit represented by the formula (II).

Examples of the different repeating unit may include an atomic group remaining after removing two hydrogen atoms from the compound having an aromatic ring, an atomic group remaining after removing one hydrogen atom from the hydrocarbyl group, and an atomic group remaining after removing one hydrogen atom from the heterocyclic group. Among them, an atomic group remaining after removing two hydrogen atoms from the compound having an aromatic ring and an atomic group remaining after removing one hydrogen atom from the hydrocarbyl group are preferred, and an atomic group remaining after removing two hydrogen atoms from the compound having an aromatic ring is more preferred. These atomic groups may be substituted. The repeating unit represented by the formula (II) may be bonded through a divalent group represented by the following formulae (h-1) to (h-19):

—O— (h-1)

—S— (h-2)

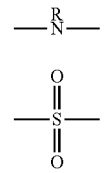 (h-3)

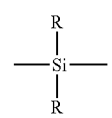 (h-4)

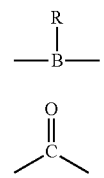 (h-5)

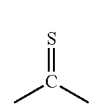 (h-6)

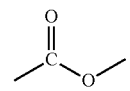 (h-7)

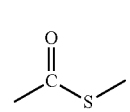 (h-8)

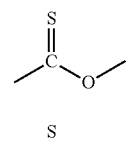 (h-9)

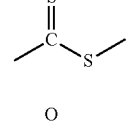 (h-10)

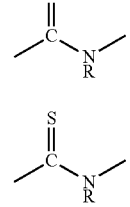 (h-11)

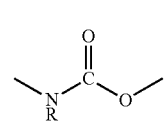 (h-12)

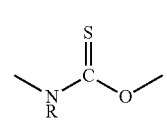 (h-13)

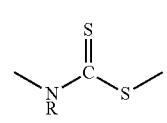 (h-14)

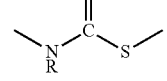 (h-15)

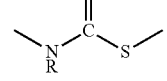 (h-16)

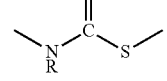 (h-17)

-continued

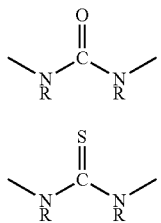

(h-18)

(h-19)

wherein R represents a hydrogen atom or an optionally substituted hydrocarbyl group.

Examples of the substituent that the atomic group of the different repeating unit may have may include the same groups as the substituent that the compound having an aromatic ring may have.

When the conjugated compound has the different repeating unit, the different repeating unit is preferably introduced within a range where the conjugation of the conjugated compound is not inhibited.

The aspects of the conjugated compound are preferably 1. to 3. below:
1. a compound in which a bonding hand of $Ar^1$ in a group represented by the formula (I) is bonded with a hydrogen atom or a halogen atom;
2. a compound comprising a repeating unit represented by the formula (II); and
3. a compound in which a group represented by the formula (I) is bonded to a repeating unit represented by the formula (II).

More preferred aspect of the conjugated compound is 1. and 2., particularly preferably 2.

The conjugated compound of the present invention can be used by doping a dopant in the conjugated compound. The dopant is used in a content of preferably 1 to 50 parts by weight relative to 100 parts by weight of the conjugated compound.

Examples of the dopant may include halogens, halogen compounds, Lewis acids, protonic acids, nitrile compounds, organic metal compounds, alkali metals and alkaline earth metals. Examples of the halogen may include chlorine, bromine and iodine, and examples of the halogen compound may include iodine chloride, iodine bromide and iodine fluoride. Examples of the Lewis acid may include phosphorus pentafluoride, arsenic pentafluoride, antimony pentafluoride, boron trifluoride, boron trichloride, boron tribromide and anhydrous sulfuric acid. Examples of the protonic acid may include: inorganic acids such as hydrochloric acid, sulfuric acid, nitric acid, phosphoric acid, fluoroboric acid, hydrofluoric acid and perchloric acid; and organic acids such as carboxylic acids and sulfonic acids. For the organic carboxylic acid, organic carboxylic acids containing one or more aliphatic, aromatic, or alicyclic carbonyl groups may be used. Examples thereof may include formic acid, acetic acid, oxalic acid, benzoic acid, phthalic acid, maleic acid, fumaric acid, malonic acid, tartaric acid, citric acid, lactic acid, succinic acid, monochloroacetic acid, dichloroacetic acid, trichloroacetic acid, trifluoroacetic acid, nitroacetic acid and triphenylacetic acid. For the organic sulfonic may acid, organic sulfonic acids containing one or more aliphatic, aromatic, or alicyclic sulfo groups may be used. Examples thereof may include: sulfonic acid compounds containing one sulfo group in the molecule thereof such as benzenesulfonic acid, p-toluenesulfonic acid, xylenesulfonic acid, naphthalenesulfonic acid, decylbenzenesulfonic acid, dodecylbenzenesulfonic acid, pentadecylbenzenesulfonic acid, methanesulfonic acid, ethanesulfonic acid, 1-propanesulfonic acid, 1-butanesulfonic acid, 1-hexanesulfonic acid, 1-heptanesulfonic acid, 1-octanesulfonic acid, 1-nonanesulfonic acid, 1-decanesulfonic acid, 1-dodecanesulfonic acid, vinylsulfonic acid, styrenesulfonic acid and allylsulfonic acid; and sulfonic acid compounds containing a plurality of sulfo groups in the molecule thereof such as ethanedisulfonic acid, butanedisulfonic acid, pentanedisulfonic acid, decanedisulfonic acid, benzenedisulfonic acid, naphthalenedisulfonic acid, toluenedisulfonic acid, dimethylbenzenedisulfonic acid, diethylbenzenedisulfonic acid, methylnaphthalenedisulfonic acid and ethylnaphthalenedisulfonic acid. For the dopant used in the present invention, the organic acid may be a polymer acid. Examples of the polymer acid may include polyvinylsulfonic acid, polystyrenesulfonic acid, sulfonated styrene-butadiene copolymer, polyallylsulfonic acid, polymethallylsulfonic acid, poly-2-acrylamide-2-methylpropanesulfonic acid and polyisoprenesulfonic acid. For the nitrile compound, compounds containing two or more cyano groups in a conjugated bond, and examples thereof may include tetracyanoethylene, tetracyanoethylene oxide, tetracyanobenzene, tetracyanoquinodimethane and tetracyanoazanaphthalene. Examples of the organic metal compound may include tris(4-bromophenyl)ammonium hexachloroantimonate, bis(dithiobenzyl)nickel, bis(tetrabutylammonium)bis(1,3-dithiol-2-thion-4,5-dithiolato) zinc complex, and tetrabutylammonium bis(1,3-dithiol-2-thion-4,5-dithiolato) nickel(III) complex. Examples of the alkali metal may include Li, Na, K, Rb and Cs, and examples of the alkaline earth metal may include Be, Mg, Ca, Sr and Ba.

In the metallic composite of the present invention, an adsorbed conjugated compound can be detected by performing an analysis such as a spectroscopic analysis, a thermal analysis, a mass analysis and an elemental analysis.

Examples of the spectroscopic analysis in the present invention may include a nuclear magnetic resonance spectrometry, an infrared spectrophotometry, a Raman spectrophotometry, an atomic absorption spectrophotometry, an arc discharge emission spectrometry, a spark optical emission spectrometry, an inductively coupled plasma emission spectrometry, an X-ray photoelectron spectrometry, a fluorescent X-ray spectrometry, an ultraviolet-visible spectrophotometry and a fluorescence spectrometry. Examples of the thermal analysis may include a thermogravimetry, a differential thermal analysis and a differential scanning calorimetry. By the mass spectrometry such as a mass spectrometry using various ionization methods and an elemental analysis, an adsorbed conjugated compound can be detected.

In the metallic composite of the present invention, it is preferred that a peak position measured by the X-ray photoelectron spectrometry for one or more atoms existing in the composite is detected at a peak position attributed to the conjugated compound as well as at a peak position of atoms existing in the metallic nanostructure and a precursor of metallic nanostructure, on a basis of a peak position of Ag3d.

The metallic composite to be subjected to the measurement by the X-ray photoelectron spectrometry is washed with various solvents capable of dissolving a conjugated compound having a molecular weight of 200 or more to which the metallic composite is adsorbed and various solvents capable of dissolving a compound adsorbed to the metallic nanostructure by five or more times to be used.

The washing can be performed by adding various solvents to the metallic composite, followed by stirring, shaking, ultrasonic dispersion, centrifugation, decantation, re-dispersion, dialysis, filtration, heating, and the like.

The conjugated compound used for the present invention has a highest occupied molecular orbital (HOMO) level measured by a photoelectron spectrometer in the atmosphere of usually −4.5 eV or less, preferably −4.8 eV or less, more preferably −5.0 eV or less, further preferably −5.2 eV or less, most preferably −5.3 eV or less.

The highest occupied molecular orbital is a value obtained by attaching "− (minus)" to a value of an ionization potential of the conjugated compound measured by a photoelectron spectrometer in the atmosphere.

The conjugated compound used for the present invention has a lowest unoccupied molecular orbital (LUMO) level of usually −3.5 eV or more, preferably −3.2 eV or more, more preferably −2.9 eV or more, further preferably −2.8 eV or more, most preferably −2.7 eV or more.

The lowest unoccupied molecular orbital can be obtained by adding a level difference (eV) between the highest occupied molecular orbital and the lowest unoccupied molecular orbital, that can be obtained from a value at an absorption edge in a longer wavelength side of an absorption spectrum measured by an ultraviolet-visible-near-infrared spectrophotometer, to a value of the highest occupied molecular orbital (eV).

The metallic composite of the present invention is manufactured, for example, by a method including a step of mixing a metallic nanostructure having an aspect ratio of 1.5 or more with a conjugated compound having a molecular weight of 200 or more in a solvent (hereinafter referred to as "mixing step").

The metallic composite of the present invention can also be manufactured by producing a metallic nanostructure in the presence of a conjugated compound.

As the metallic nanostructure for manufacturing the metallic composite of the present invention, a metallic nanostructure having a high purity may be used, or a metallic nanostructure to which an inorganic porous material, a polyacrylamide, a polyvinylpyrrolidone, a polyacrylic acid, or the like is adsorbed may be used. In the latter case, these compounds may be replaced by a conjugated compound.

The solvent used for manufacturing the metallic composite of the present invention is usually a solvent capable of dissolving a conjugated compound and not dissolving a metallic nanostructure. Specific examples of the solvent may include methanol, ethanol, benzyl alcohol, acetone, methyl ethyl ketone, dimethylformamide, dimethylsulfoxide, ethyl acetate, toluene, xylene, ortho-dichlorobenzene, chloroform, tetrahydrofuran, hexane, benzene, diethyl ether, acetonitrile, acetic acid, water, propanol, butanol and N-methylpyrrolidone. Among them, from the viewpoint of the solubility of the conjugated compound therein, methanol, ethanol, benzyl alcohol, acetone, methyl ethyl ketone, dimethylformamide, dimethylsulfoxide, ethyl acetate, toluene, xylene, chloroform, tetrahydrofuran, benzene, acetonitrile, propanol, butanol and N-methylpyrrolidone are preferred. The solvent may be used alone or in combination of two or more types thereof.

In the manufacturing method of the present invention, the mixing step is performed preferably by stirring, shaking, mechanically mixing, or a combination thereof.

Examples of the mechanical mixing applicable to the mixing step may include methods using a generally used mixing-stirring apparatus, ultrasonic distributor, ultrasonic washer, and the like. For the mixing-stirring apparatus, an apparatus in any type of pressure-type, shearing-type, ultrasonic-type, beads-type, rotor-type, and the like, may be used.

In the manufacturing method of the present invention, the concentration of the metallic nanostructure in a solvent during the mixing step is, from the viewpoints of the solubility of the conjugated compound and the dispersibility of the metallic nanostructure, preferably 0.0001 to 75% by weight, more preferably 0.001 to 50% by weight, further preferably 0.005 to 30% by weight, the most preferably 0.005 to 10% by weight.

The concentration of the conjugated compound in a solvent during the mixing step is, from the viewpoints of the solubility of the conjugated compound and the dispersibility of the metallic nanostructure, preferably 0.0001 to 75% by weight, more preferably 0.001 to 50% by weight, further preferably 0.05 to 30% by weight, the most preferably 0.05 to 10% by weight.

The temperature for the mixing step is, from the viewpoints of the solubility and the temperature stability of the conjugated compound, preferably −78 to 200° C., more preferably 0 to 100° C., further preferably 10 to 80° C., the most preferably 20 to 60° C.

The time for the mixing step is, from the viewpoint of affinity between the conjugated compound and the metallic nanostructure, preferably within 1,000 minutes, more preferably 1 to 1,000 minutes, further preferably 10 to 900 minutes, the most preferably 30 to 800 minutes. When a conjugated compound and a metallic nanostructure having a high affinity to each other are used, the time for the mixing step may be further shortened.

The manufacturing method of the present invention may comprise a step of purifying the metallic composite obtained in the mixing step (hereinafter referred to as "purification step"), after the mixing step. The purification step can be performed by ultrasonic dispersion, centrifugation, decantation, re-dispersion, dialysis, filtration, washing, heating, drying, and the like.

When the stability of the metallic nanostructure is sufficient, it is preferred that a step of adding a solvent, followed by ultrasonic dispersion, centrifugation and decantation is preferably repeated as the purification step.

When the stability of the metallic nanostructure is low, it is preferred that a step of adding a solvent, followed by filtration and/or dialysis is repeated as the purification step.

When the metallic composite is in a state of a dispersion liquid, the manufacturing method of the present invention may comprise a recovery step for obtaining the metallic composite in a solid state by means of centrifugation, filtration, evaporation, or the like after the mixing step.

In the mixing step and the purification step of the present invention, a dispersion stabilizer, a surfactant, a viscosity modifier, a corrosion inhibitor, and the like may be further added.

The metallic composite of the present invention as it is may be used for a material of an electrode or the like. The metallic composite may also be dispersed in a solvent to be used as a dispersion liquid. Specific examples of the solvent may include the same solvents as those used for the production of the metallic composite. The concentration of the metallic composite in the dispersion liquid is preferably 0.01 to 75% by weight, more preferably 0.05 to 50% by weight, further preferably 0.1 to 30% by weight. Besides the metallic composite of the present invention, this dispersion liquid may contain a dispersion stabilizer, a surfactant, a viscosity modifier, a corrosion inhibitor, and the like.

The dispersion liquid is useful as an electrically-conductive coating, a heat-conductive coating, an adhesive, a binder, and a functional coating material.

The composition of the present invention comprises the metallic composite and the conjugated compound having a molecular weight of 200 or more. The composition can be obtained by evaporating a solvent after the mixing step in the manufacturing method for the metallic composite, or by mixing the metallic composite with the conjugated compound.

The conjugated compound comprises preferably a hetero atom.

Examples of the hetero atom or the hetero atom-containing group that is contained in the conjugated compound may include a halogen atom, an optionally substituted hydrocarbyl group, a mercapto group, a mercaptocarbonyl group, a mercaptothiocarbonyl group, an optionally substituted hydrocarbylthio group, an optionally substituted hydrocarbylthiocarbonyl group, an optionally substituted hydrocarbyldithio group, a hydroxy group, an optionally substituted hydrocarbyloxy group, a carboxyl group, an aldehyde group, an optionally substituted hydrocarbylcarbonyl group, an optionally substituted hydrocarbyloxycarbonyl group, an optionally substituted hydrocarbylcarbonyloxy group, a cyano group, a nitro group, an amino group, an (optionally substituted hydrocarbyl)amino group, an optionally substituted dihydrocarbylamino group, a phosphino group, an (optionally substituted hydrocarbyl)phosphino group, an optionally substituted dihydrocarbylphosphino group, a group represented by formula: —OP(═O) (OH)$_2$, a phosphono group, a carbamoyl group, an (optionally substituted hydrocarbyl)carbamoyl group, an optionally substituted dihydrocarbylcarbamoyl group, a group represented by formula: —C(═S)NR$_2$, a group represented by formula: —B(OH)$_2$, a group represented by formula: —BR$_2$, a boric acid ester group, a group represented by formula: —Si (OR)$_3$, a sulfo group, an optionally substituted hydrocarbylsulfo group, an optionally substituted hydrocarbylsulfonyl group, a sulfino group, an optionally substituted hydrocarbylsulfino group, a group represented by formula: —NRC(═O)OR, a group represented by formula: —NRC(═O)SR, a group represented by formula: —NRC(═S)OR, a group represented by formula: —NRC(═S)SR, a group represented by formula: —OC(═O)NR$_2$, a group represented by formula: —SC(═O)NR$_2$, a group represented by formula: —OC(═S)NR$_2$, a group represented by formula: —SC(═S)NR$_2$, a group represented by formula: —NRC(═O) NR$_2$, a group represented by formula: —NRC(═S)NR$_2$, a heterocyclic group, a hydrocarbyl group having two or more ether bonds, a hydrocarbyl group having two or more ester bonds, a hydrocarbyl group having two or more amido bonds, a group represented by formula: —SM, a group represented by formula: —C(═O)SM, a group represented by formula: —CS$_2$M, a group represented by formula: —OM, a group represented by formula: —CO$_2$M, a group represented by formula: —NM$_2$, a group represented by formula: —NHM, a group represented by formula: —NRM, a group represented by formula: —PO$_3$M, a group represented by formula: —OP(═O) (OM)$_2$, a group represented by formula: —P(═O)(OM)$_2$, a group represented by formula: —C(═O)NM$_2$, a group represented by formula: —C(═O)NHM, a group represented by formula: —C(═O) NRM, a group represented by formula: —C(═S)NHM, a group represented by formula: —C(═S)NRM, a group represented by formula: —C(═S)NM$_2$, a group represented by formula: —B(OM)$_2$, a group represented by formula: —BR$_3$M, a group represented by formula: —B(OR)$_3$M, a group represented by formula: —SO$_3$M, a group represented by formula: —SO$_2$M, a group represented by formula: —NRC(═O)OM, a group represented by formula: —NRC (═O)SM, a group represented by formula: —NRC(═S) OM, a group represented by formula: —NRC(═S)SM, a group represented by formula: —OC(═O)NM$_2$, a group represented by formula: —OC(═O)NRM, a group represented by formula: —OC(═S)NM$_2$, a group represented by formula: —OC(═S)NRM, a group represented by formula: —SC(═O)NM$_2$, a group represented by formula: —SC (═O)NRM, a group represented by formula: —SC(═S) NM$_2$, a group represented by formula: —SC(═S)NRM, a group represented by formula: —NRC(═O)NM$_2$, a group represented by formula: —NRC(═O)NRM, a group represented by formula: —NRC(═S)NM$_2$, a group represented by formula: —NRC(═S)NRM, a group represented by formula: —NR$_3$M', a group represented by formula: —PR$_3$M', a group represented by formula: —OR$_2$M', a group represented by formula: —SR$_2$M', and a group represented by formula: —IRM', wherein R represents a hydrogen atom or an optionally substituted hydrocarbyl group, M represents a metal cation or an optionally substituted ammonium cation, and M' is an anion. Among them, a hydrocarbyl group having two or more ether bonds, a group represented by formula: —CO$_2$M, a group represented by formula: —SO$_3$M, and a group represented by formula: —NR$_3$M' are more preferred, a group represented by formula: —CO$_2$M and a group represented by formula: —NR$_3$M' are particularly preferred, and a group represented by formula: —CO$_2$M is the most preferred. Here, M and M' are the same as defined above.

The composition of the present invention comprises usually 1 to 99% by weight of the metallic composite and 1 to 99% by weight of the conjugated compound, preferably 1 to 50% by weight of the metallic composite and 49 to 99% by weight of the conjugated compound.

The composition of the present invention may comprise two or more types of metallic compositees and two or more types of conjugated compounds, and may further comprise a metal particle, a metal oxide, a metallic nanostructure, a surfactant, a viscosity modifier, a corrosion inhibitor, and the like.

The composition of the present invention is useful as an electrically-conductive coating, a heat-conductive coating, a wiring material, an adhesive, a binder, a functional coating material, an electromagnetic wave shielding material, a sensor, an antenna, an antistatic agent, a fiber, a packaging material, an antibacterial agent, a deodorant, a heating element, a radiator, and a medical material.

A thin film of the metallic composite or the composition of the present invention has electrical conductivity, and generally has light transmission property, and thus is useful as a flat liquid crystal display, a touch panel, a light-emitting device, a photoelectric conversion device, an antistatic layer, and an electromagnetic wave shielding layer. The thin film is formed on a substrate. The material for the substrate may be a material that is not chemically changed during the formation of the thin film, and examples of the material may include glass, plastic, silicon, and polymer film.

The conductivity of the thin film can be evaluated by the sheet resistance. The preferred value of the sheet resistance varies depending on the application. When the thin film is used for a material of a light-emitting device, the sheet resistance is preferably 10,000Ω/ or less, more preferably 1,000Ω/, and further preferably 100Ω/.

The light transmission properties of the thin film can be evaluated by the total light transmittance. Although the preferred value of the total light transmittance varies depending on the application, the total light transmittance is preferably 50% or more, more preferably 60% or more, further preferably 70% or more, and particularly preferably 80% or more. The total light transmittance means not the total light transmittance only of the thin film, but the total light transmittance of the thin film together with the substrate.

A material containing the metallic composite or the composition of the present invention is a material having electrical conductivity, and is useful for an electrically conductive material, an electrode material, an anode material, a cathode material and a wiring material and is more useful as a cathode material.

By using the metallic composite or the composition of the present invention for a layered structure, the metallic composite or the composition becomes a material useful for the production of an electronic device and the like. This layered structure comprises a substrate and a layer of the metallic composite and/or the composition of the present invention formed on the substrate. For instance, in a light-emitting device, the substrate is a glass substrate, polyethylene terephthalate, polyethylene, polypropylene, polycarbonate, or the like, and the layer of the metallic composite is an anode or a cathode.

The metallic composite and the composition of the present invention have a structure of high anisotropy, and therefore the metallic composite and the composition can secure a contact point even without paving them. The metallic composite and the composition of the present invention are excellent in electrical conductivity. Therefore, the metallic composite of the present invention can be used, for example, as an electrode material.

When the metallic composite or the composition of the present invention is used for an electrically conductive coating, a patterned electrically conductive site can be produced by selecting the application method as necessary, and therefore, an electrode or the like can be produced without requiring a process such as vapor deposition, sputtering, etching and plating. In addition, the metallic composite of the present invention has a structure of high anisotropy. Therefore, the thus obtained electrode has both of transparency and conductivity.

This electrode is applied to a flat liquid crystal display, a touch panel, a heating element, an electromagnetic wave shielding film, an antenna, an integrated circuit, an antistatic agent, and the like, besides an electronic device, e.g., a light-emitting device such as an organic electroluminescent (EL) device, a transistor, and a photoelectric conversion device such as a solar cell.

The organic transistor has a source electrode, a drain electrode and an insulated gate electrode layer, and the metallic composite or the composition thereof of the present invention is used for these electrodes. The organic transistor may further comprise a substrate and a semiconductor layer.

The photoelectric conversion device comprises electrodes composed of an anode and a cathode and an organic layer provided between the electrodes, and the metallic composite or the composition thereof of the present invention is used for these electrodes. The photoelectric conversion device may further comprise a substrate, a hole injection layer, an electron injection layer, a hole transport layer, an electron transport layer, an interlayer, a charge separation layer, and the like.

The light-emitting device comprises electrodes composed of an anode and a cathode and a light-emitting layer provided between the electrodes, and the metallic composite or the composition thereof of the present invention is applied to these electrodes. The light-emitting device may further comprise a substrate, a hole injection layer, an electron injection layer, a hole transport layer, an electron transport layer, an interlayer, and the like.

The light-emitting device using the metallic composite or the composition thereof of the present invention comprises electrodes composed of an anode and a cathode and an organic layer provided between the electrodes. The light-emitting device of the present invention may further comprise a substrate, a hole injection layer, an electron injection layer, a hole transport layer, an electron transport layer, an interlayer, a light-emitting layer, and the like.

The organic layer is preferably one or more layers selected from the group consisting of a light-emitting layer, a hole transport layer, a hole injection layer, an electron transport layer, an electron injection layer and an interlayer, and the organic layer is more preferably a light-emitting layer.

The light-emitting layer means a layer having a function of emitting light. The hole transport layer means a layer having a function of transporting holes. The electron transport layer means a layer having a function of transporting electrons. The interlayer exists adjacent to the light-emitting layer between the light-emitting layer and the anode, and means a layer having a role of isolating the light-emitting layer from the anode or isolating the light-emitting layer from the hole injection layer or the hole transport layer. The electron transport layer and the hole transport layer are generically referred to as a charge transport layer. The electron injection layer and the hole injection layer are generically referred to as a charge injection layer. The light-emitting layer, the hole transport layer, the hole injection layer, the electron transport layer, the electron injection layer and the interlayer may each be either a layer consisting of a single layer or a layer consisting of two or more layers.

When the organic layer is a light-emitting layer, the light-emitting layer may further comprise one or more selected from the group consisting of a hole transporting material, an electron transporting material, a light-emitting material, and an additive for lengthening the luminance half-life of the light-emitting device. The light-emitting material means a material exhibiting fluorescence and/or phosphorescence. For the hole transporting material, the electron transporting material and the light-emitting material, publicly known compounds having a low molecular weight, triplet emission complexes, and compounds having a high molecular weight can be used.

Examples of the compound having a high molecular weight may include a polymer and copolymer containing a repeating unit of a fluorenediyl group, a polymer and copolymer containing a repeating unit of an arylene group, a polymer and copolymer containing repeating units of an arylene group and a vinylene group, and a polymer and copolymer containing a repeating unit of a group represented by the formula (V).

Examples of the compound having a low molecular weight may include: naphthalene derivatives; anthracene and derivatives thereof; perylene and derivatives thereof; dyes such as polymethine dyes, xanthene dyes, coumarin dyes and cyanine dyes; metal complexes of 8-hydroxyquinoline and of derivatives of 8-hydroxyquinoline; aromatic amines; tetraphenylcyclopentadiene and derivatives thereof; and tetraphenylbutadiene and derivatives thereof.

Examples of the triplet emission complex may include: Ir(ppy)$_3$, Btp$_2$Ir(acac) and ADS066GE (trade name; commercially available from American Dye Source, Inc.) that contain iridium as a central metal; PtOEP containing platinum as a central metal; and Eu(TTA)$_3$-phen containing europium as a central metal.

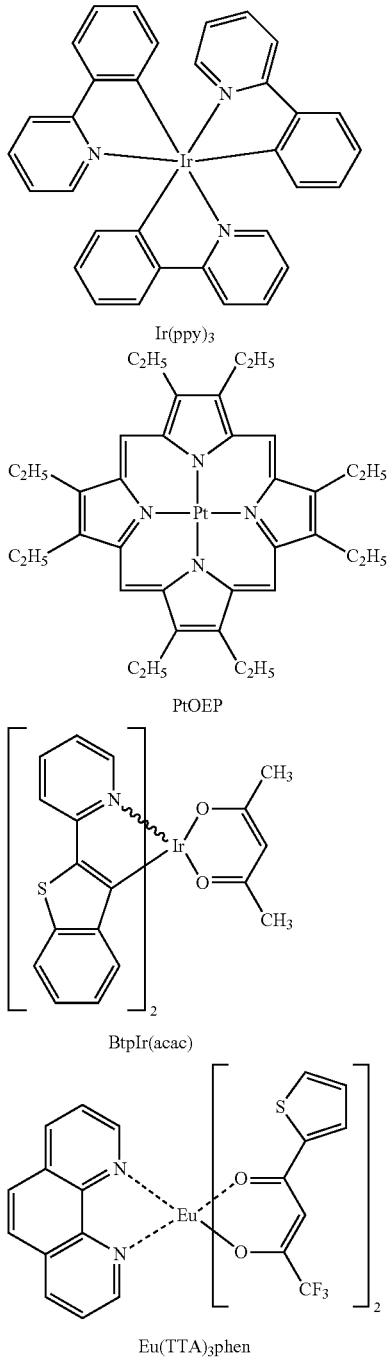

Ir(ppy)$_3$

PtOEP

BtpIr(acac)

Eu(TTA)$_3$phen

Examples of the additive may include: bipyridyl such as 2,2'-bipyridyl, 3,3'-bipyridyl and 4,4'-bipyridyl; and bipyridyl derivatives such as 4-methyl-2,2'-bipyridyl, 5-methyl-2,2'-bipyridyl and 5,5'-dimethyl-2,2'-bipyridyl.

Although the optimal value of the thickness of the light-emitting layer varies depending on the material used and may be selected so that the driving voltage and the luminous efficiency become an appropriate value, the thickness is usually 1 nm to 1 µm, preferably 2 nm to 500 nm, more preferably 5 nm to 200 nm, and further preferably 50 nm to 150 nm.

Examples of a method for forming the light-emitting layer may include methods by means of film formation from a solution. For the film formation from a solution, there can be used an application method such as a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method and a nozzle coating method.

Examples of the light-emitting device of the present invention may include a light-emitting device in which an electron transport layer is provided between a cathode and a light-emitting layer, a light-emitting device in which a hole transport layer is provided between an anode and a light-emitting layer, and a light-emitting device in which an electron transport layer is provided between a cathode and a light-emitting layer and a hole transport layer is provided between an anode and the light-emitting layer.

Examples of the structure of such light-emitting device may include structures of a) to d) below.
a) anode/light-emitting layer/cathode
b) anode/hole transport layer/light-emitting layer/cathode
c) anode/light-emitting layer/electron transport layer/cathode
d) anode/hole transport layer/light-emitting layer/electron transport layer/cathode
(wherein "/" indicates that each layer is adjacently stacked. The same shall apply hereinafter).

In each of these structures, an interlayer may be provided adjacent to the light-emitting layer between the light-emitting layer and the anode. Examples of the structure of such light-emitting device may include structures of a') to d') below.
a') anode/interlayer/light-emitting layer/cathode
b') anode/hole transport layer/interlayer/light-emitting layer/cathode
c') anode/interlayer/light-emitting layer/electron transport layer/cathode
d') anode/hole transport layer/interlayer/light-emitting layer/electron transport layer/cathode When the light-emitting device of the present invention has a hole transport layer, the hole transport layer usually contains the hole transporting material (compound of a high molecular weight or compound of a low molecular weight). Examples of the hole transporting material may include polyvinylcarbazole and derivatives thereof, polysilane and derivatives thereof, polysiloxane derivatives having an aromatic amine in the side chain or backbone thereof, pyrazoline derivatives, arylamine derivatives, stilbene derivatives, triphenyldiamine derivatives, polyaniline and derivatives thereof, polythiophene and derivatives thereof, polypyrrole and derivatives thereof, poly(p-phenylenevinylene) and derivatives thereof, and poly(2,5-thienylenevinylene) and derivatives thereof.

Among them, for the compound of a high molecular weight, preferred are polyvinylcarbazole and derivatives thereof, polysilane and derivatives thereof, polysiloxane derivatives having an aromatic amine compound group in the side chain or backbone thereof, polyaniline and derivatives thereof, polythiophene and derivatives thereof, poly(p-phenylenevinylene) and derivatives thereof, poly(2,5-thienylenevinylene) and derivatives thereof, and the like, and more preferred are polyvinylcarbazole and derivatives thereof, polysilane and derivatives thereof, and polysiloxane derivatives having an aromatic amine in the side chain or backbone thereof.

Among them, examples of the compound of a low molecular weight may include pyrazoline derivatives, arylamine derivatives, stilbene derivatives, and triphenyldiamine derivatives. These compounds of a low molecular weight are preferably dispersed in a polymer binder to be used.

For the polymer binder, a polymer binder that does not extremely inhibit the charge transportation and does not strongly absorb visible light is preferred. Examples of the polymer binder may include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, and polysiloxane.

Polyvinylcarbazole and derivatives thereof can be obtained, for example, from a vinyl monomer through cation polymerization or radical-polymerization.

Examples of the polysilane and derivatives thereof may include compounds disclosed in Chemical Review (Chem. Rev.), vol. 89, p. 1359 (1989) and British Patent No. GB2300196, Publication Specification. Although the synthesis method also can employ methods described in these documents, the Kipping method is particularly preferably used.

In a polysiloxane and derivatives thereof, the siloxane skeleton structure has little hole transporting property. Therefore, a polysiloxane and derivatives thereof having a structure of the hole transporting material of a low molecular weight in the side chain or backbone thereof are preferred, and a polysiloxane and derivatives thereof having a hole transporting aromatic amine in the side chain or backbone thereof are more preferred.

When using the compound of a low molecular weight, an example of a method for forming a film of the hole transport layer may include a method by means of film formation from a mixed solution with the polymer binder. When using the compound of a high molecular weight, an example of the method may include a method by means of film formation from a solution.

As the solvent used for the film formation from a solution, a solvent capable of dissolving or homogeneously dispersing the hole transporting material is preferred. Examples of the solvent may include: chlorinated hydrocarbon solvents such as chloroform, methylene chloride, 1,2-dichloroethane, 1,1, 2-trichloroethane, chlorobenzene and o-dichlorobenzene; ether solvents such as tetrahydrofuran and dioxane; aromatic hydrocarbon solvents such as toluene and xylene; aliphatic hydrocarbon solvents such as cyclohexane, methylcyclohexane, pentane, hexane, heptane, octane, nonane and decane; ketone solvents such as acetone, methyl ethyl ketone and cyclohexanone; ester solvents such as ethyl acetate, butyl acetate and ethylcellosolve acetate; polyhydric alcohols and derivatives thereof such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol; alcohol solvents such as methanol, ethanol, propanol, isopropanol and cyclohexanol; sulfoxide solvents such as dimethylsulfoxide; and amide solvents such as N-methyl-2-pyrrolidone and N,N-dimethylformamide. The solvent may be used alone or in combination of two or more types thereof.

For the film formation from a solution, there can be used an application method such as a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method and a nozzle coating method.

Although the optimal value of the thickness of the hole transport layer varies depending on the material used and may be selected so that the driving voltage and the luminous efficiency become an appropriate value, it is necessary a thickness where no pinhole is formed. However, when the thickness is too large, the driving voltage of the device becomes high, which is not preferred. Therefore, the thickness of the hole transport layer is usually 1 nm to 1 µm, preferably 2 nm to 500 nm, and more preferably 5 nm to 200 nm.

When the light-emitting device of the present invention has an electron transport layer, the electron transport layer usually contains the electron transporting material (compound of a high molecular weight or compound of a low molecular weight). For the electron transporting material, publicly known electron transporting materials can be used, and examples thereof may include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and of derivatives of 8-hydroxyquinoline, polyquinoline and derivatives thereof, polyquinoxaline and derivatives thereof, and polyfluorene and derivatives thereof.

When using the compound of a low molecular weight, examples of a method for forming a film of the electron transport layer may include a vacuum evaporation method from a powder and a method by means of film formation from a solution state or a molten state. When unsing the compound of a high molecular weight, examples of the method may include a method by means of film formation from a solution or a molten state. In the method by means of film formation from a solution or a molten state, the polymer binder may be used in combination.

As the solvent used for the film formation from a solution, a solvent capable of dissolving or homogeneously dispersing an electron transporting material and/or a polymer binder is preferred. Examples of the solvent may include: chlorinated hydrocarbon solvents such as chloroform, methylene chloride, 1,2-dichloroethane, 1,1,2-trichloroethane, chlorobenzene and o-dichlorobenzene; ether solvents such as tetrahydrofuran and dioxane; aromatic hydrocarbon solvents such as toluene and xylene; aliphatic hydrocarbon solvents such as cyclohexane, methylcyclohexane, pentane, hexane, heptane, octane, nonane and decane; ketone solvents such as acetone, methyl ethyl ketone and cyclohexanone; ester solvents such as ethyl acetate, butyl acetate and 2-ethoxyethyl acetate; polyhydric alcohols and derivatives thereof such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol; alcohol solvents such as methanol, ethanol, propanol, isopropyl alcohol and cyclohexanol; sulfoxide solvents such as dimethylsulfoxide; and amide solvents such as N-methyl-2-pyrrolidone and N,N-dimethylformamide. The solvent may be used alone or in combination of two or more types thereof.

For the film formation from a solution or a molten state, there can be used an application method such as a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method and a nozzle coating method.

Although the optimal value of the thickness of the electron transport layer varies depending on the material used and may be selected so that the driving voltage and the luminous efficiency become an appropriate value, it is necessary a thickness where no pinhole is formed. However, when the thickness is too large, the driving voltage of the device becomes high, which is not preferred. Accordingly, the thickness of the electron transport layer is usually 1 nm to 1 μm, and preferably 2 nm to 500 nm.

The hole injection layer and the electron injection layer are layers, among charge transport layers provided adjacent to electrodes, having a function of improving a charge injecting efficiency from the electrodes and an effect of lowering the driving voltage of the light-emitting device.

For enhancing the adhesion with the electrode or improving the charge injection from the electrode, the charge injection layer or an insulating layer (usually, 0.5 nm to 4.0 nm as an average thickness, and the same shall apply hereinafter) may be provided adjacent to the electrode. For enhancing the adhesion of an interface and preventing mixing at the interface, a thin buffer layer may also be interposed in an interface of the charge transport layer or the light-emitting layer.

The order and the number of the layers to be stacked and the thickness of each of the layers may be adjusted by taking into consideration the light-emitting efficiency and the device life.

Examples of the light-emitting device of the present invention in which a charge injection layer (electron injection layer or hole injection layer) is provided may include a light-emitting device in which a charge injection layer is provided adjacent to the cathode and a light-emitting device in which a charge injection layer is provided adjacent to the anode. Examples of the structure of such light-emitting device may include structures of e) to p) below.

e) anode/charge injection layer/light-emitting layer/cathode
f) anode/light-emitting layer/charge injection layer/cathode
g) anode/charge injection layer/light-emitting layer/charge injection layer/cathode
h) anode/charge injection layer/hole transport layer/light-emitting layer/cathode
i) anode/hole transport layer/light-emitting layer/charge injection layer/cathode
j) anode/charge injection layer/hole transport layer/light-emitting layer/charge injection layer/cathode
k) anode/charge injection layer/light-emitting layer/electron transport layer/cathode
l) anode/light-emitting layer/electron transport layer/charge injection layer/cathode
m) anode/charge injection layer/light-emitting layer/electron transport layer/charge injection layer/cathode
n) anode/charge injection layer/hole transport layer/light-emitting layer/electron transport layer/cathode
o) anode/hole transport layer/light-emitting layer/electron transport layer/charge injection layer/cathode
p) anode/charge injection layer/hole transport layer/light-emitting layer/electron transport layer/charge injection layer/cathode A structure in which an interlayer is provided adjacent to the light-emitting layer between the light-emitting layer and the anode in each of the above structures is also exemplified. In this case, the interlayer may also serve as the hole injection layer and/or the hole transport layer.

Examples of the charge injection layer may include a layer containing a conductive polymer, a layer that is provided between the anode and the hole transport layer and that contains a material having an ionization potential of a medium value between an ionization potential of an anode material and an ionization potential of a hole transporting material contained in the hole transport layer, and a layer that is provided between the cathode and the electron transport layer and that contains a material having an electron affinity of a medium value between an electron affinity of a cathode material and an electron affinity of an electron transporting material contained in the electron transport layer.

When the charge injection layer is a layer containing a conductive polymer, the electric conductivity of the conductive polymer is preferably $1 \times 10^{-5}$ to $1 \times 10^3$ S/cm.

The type of ions to be doped is an anion for the hole injection layer, and a cation for the electron injection layer. Examples of the anion may include a polystyrenesulfonic acid ion, an alkylbenzensulfonic acid ion and a camphorsulfonic acid ion, and examples of the cation may include a lithium ion, a sodium ion, a potassium ion and a tetrabutylammonium ion.

The material used for the charge injection layer may be appropriately selected in the relationship with an electrode material and a material of an adjacent layer, and examples of the material may include polyaniline and derivatives thereof, polythiophene and derivatives thereof, polypyrrole and derivatives thereof, polyphenylenevinylene and derivatives thereof, polythienylenevinylene and derivatives thereof, polyquinoline and derivatives thereof, polyquinoxaline and derivatives thereof, conductive polymers such as polymers containing an aromatic amine structure in the backbone or side chain thereof, metal phthalocyanines (such as copper phthalocyanine), and carbon.

Examples of the material for the insulating layer may include metal fluorides, metal oxides and organic insulating materials. Examples of the light-emitting device in which the insulating layer is provided may include a light-emitting device in which the insulating layer is provided adjacent to the cathode and a light-emitting device in which the insulating layer is provided adjacent to the anode.

Examples of the structure of such light-emitting device may include structures of q) to ab) below.

q) anode/insulating layer/light-emitting layer/cathode
r) anode/light-emitting layer/insulating layer/cathode
s) anode/insulating layer/light-emitting layer/insulating layer/cathode
t) anode/insulating layer/hole transport layer/light-emitting layer/cathode
u) anode/hole transport layer/light-emitting layer/insulating layer/cathode
v) anode/insulating layer/hole transport layer/light-emitting layer/insulating layer/cathode
w) anode/insulating layer/light-emitting layer/electron transport layer/cathode x) anode/light-emitting layer/electron transport layer/insulating layer/cathode
y) anode/insulating layer/light-emitting layer/electron transport layer/insulating layer/cathode
z) anode/insulating layer/hole transport layer/light-emitting layer/electron transport layer/cathode
aa) anode/hole transport layer/light-emitting layer/electron transport layer/insulating layer/cathode
ab) anode/insulating layer/hole transport layer/light-emitting layer/electron transport layer/insulating layer/cathode A structure in which an interlayer is provided adjacent to the light-emitting layer between the light-emitting layer and the anode in each of the above structures is also exemplified. In this case, the interlayer may also serve as the hole injection layer and/or the hole transport layer.

In the structure in which an interlayer is applied to the structures of a) to ab), the interlayer is preferably a layer that is provided between the anode and the light-emitting layer and that is constituted of a material having an ionization potential of a medium value between an ionization potential of the anode, the hole injection layer or the hole transport layer and an ionization potential of an aromatic compound constituting the light-emitting layer.

Examples of the material used for the interlayer may include aromatic compounds containing aromatic amines such as polyvinylcarbazole and derivatives thereof, polyarylene derivatives having an aromatic amine in the side chain or backbone thereof, arylamine derivatives, and triphenyldiamine derivatives.

When using a high molecular weight material, an example of a method for forming a film of the interlayer may include a method by means of film formation from a solution.

As the solvent used for film formation from the solution, a solvent capable of dissolving or homogeneously dispersing a material used for the interlayer is preferred. Examples of the solvent may include: chlorinated hydrocarbon solvents such as chloroform, methylene chloride, 1,2-dichloroethane, 1,1,2-trichloroethane, chlorobenzene and o-dichlorobenzene; ether solvents such as tetrahydrofuran and dioxane; aromatic hydrocarbon solvents such as toluene and xylene; aliphatic hydrocarbon solvents such as cyclohexane, methylcyclohexane, pentane, hexane, heptane, octane, nonane and decane; ketone solvents such as acetone, methyl ethyl ketone and cyclohexanone; ester solvents such as ethyl acetate, butyl acetate, and ethylcellosolve acetate; polyhydric alcohols and derivatives thereof such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol; alcohol solvents such as methanol, ethanol, propanol, isopropyl alcohol and cyclohexanol; sulfoxide solvents such as dimethylsulfoxide; and amide solvents such as N-methyl-2-pyrrolidone and N,N-dimethylformamide. The solvent may be used alone or in combination of two or more types thereof.

For the film formation from the solution, there can be used an application method such as a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method, and a nozzle coating method.

The optimal value of the thickness of the interlayer varies depending on the material used and may be selected so that the driving voltage and the luminous efficiency become an appropriate value, and the thickness is usually 1 nm to 1 µm, and preferably 2 nm to 500 nm.

When the interlayer is provided adjacent to the light-emitting layer, particularly when both layers are formed by an application method, the mixing of materials for two layers may adversely affect on the characteristics or the like of the device. When the light-emitting layer is formed by an application method after the interlayer is formed by an application method, as a method for reducing the mixing of materials for the two layers, there can be mentioned a method comprising forming the interlayer by an application method, heating the interlayer to make the interlayer insoluble to an organic solvent used for the preparation of the light-emitting layer, and forming the light-emitting layer. The temperature for the heating is usually 150° C. to 300° C. The time for the heating is usually 1 minute to 1 hour.

The substrate on which the light-emitting device of the present invention is formed may be any substrate so long as the substrate is not changed during the formation of the electrode and the organic layer, and examples thereof may include substrates formed of a glass, a plastic, a polymer film, silicon, and the like. When the substrate is opaque, the electrode provided opposite to the substrate is preferably transparent or translucent.

At least one of the anode and the cathode that is included in the light-emitting device of the present invention is usually transparent or translucent.

Examples of the anode material may include conductive metal oxide films and translucent metal thin films. Specific examples thereof may include; films (such as NESA) produced with using conductive compounds consisting of indium oxide, zinc oxide, tin oxide, composite materials thereof such as indium-tin-oxide (ITO) and indium-zinc-oxide, and the like; gold; platinum; silver; and copper.

Examples of a method for manufacturing the anode may include a vacuum evaporation method, a sputtering method, an ion plating method, and a plating method. As the anode, an organic transparent conductive film such as polyaniline and derivatives thereof and polythiophene and derivatives thereof may also be used. The anode may be in a layered structure of two or more layers.

Although the thickness of the anode can be appropriately selected taking into consideration the light transmission property and the electric conductivity, the thickness is usually 10 nm to 10 µm, and preferably 20 nm to 1 µm.

For facilitating the charge injection, a layer containing a phthalocyanine derivative, a conductive polymer, carbon, or the like and an insulating layer containing a metal oxide, a metal fluoride, an organic insulating material, or the like may also be provided on the anode.

For the cathode material, a material having a small work function is preferred, and examples thereof may include: metals such as lithium, sodium, potassium, rubidium, cesium, beryllium, magnesium, calcium, strontium, barium, aluminum, scandium, vanadium, zinc, yttrium, indium, cerium, samarium, europium, terbium and ytterbium; alloys of two or more types of these metals; alloys of one or more types of these metals with one or more types of gold, silver, platinum, copper, manganese, titanium, cobalt, nickel, tungsten and tin; and graphite and a graphite intercalation compound. Examples of the alloy may include a magnesium-silver alloy, a magnesium-indium alloy, a magnesium-aluminum alloy, an indium-silver alloy, a lithium-aluminum alloy, a lithium-magnesium alloy, a lithium-indium alloy, and a calcium-aluminum alloy. The cathode may be in a layered structure of two or more layers.

The thickness of the cathode may be appropriately adjusted taking into consideration the electric conductivity and the durability, and is usually 10 nm to 10 μm and preferably 20 nm to 1 μm.

Examples of a method for manufacturing the cathode may include a vacuum evaporation method, a sputtering method, and a lamination method in which a metal thin film is thermo-compressed. Between the cathode and an organic layer (that is, any layers containing the aromatic compound of the present invention), a layer containing a conductive polymer, or a layer containing a metal oxide, a metal fluoride or an organic insulating material may also be provided. Further, after the cathode is manufactured, a protecting layer for protecting the light-emitting device may also be attached.

Using the light-emitting device of the present invention, a display device can be produced. The display device comprises a light-emitting device as one pixel. The array of the pixel can be an array ordinarily adopted for a display device such as a television, and can be an aspect in which a large number of pixels are arrayed on a common substrate. In the display device, pixels arrayed on a substrate may be formed within a pixel region defined by a bank.

Although the metallic composite or the composition of the present invention can be applied to any of the hole injection layer, the hole transport layer, the interlayer, the electron injection layer, the electron injection layer, the anode and the cathode, the metallic composite or the composition of the present invention is applied to preferably the hole injection layer, the electron injection layer, the anode and the cathode, further preferably the electron injection layer, the anode and the cathode, and particularly preferably the cathode.

For film formation of the metallic composite or the composition of the present invention from a solution may include a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method, and a nozzle coating method.

Even for any application, the metallic composite or the composition of the present invention may be used alone or in combination of two or more types thereof.

The metallic composite or the composition of the present invention can be used as a coatable cathode material having light transmission properties and electron injecting/accepting properties. The metallic composite or the composition used as a cathode material has a total light transmittance of preferably 50% or more, more preferably 60% or more, further preferably 70% or more, and particularly preferably 80% or more. The electron injecting/accepting properties means a nature capable of donating electrons to a compound layered on the cathode material or a nature capable of accepting electrons from a compound layered on the cathode material.

The metallic composite or the composition of the present invention can be applied by a method such as a spin coating method, a casting method, a micro gravure coating method, a gravure coating method, a bar coating method, a roll coating method, a wire bar coating method, a dip coating method, a spray coating method, a screen printing method, a flexo printing method, an off-set printing method, an inkjet printing method, a capillary coating method and a nozzle coating method, to form the cathode.

Using the above cathode material, an electronic device, particularly a light-emitting device can be prepared.

For example, the light-emitting device is a light-emitting device having a light-emitting layer between the anode and the cathode in which the cathode has the above cathode material and a layer except for the anode is formed by an application method. The materials for the anode and the light-emitting layer are the same as described above.

The above cathode materials can also be applied to a photoelectric conversion device.

For example, the photoelectric conversion device is a photoelectric conversion device having a charge separation layer between the anode and the cathode in which the cathode has the above cathode material and a layer except for the anode is formed by an application method.

The conjugated compound of the present invention is a conjugated compound comprising one or more structures represented by the formula (III) below, and further comprising a repeating unit represented by the formula (II) below and/or a repeating unit represented by the formula (IV) below and/or a repeating unit represented by the formula (V) below.

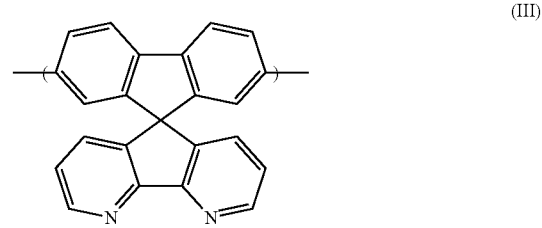

(III)

(IV)

(V)

wherein $Ar^3$, $Ar^4$ and $Ar^5$ represent a divalent aromatic group; Y represents a direct bond, an optionally substituted ethenylene group, an ethynylene group or an optionally substituted azomethine group; l is an integer of 0 to 2; and $R^3$ represents an optionally substituted hydrocarbyl group.

The divalent aromatic group is an atomic group remaining after removing two hydrogen atoms from an optionally substituted aromatic ring that is described above with respect to $Ar^1$ and $Ar^2$.

In the formula (IV), the azomethine group represented by Y means a divalent functional group having a structure of an azomethine bond, that is, a C=N structure. As the azomethine bond, a —CH=N— group is preferred.

In the formula (IV), Y is preferably an optionally substituted ethenylene group, and more preferably an unsubstituted ethenylene group.

In the formula (IV), Y is also preferably an ethynylene group.

In the formula (IV), l is preferably 0 or 2, and more preferably 0. However, when m is 0, $Ar^3$ is not a direct bond.

In the formula (V), the hydrocarbyl group represented by $R^3$ is the same as the hydrocarbyl group described above.

In the conjugated compound of the present invention, the content of the total of a repeating unit represented by the formula (II) and a structure represented by the formula (III) relative to 1 mol of a repeating unit represented by the formula (IV) is usually 0.01 mol to 1,000 mol, from the viewpoint of the dispersibility, preferably 0.1 mol to 1,000 mol, and more preferably 1 mol to 100 mol.

EXAMPLES

The present invention will now be described in detail by way of Examples and Comparative Examples.

<Analysis>

The weight average molecular weight (Mw) and the number average molecular weight (Mn) of a polymer were measured by a gel permeation chromatography (GPC) (manufactured by Tosoh Corporation; trade name: HLC-8220 GPC) as a polystyrene equivalent number average molecular weight and a polystyrene equivalent weight average molecular weight. The sample to be measured was dissolved in tetrahydrofuran so that the concentration of the sample became about 0.5% by weight and was injected into GPC in an amount of 50 μL. Furthermore, tetrahydrofuran was used as a mobile phase of GPC, and the mobile phase was flowed at a flow rate of 0.5 mL/min. The detection wavelength was set at 254 nm.

The structural analysis of a polymer was performed by $^1$H NMR analysis using a 300 MHz NMR spectrometer (manufactured by Varian, Inc). The measurement was performed by dissolving the sample in a deuterated solvent capable of dissolving the sample so that the concentration of the sample became 20 mg/mL.

Figure 2:
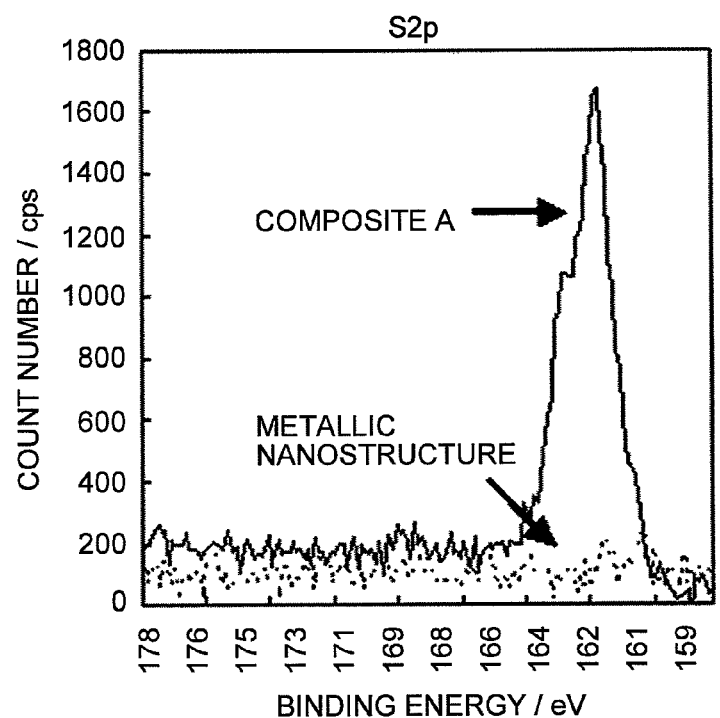
FIG. 2 shows S2p spectra measured by an X-ray photoelectron spectrometry for the composite A obtained in Example 1 and the silver nanostructure A obtained in Synthesis Example 1.
Figure 3:
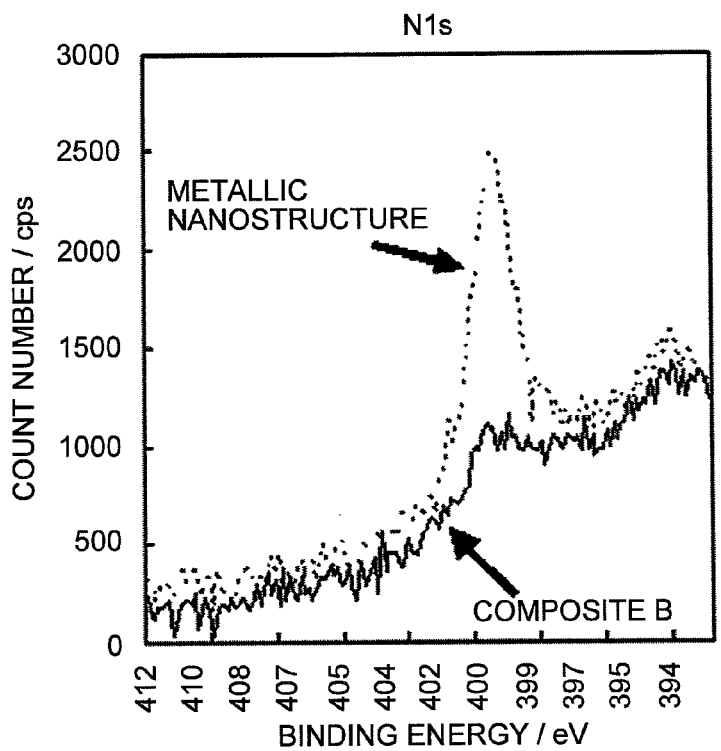
FIG. 3 shows N1s spectra measured by an X-ray photoelectron spectrometry for the composite B obtained in Example 2 and the silver nanostructure A obtained in Synthesis Example 1.
Figure 4:
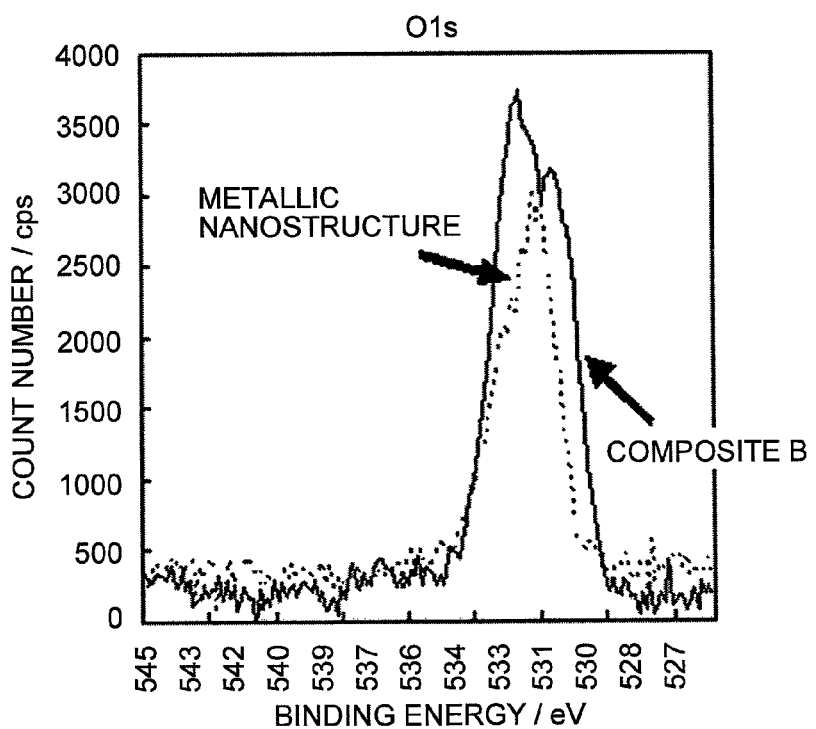
FIG. 4 shows O1s spectra measured by an X-ray photoelectron spectrometry for the composite B obtained in Example 2 and the silver nanostructure A obtained in Synthesis Example 1.
Figure 5:
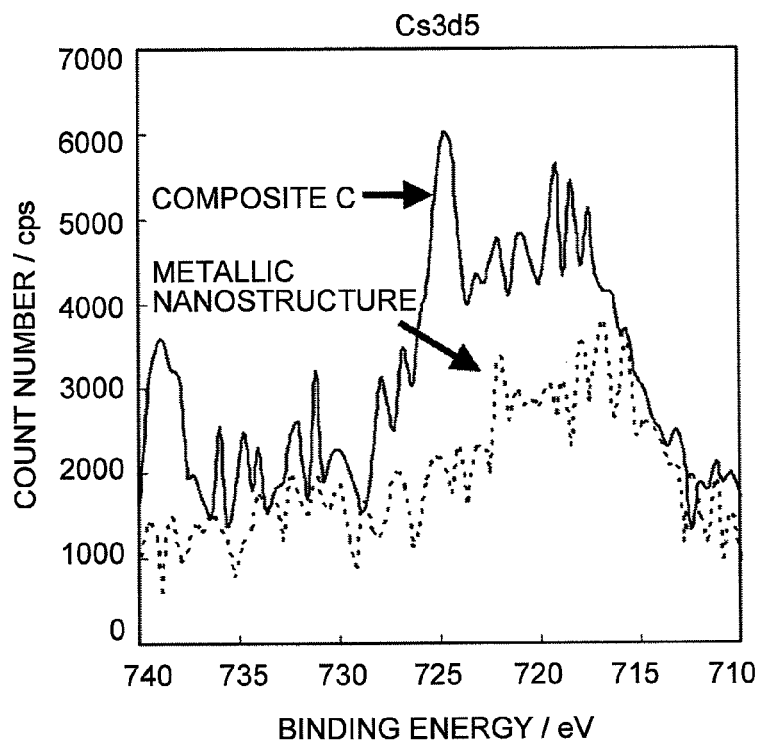
FIG. 5 shows Cs3d5 spectra measured by an X-ray photoelectron spectrometry for the composite C obtained in Example 3 and the silver nanostructure A obtained in Synthesis Example 1.
Figure 6:
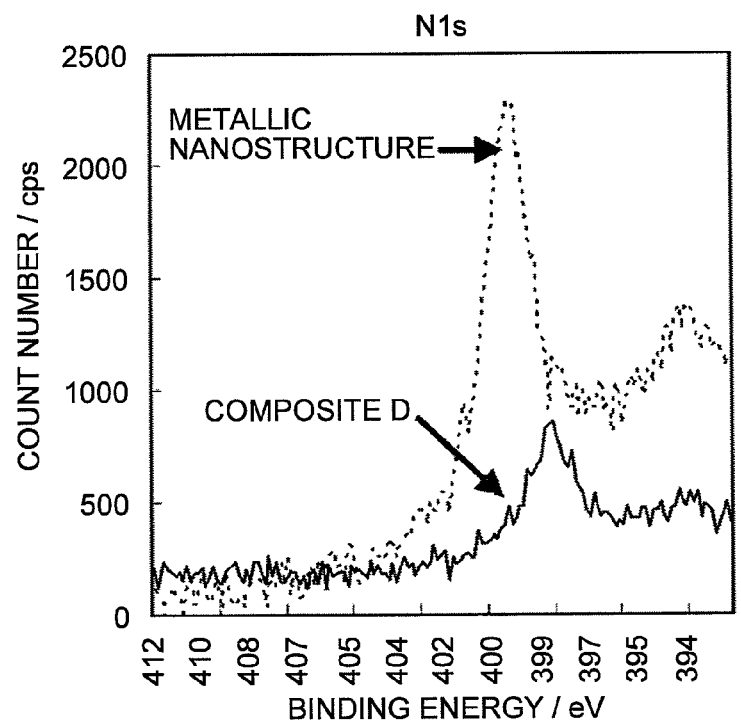
FIG. 6 shows N1s spectra measured by an X-ray photoelectron spectrometry for the composite D obtained in Example 4 and the silver nanostructure A obtained in Synthesis Example 1.
Figure 7:
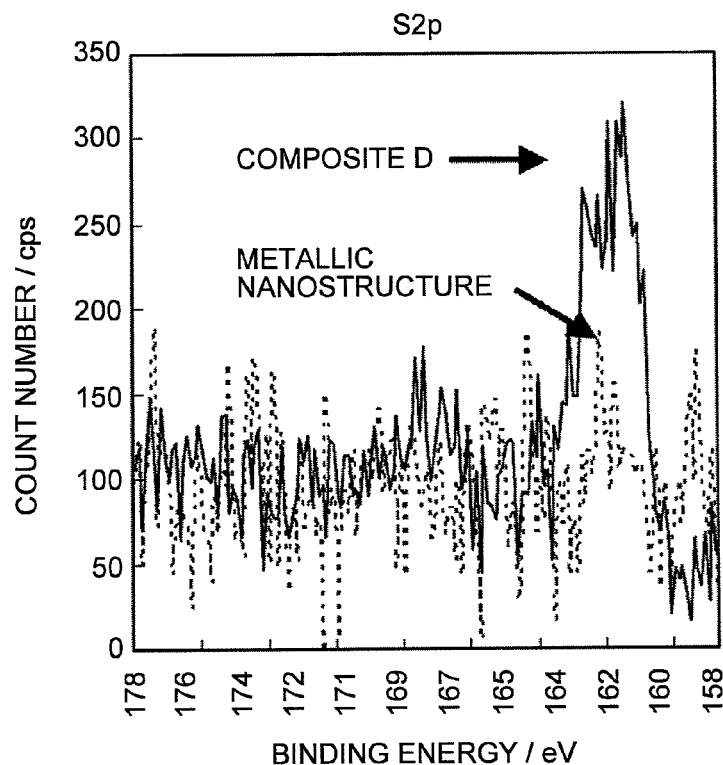
FIG. 7 shows S2p spectra measured by an X-ray photoelectron spectrometry of the composite D obtained in Example 4 and the silver nanostructure A obtained in Synthesis Example 1.
Figure 8:
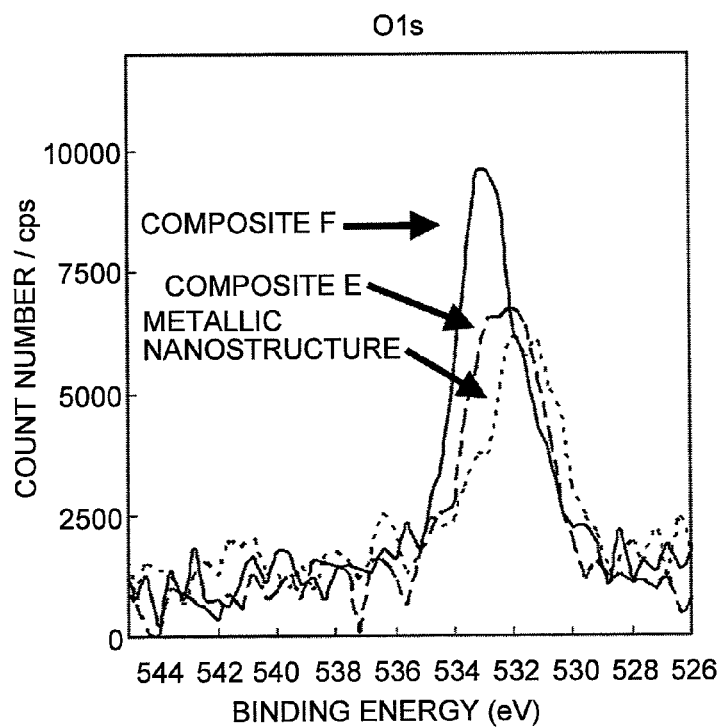
FIG. 8 shows O1s spectra measured by an X-ray photoelectron spectrometry for the composite E obtained in Example 6, the composite F obtained in Example 8, and the silver nanostructure A obtained in Synthesis Example 1.

An X-ray photoelectron spectrum of the composite prepared in Examples was measured by using a scanning X-ray photoelectron spectrometer (manufactured by Ulvac-Phi, Inc; trade name: Quantera SXM), thus performing a surface composition analysis. The analysis method was an X-ray photoelectron spectrometry (XPS) with an X-ray source of AlKα ray (1486.6 eV), a spot diameter of the X-ray of 100 μm, and a neutralization condition of a neutralization electron gun/low speed Ar ion gun. The sample was measured in a state where the sample was packed in a stainless-steel cup. The obtained results are shown in FIGS. 1 to 8.

A highest occupied molecular orbital (HOMO) level of a polymer was obtained from an ionization potential of the polymer, and a lowest unoccupied molecular orbital (LUMO) level was obtained from the ionization potential and the energy difference between the HOMO and the LUMO. For the measurement of the ionization potential, a photoelectron spectrometer (manufactured by Riken Keiki Co., Ltd.; AC-2) was used. The energy difference between the HOMO and the LUMO was obtained by measuring an absorption spectrum of the polymer using an ultraviolet-visible-near-infrared spectrophotometer (manufactured by Varian, Inc.: Cary SE) and from the absorption edge thereof.

The sheet resistance (Ω/) of the thin films prepared in Examples was measured using Loresta GP MCP T610 manufactured by Mitsubishi Chemical Corporation.

The total light transmittance (%) of the thin films prepared in Examples was measured using a direct-reading haze meter HGM-2DP manufactured by Suga Test Instruments Co., Ltd.

Synthesis Example 1

Synthesis of Silver Nanostructure A

A 50 mL flask containing 5 mL of ethylene glycol was immersed in an oil bath at 150° C., and the ethylene glycol was pre-heated while bubbling with air for 60 minutes. After the pre-heating, the air was exchanged with a nitrogen gas and bubbling was stopped. Next, 1.5 mL of a 0.1 M silver nitrate-ethylene glycol solution, 1.5 mL of a 0.15 M polyvinylpyrrolidone (hereinafter referred to as "PVP") (weight average molecular weight: 5.5×10$^4$)-ethylene glycol solution, and 40 μL of a 4 mM copper chloride dihydrate-ethylene glycol solution were added, and the resultant reaction mixture was stirred for 120 minutes, thus obtaining a dispersion liquid of a silver nanostructure. The obtained dispersion liquid was cooled down to 40° C. and then was subjected to centrifugation to obtain a precipitate. The obtained precipitate was dried, thus obtaining a silver nanostructure (hereinafter referred to as silver nanostructure A).

The obtained silver nanostructure A was subjected to visual observation with a photograph thereof by a SEM (manufactured by JEOL Ltd.; trade name: JSM-5500), and was found to have a wire shape, the shortest diameter of about 30 nm, and the longest diameter of about 15 μm. The average value of the aspect ratios for at least 10 or more silver nanostructures observed by the above method was about 500. It was confirmed by an XPS measurement that PVP coexisted during the synthesis was adsorbed to the silver nanostructure A.

Synthesis Example 2

Synthesis of Compound X

Into a reaction vessel, 10.4 g of magnesium and 120 mL of THF were charged, and then, 93.0 g of p-dibromobenzene and 160 mL of THF were dropped therein. The resultant solution is hereinafter referred to as "liquid mixture 1". Into another reaction vessel, 72.0 g of cyanuric chloride and 720 mL of toluene were charged and the resultant mixture was cooled down to 0° C., followed by dropping the liquid mixture 1 therein and stirring the mixture for 1 hour. An aqueous solution of ammonium chloride was added thereto, and then the resultant reaction mixture was subjected to a phase-separation with chloroform and the resultant organic layer was concentrated. The obtained crude product was purified by re-crystallization, thus obtaining 77.2 g of the compound A represented by the following formula:

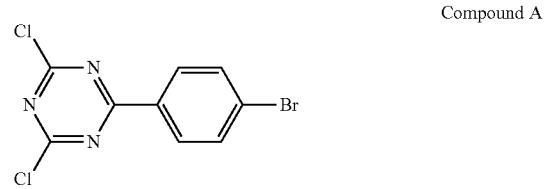 [SMILES: Clc1nc(Cl)nc(-c2ccc(Br)cc2)n1]

Compound A $^1$H-NMR (400 MHz, CDCl$_3$, room temperature)

δ 7.68 (2H), 8.38 (2H)

Into a reaction vessel, 15.0 g of the compound A, 188 mL of acetone, and 7.5 g of thiourea were charged and the resultant mixture was heated for 1 hour to reflux the mixture. The reaction mixture was cooled down to 0° C., and then, sodium carbonate was dropped therein and the reaction mixture was stirred. The resultant mixed solution was filtered, and hydrochloric acid was added to the filtrate to make the filtrate acidic. The precipitate was filtered to obtain a crude product. This crude product was purified by column chromatography, thus obtaining 6.8 g of the compound X represented by the following formula:

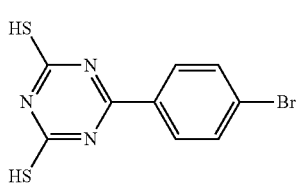

Compound X $^1$H-NMR (400 MHz, DMSO-$d_6$, room temperature) δ 3.17 (1H), 7.78 (2H), 8.05 (2H), 13.87 (1H)<

Synthesis Example 3

Synthesis of Compound Y

Into a 50 mL flask, 1.00 g (1.89 mmol) of the compound

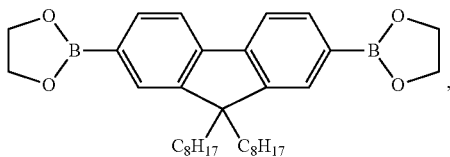

represented by the following formula:
1.15 g (1.89 mmol) of the compound represented by the following formula:

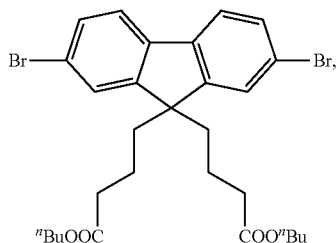

0.03 g of triphenylphosphine palladium, and 0.20 g of trioctylmethylammonium chloride (trade name: Aliquat (registered trade mark) 336, manufactured by Sigma-Aldrich Corporation) were charged, and was purged with an argon gas. Thereto, 20 mL of toluene was charged and the resultant mixture was heated to 105° C. Into the resultant reaction solution, a 2 M aqueous solution of sodium hydrogen carbonate (5 mL) was dropped to reflux the reaction mixture for 4 hours. The resultant solution was cooled down to room temperature, and was dropped into 120 mL of methanol and the resultant reaction mixture was stirred for 1 hour. Then, the deposited precipitate was filtered, dried under reduced pressure for 2 hours, and dissolved in 20 mL of tetrahydrofuran. The solution thus obtained was dropped into 120 mL of acetone and the resultant mixture was stirred for 30 minutes, followed by filtering the deposited precipitate and drying the precipitate under reduced pressure for 20 hours, thus obtaining 300 mg of the compound B (macromolecular compound) containing a repeating unit represented by the following formula:

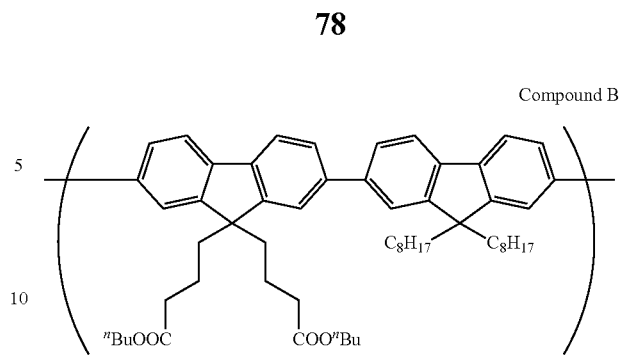

Compound B as a solid. The polystyrene equivalent number average molecular weight of the compound B was $3.5 \times 10^4$.

200 mg of the compound B was charged into a 100 mL flask and the inside of the flask was purged with nitrogen. Thereto, 20 mL of tetrahydrofuran and 5 mL of ethanol were added and the temperature of the resultant mixture was elevated to 55° C. Thereto, an aqueous solution in which 120 mg of sodium hydroxide was dissolved in 1 mL of water was added and the resultant mixture was stirred at 55° C. for 3 hours. The resultant mixture was cooled down to room temperature, and then, a reaction solvent was distilled off under reduced pressure to generate a solid. This solid was washed with water and was dried under reduced pressure, thus obtaining 90 mg of the compound C (macromolecular compound) containing a repeating unit represented by the formula:

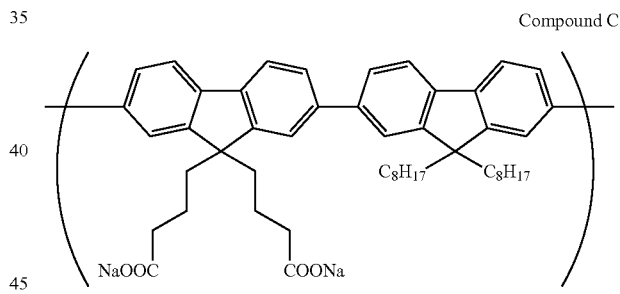

Compound C as a light yellow solid. By the NMR spectrum thereof, it was confirmed that a signal attributed to a butyl group at a butyl ester moiety of the compound B completely disappeared. The polystyrene equivalent number average molecular weight of the compound C was $3.5 \times 10^4$.

Into a 50 mL flask, 90 mg of the compound C was charged and the inside of the flask was purged with nitrogen. Thereto, 10 mL of tetrahydrofuran and 10 mL of ethanol were added and the temperature of the resultant mixture was elevated to 50° C. Thereto, 5 mL of a 1N hydrochloric acid was added and the resultant reaction mixture was stirred at 50° C. for 3 hours. The resultant mixture was cooled down to room temperature, and then, a reaction solvent was distilled off to generate a solid. This solid was washed with water and dried under reduced pressure, thus obtaining 80 mg of the compound Y (macromolecular compound) containing a repeating unit represented by the following formula:

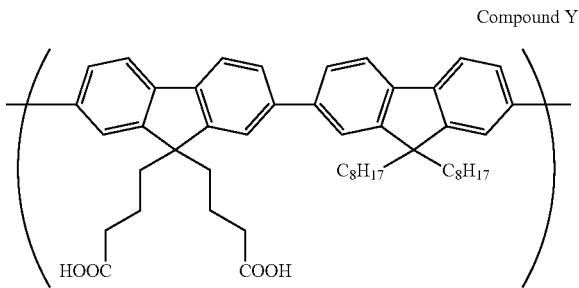

Compound Y as a white solid. The polystyrene equivalent number average molecular weight of the compound Y was $3.5 \times 10^4$.

Example 1

Synthesis of Composite A

Forty milligrams of the silver nanostructure A was added to 20 mL (0.01 M) of an ethanol solution of the compound X and the silver nanostructure A was dispersed by ultrasonic. The resultant mixture was stirred for 2 hours and was subjected to centrifugation to remove the supernatant. To the resultant residue, 20 mL (0.01 M) of an ethanol solution of the compound X was added and the resultant mixture was subjected to a set of operations of dispersing by ultrasonic, stirring for 2 hours, centrifugation, and removal of supernatant five times repeatedly. Then, 20 mL of ethanol was added thereto and the mixture was subjected to dispersing by ultrasonic. Subsequently, the resultant mixture was stirred for 1 hour and then was subjected to centrifugation to remove the supernatant. To the resultant mixture, 20 mL of ethanol was added and the mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer, and as a result, a peak of a sulfur atom attributed to a mercapto group of the compound X was obtained, and from a reduction of a peak of a nitrogen atom attributed to PVP, it was confirmed that the obtained product was a composite in which the compound X was adsorbed to the silver nanostructure (hereinafter referred to as "composite A").

The composite A (40 mg) was added to each of 20 mL of toluene and 20 mL of xylene and was dispersed by ultrasonic to prepare each dispersion liquid. The dispersion liquid thus obtained was allowed to stand at room temperature for 60 minutes, and each dispersion liquid was not separated into two layers of a supernatant layer and a composite precipitate layer and maintained a good dispersion state.

Example 2

Synthesis of Composite B

To 20 mL of a mixed solution (240 μM based on a monomer of a carboxylic acid group-containing unit) of the compound Y in THF:xylene=1:1 (volume ratio), 40 mg of the silver nanostructure A was added and dispersed by ultrasonic. The resultant mixture was stirred for 2 hours and was subjected to centrifugation to remove the supernatant. To the resultant residue, 20 mL of a mixed solution (240 μM based on a monomer of a carboxylic acid group-containing unit) of the compound Y in THF:xylene=1:1 (volume ratio) was added, and the resultant mixture was subjected to a set of operations of dispersing by ultrasonic, stirring for 2 hours, centrifugation, and removal of supernatant five times repeatedly. Then, 20 mL of ethanol was added and the mixture was dispersed by ultrasonic. The resultant mixture was stirred for 1 hour and then was subjected to centrifugation to remove the supernatant. To the resultant mixture, 20 mL of ethanol was added and the reaction mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer, and as a result, a peak of an oxygen atom attributed to a carboxyl group of the compound Y was obtained, and from a reduction of a peak of a nitrogen atom attributed to PVP, it was confirmed that the obtained product was a composite in which the compound Y was adsorbed to a silver nanostructure (hereinafter referred to as "composite B").

The composite B (40 mg) was added to 20 mL of toluene and was dispersed by ultrasonic to prepare a dispersion liquid. The dispersion liquid thus obtained was allowed to stand at room temperature for 60 minutes, and the dispersion liquid was not separated into two layers of a supernatant layer and a composite precipitate layer and maintained a good dispersion state.

Comparative Example 1

The silver nanostructure A (40 mg) was added to each of 20 mL of toluene and 20 mL of xylene and was dispersed by ultrasonic to prepare each dispersion liquid. The dispersion liquid thus obtained was allowed to stand at room temperature for 60 minutes, and the dispersion liquid was separated into two layers of a supernatant layer and a composite precipitate layer.

Synthesis Example 4

Synthesis of Conjugated Compound P-1

Into a 300 mL flask, 2,7-dibromo-9-fluorenone (52.5 g), ethyl salicylate (154.8 g), and mercaptoacetic acid (1.4 g) were charged and the inside of the flask was purged with nitrogen. Methanesulfonic acid (630 mL) was added thereto and the resultant mixture was stirred at 75° C. over a night. The mixture was left to be cooled down and was charged into ice water and the resultant mixture was stirred for 1 hour. The resultant solid was filtered and was washed with heated acetonitrile. The washed solid was dissolved in acetone, and a solid was re-crystallized from the resultant acetone solution and was filtered. The obtained solid (62.7 g), 2-[2-(2-methoxyethoxy)ethoxy]-p-toluenesulfonate (86.3 g), potassium carbonate (62.6 g), and 18-crown-6 (7.2 g) were dissolved in N,N-dimethylformamide (DMF) (670 mL) and the resultant solution was transferred into a flask, followed by stirring the solution at 105° C. over a night. The resultant mixture was left to be cooled down to room temperature and was charged into ice water, and the resultant mixture was stirred for 1 hour. Chloroform (300 mL) was added to the resultant reaction liquid, and the resultant mixture was subjected to separation-extraction, followed by concentrating the solution, thus obtaining 2,7-dibromo-9,9- bis[3-ethoxycarbonyl-4-[2-[2-(2-methoxyethoxy)ethoxy]ethoxy]phenyl]-fluorene, the compound D (51.2 g).

Compound D

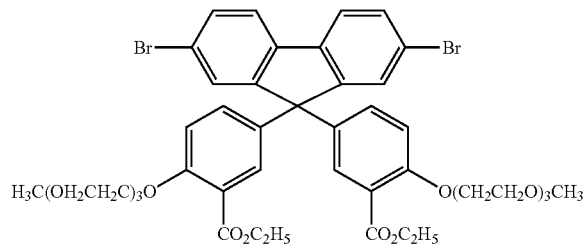

Under a nitrogen atmosphere, the compound D (15 g), bis(pinacolato)diboron (8.9 g), [1,1'-bis(diphenylphosphino)ferrocene]dichloropalladium (II) dichloromethane complex (0.8 g), 1,1'-bis(diphenylphosphino)ferrocene (0.5 g), potassium acetate (9.4 g), and dioxane (400 mL) were mixed, heated to 110° C., and subjected to heat-reflux for 10 hours. The reaction liquid was left to be cooled down and was filtered, and the filtrate was concentrated under reduced pressure. The resultant residue was washed with methanol three times and was dissolved in toluene, and activated carbon was added to the solution, followed by stirring the mixture. Then, the mixture was filtered and the filtrate was concentrated under reduced pressure, thus obtaining 2,7-bis (4,4,5,5-tetramethyl-1,3,2-dioxaborolan-2-yl)-9,9-bis[3-ethoxycarbonyl-4-[2-[2-(2-methoxyethoxy)ethoxy]ethoxy]phenyl]-fluorene, the compound E (11.7 g).

Compound E

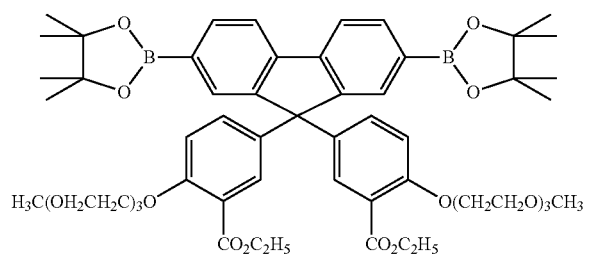

Under an inert atmosphere, the compound D (0.55 g), the compound E (0.61 g), triphenylphosphine palladium (0.01 g), Aliquat 336 (registered trade mark) (manufactured by Sigma-Aldrich Corporation) (0.20 g), and toluene (10 mL) were mixed and heated to 105° C. Into the reaction liquid, a 2 M aqueous solution of sodium carbonate (6 mL) was dropped and the resultant mixture was refluxed for 8 hours. To the reaction liquid, 4-tert-butylphenylboronic acid (0.01 g) was added and the resultant mixture was refluxed for 6 hours. Then, an aqueous solution of sodium diethyldithiocarbamate (10 mL, concentration: 0.05 g/mL) was added and was stirred for 2 hours. The mixed solution was dropped into 300 mL of methanol and the resultant mixture was stirred for 1 hour. The deposited precipitate was filtered, dried under reduced pressure for 2 hours, and was dissolved in 20 mL of tetrahydrofuran. The resultant solution was dropped into a solvent mixture of 120 mL of methanol and 50 mL of a 3% by weight acetic acid aqueous solution and the resultant mixture was stirred for 1 hour. The deposited precipitate was filtered and was dissolved in 20 mL of tetrahydrofuran. The solution thus obtained was dropped into 200 mL of methanol and the resultant mixture was stirred for 30 minutes. The deposited precipitate was filtered to obtain a solid. The obtained solid was dissolved in tetrahydrofuran and was purified by passing the resultant solution through an alumina column and a silica gel column. The tetrahydrofuran solution recovered from the column was concentrated and the concentrate was dropped into methanol (200 mL). The deposited solid was filtered and dried. The yield of the obtained poly[9,9-bis[3-ethoxycarbonyl-4-bis[2-[2-(2-methoxyethoxy)ethoxy]ethoxy]phenyl]-fluorene] (compound F) was 520 mg.

The polystyrene equivalent number average molecular weight of the compound F was $5.2 \times 10^4$. From the result of NMR, the compound F has a repeating unit represented by the following formula:

Compound F

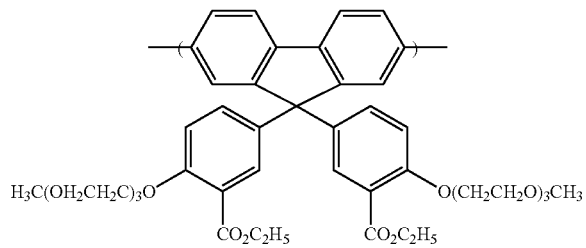

The compound F (200 mg) was charged into a 100 mL flask and the inside of the flask was purged with nitrogen. Thereto, tetrahydrofuran (20 mL) and ethanol (20 mL) were added and the temperature of the resultant mixture was elevated to 55° C. Thereto, an aqueous solution in which cesium hydroxide (200 mg) was dissolved in water (2 mL) was added and the resultant mixture was stirred at 55° C. for 6 hours. The resultant mixture was cooled down to room temperature and the reaction solvent was distilled off under reduced pressure. The resultant solid was washed with water and was dried under reduced pressure, thus obtaining a light yellow solid (150 mg). By the NMR spectrum thereof, it was confirmed that a signal attributed to an ethyl group at an ethyl ester moiety in the compound F completely disappeared. The obtained cesium salt of the compound F is called the conjugated compound P-1. The conjugated compound P-1 comprises a repeating unit represented by the formula below. An orbital energy of HOMO and an orbital energy of LUMO of the conjugated compound P-1 were −5.5 eV and −2.7 eV, respectively.

Conjugated compound P-1

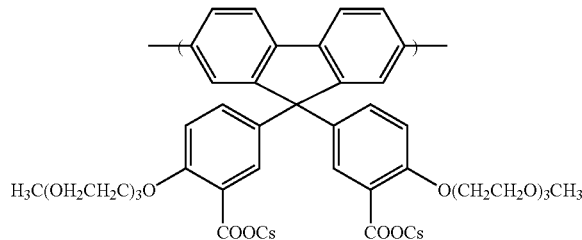

The polystyrene equivalent number average molecular weight of the conjugated compound P-1 was the same as that of the compound F.

Example 3

Synthesis of Composite C

To 10 mL of a methanol solution (100 μM based on a monomer of a repeating unit) of the conjugated compound P-1, 40 mg of the silver nanostructure A was added and was dispersed by ultrasonic. The resultant mixture was stirred for 2 hours and was subjected to centrifugation to remove the supernatant. To the resultant residue, 10 mL of a methanol solution (100 μM based on a monomer of a repeating unit) of the conjugated compound P-1 was added and the resultant mixture was subjected to a set of operations of dispersing by ultrasonic, stirring for 2 hours, centrifugation, and removal of supernatant five times repeatedly. Then, 20 mL of methanol was added thereto and the mixture was dispersed by ultrasonic. Then, the resultant mixture was stirred for 1 hour and was subjected to centrifugation to remove the supernatant. Thereto, 20 mL of methanol was added and the mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer. As a result, a peak of a cesium atom attributed to a Cs cation of the conjugated compound P-1 was obtained, and therefore it was confirmed that the obtained product was a composite in which the conjugated compound P-1 was adsorbed to a silver nanostructure (hereinafter referred to as "composite C").

Synthesis Example 5

Synthesis of Conjugated Compound P-2

Into a 50 mL flask, 100 mg (0.12 mmol) of a compound represented by the following formula:

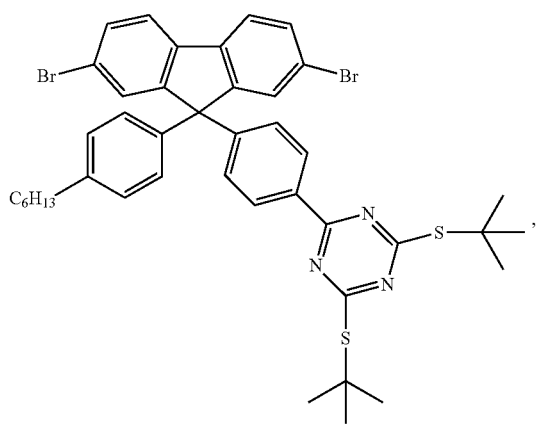

158 mg (0.24 mmol) of a compound represented by the following formula:

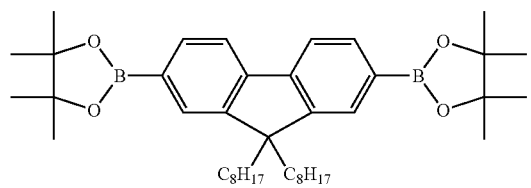

67.4 mg (0.12 mmol) of a compound represented by the following formula:

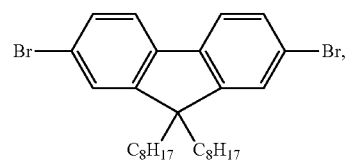

and 19.3 mg of Aliquat 336 (registered trade mark) (manufactured by Sigma-Aldrich Corporation) were charged and the inside of the flask was purged with an argon gas. Thereto, 8 mL of toluene was charged and the resultant mixture was stirred at 30° C. for 5 minutes. Then, 14.9 mg (0.048 mmol) of tetrakis(triphenylphosphine) palladium was added and the resultant mixture was stirred at 30° C. for 10 minutes. To the mixture, 4.0 mL of a 2 N aqueous solution of sodium carbonate was added and the resultant mixture was stirred at 30° C. for 5 minutes. The mixture was stirred at 100° C. for 8 hours. Then, the mixture was cooled down to room temperature, and an organic layer and an aqueous layer of the reaction solution were separated from each other. The organic layer was dropped into 200 mL of methanol to deposit a precipitate, and the precipitate was filtered and dried to obtain a yellow solid. The yellow solid was charged into a 300 mL flask and was dissolved in 100 mL of toluene, and the resultant solution was stirred at 30° C. for 5 minutes. Thereto, 10 g of activated carbon was added and the resultant mixture was stirred at 100° C. for 2 hours. Then, the mixture was cooled down to room temperature and an organic layer was filtered, followed by concentrating the filtrate to 5 mL. The concentrate was dropped into 200 mL of methanol to deposit a precipitate. The precipitate was filtered and dried, thus obtaining 100 mg of a compound G.

From the result of NMR, the compound G has a repeating unit represented by the following formula:

Compound G

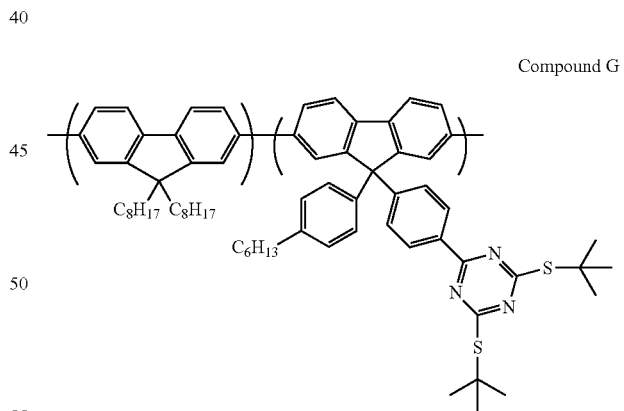

The polystyrene equivalent number average molecular weight Mn of the compound G was $7.9 \times 10^3$.

Into a 50 mL flask, 80 mg of the compound G and 20 mL of toluene were charged and the resultant mixture was stirred at room temperature for 10 minutes. Then, aluminum chloride was added and the resultant mixture was stirred further for 1 hour. An organic layer in the reaction vessel was dropped into 500 mL of methanol to deposit a precipitate. The precipitate was filtered and dried, thus obtaining 40 mg of a solid. From the result of NMR analysis thereof, it was confirmed that a signal attributed to a tert-butyl group of the compound G completely disappeared. The solid is considered to be a polymer having a repeating unit represented by the formula below. This polymer is called the conjugated compound P-2.

Conjugated compound P-2

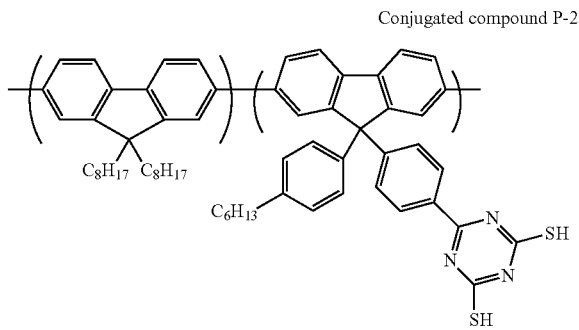

The polystyrene equivalent number average molecular weight of the conjugated compound P-2 is the same as that of the compound G.

Example 4

Synthesis of Composite D

To 20 mL of a xylene solution (175 μM based on a monomer of a mercapto group-containing unit) of the conjugated compound P-2, 40 mg of the silver nanostructure A was added and dispersed by ultrasonic. Then, the resultant mixture was stirred for 2 hours and was subjected to centrifugation to remove the supernatant. To the resultant residue, 20 mL of a xylene solution (175 μM based on a monomer of a mercapto group-containing unit) of the conjugated compound P-2 was added and the resultant mixture was subjected to a set of operations of dispersing by ultrasonic, stirring for 2 hours, centrifugation, and removal of supernatant five times repeatedly. Then, 20 mL of ethanol was added and the mixture was dispersed by ultrasonic. The resultant mixture was stirred for 1 hour and was subjected to centrifugation to remove the supernatant. To the resultant mixture, further 20 mL of ethanol was added and the mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer. As a result, a peak of a sulfur atom attributed to a mercapto group of the conjugated compound P-2 was obtained and from a reduction of a peak of a nitrogen atom attributed to PVP, it was confirmed that the obtained product was a composite in which the conjugated compound P-2 was adsorbed to a silver nanostructure (hereinafter referred to as "composite D").

The composite D (40 mg) was added to 20 mL of toluene and was dispersed by ultrasonic to prepare a dispersion liquid. The dispersion liquid thus obtained was allowed to stand at room temperature for 60 minutes, and the dispersion liquid was not separated into two layers of a supernatant layer and a composite precipitate layer and maintained a good dispersion state.

The obtained composite D was subjected to visual observation with a photograph thereof by an SEM and was found to have a wire shape, the shortest diameter of about 60 nm, and the longest diameter of about 2.9 μm. The average value of the aspect ratios for at least 10 silver nanostructures observed by the above method was about 48.

Example 5

Synthesis of Conjugated Compound P-3

The synthesis of (4,5-diaza-2',7'-dibromo, 9,9'-spirobifluorene (compound G)) represented by the formula below was performed in accordance with a method described in K.-T. Wong, R.-T. Chen, F.-C. Fang, C.-c. Wu, Y.-T. Lin, Organic Letters, vol. 7, p. 1979.

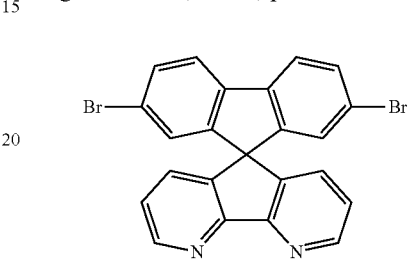

Into a 100 mL flask purged with an argon gas, 810 mg (3 mmol) of bis(1,5-cyclooctadiene) nickel, 469 mg (3 mmol) of 2,2'-bipyridyl, 325 mg (3 mmol) of 1,5-cyclooctadiene, 10 mL of toluene, and 10 mL of dimethylformamide were charged and dissolved. Thereto, a solution in which 850 mg (0.9 mmol) of the compound D and 48 mg (0.1 mmol) of the compound G were dissolved in 5 mL of toluene and 15 mL of dimethylformamide was added. The resultant reaction solution was stirred at 80° C. for 6 hours, and 16 mg (0.1 mmol) of bromobenzene was added thereto, followed by further stirring at 80° C. for 1 hour. The resultant reaction solution was cooled down to room temperature and was dropped into 300 mL of methanol, and the resultant mixture was stirred for 1 hour to deposit a solid. The solid was retrieved by filtration, was washed with hydrochloric acid, distilled water, ammonia water and distilled water, and was dried, thus obtaining 596 mg of the conjugated compound P-3.

From the result of NMR, it was found that the conjugated compound P-3 has repeating units represented by the formula below in 9:1 (molar ratio; theoretical value calculated from the charged raw material) in this order.

Conjugated compound P-3

The polystyrene equivalent number average molecular weight of the conjugated compound P-3 was $2.0 \times 10^4$.

Example 6

Synthesis of Composite E

To 20 mL of a benzyl alcohol solution (200 μM based on a monomer of a spirofluorene-containing unit) of the conjugated compound P-3, 40 mg of the silver nanostructure A was added and dispersed by ultrasonic. Then, the resultant mixture was stirred for 2 hours and was subjected to centrifugation to remove the supernatant. To the resultant residue, 20 mL of a benzyl alcohol solution (200 μM based on a monomer of a spirofluorene-containing unit) of the conjugated compound P-3 was added and the resultant mixture was subjected to a set of operations of dispersing by ultrasonic, stirring for 2 hours, centrifugation, and removal of supernatant five times repeatedly. Then, 20 mL of benzyl alcohol was added and the mixture was dispersed by ultrasonic. The resultant mixture was stirred for 1 hour and was subjected to centrifugation to remove the supernatant. To the resultant mixture, 20 mL of benzyl alcohol was added and the mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer. As a result, a peak of an oxygen atom attributed to the conjugated compound P-3 was obtained and the position for the peak was different from that for the peak attributed to PVP, so that it was confirmed that the obtained product was a composite in which the conjugated compound P-3 was adsorbed to a silver nanostructure (hereinafter referred to as "composite E").

The composite E (40 mg) was added to 20 mL of toluene and was dispersed by ultrasonic to prepare a dispersion liquid. The dispersion liquid thus obtained was allowed to stand at room temperature for 60 minutes, and the dispersion liquid was not separated into layers and maintained a good dispersion state.

The obtained composite E was subjected to visual observation with a photograph thereof by an SEM and was found to have a wire shape, the shortest diameter of about 40 nm, and the longest diameter of about 0.8 μm. The average value of the aspect ratios for at least 10 silver nanostructures observed by the above method was about 20.

Example 7

Synthesis of Conjugated Compound P-4

Into a flask under an argon atmosphere, the conjugated compound P-3 (100 mg) was charged and was dissolved in 20 mL of tetrahydrofuran and 2 mL of ethanol. To the resultant solution, 3 mL of an aqueous solution of cesium hydroxide 334 mg was added and the resultant mixture was stirred at 55° C. for 2 hours. To the resultant reaction solution, 5 mL of methanol was added and the resultant mixture was stirred while heating at 60° C. for 3 hours. Then, 3 mL of an aqueous solution of cesium hydroxide 334 mg was added and the resultant mixture was refluxed while heating at 65° C. for 2 hours. When the solvent of the resultant reaction solution was distilled off, a solid was deposited. The solid was washed with water, and then, the solid was retrieved by filtration and dried, thus obtaining 110 mg of a conjugated compound (hereinafter referred to as "conjugated compound P-4") having two types of repeating units represented by the following formula:

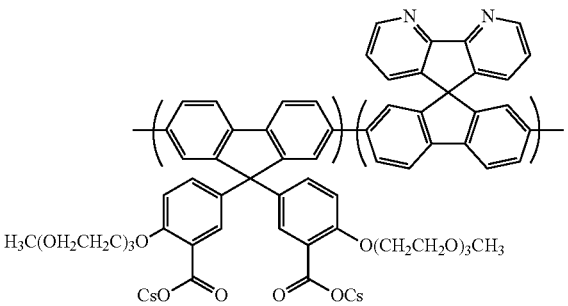

Conjugated compound P-4 in 9:1 (molar ratio; theoretical value calculated from the charged raw material) in this order. From the NMR spectrum thereof, it was confirmed that a signal attributed to an ethyl group at an ethyl ester moiety in the conjugated compound P-3 completely disappeared.

Example 8

Synthesis of Composite F

To 10 mL of a benzyl alcohol solution (100 μM based on a monomer of a spirofluorene-containing unit) of the conjugated compound P-4, 40 mg of the silver nanostructure A was added and dispersed by ultrasonic. Then, the resultant mixture was stirred for 2 hours and was subjected to centrifugation to remove the supernatant. To the resultant residue, 10 mL of a benzyl alcohol solution (100 μM based on a monomer of a spirofluorene-containing unit) of the conjugated compound P-4 was added and the resultant mixture was subjected to a set of operations of dispersing by ultrasonic, stirring for 2 hours, centrifugation, and removal of supernatant five times repeatedly. Then, 20 mL of benzyl alcohol was added and the mixture was dispersed by ultrasonic. The resultant mixture was stirred for 1 hour and was subjected to centrifugation to remove the supernatant. To the resultant mixture, 20 mL of benzyl alcohol was added and the mixture was subjected to a set of operations of dispersing by ultrasonic, stirring for 1 hour, centrifugation, and removal of supernatant five times repeatedly, followed by drying the resultant residue. With respect to the obtained solid, a substance adsorbed to the surface of the silver nanostructure was measured using an X-ray photoelectron spectrometer. As a result, a peak of an oxygen atom attributed to the conjugated compound P-4 was obtained and the position for the peak was different from that for the peak attributed to PVP, so that it was confirmed that the obtained product was a composite in which the conjugated compound P-4 was adsorbed to a silver nanostructure (hereinafter referred to as "composite F").

The composite F (40 mg) was added to 20 mL of toluene and was dispersed by ultrasonic to prepare a dispersion liquid. The dispersion liquid thus obtained was allowed to stand at room temperature for 60 minutes, and the dispersion liquid was not separated into layers and maintained a good dispersion state.

The obtained composite F was subjected to visual observation with a photograph thereof by an SEM and was found to have a wire shape, the shortest diameter of about 40 nm, and the longest diameter of about 0.7 μm. The average value of the aspect ratios for at least 10 silver nanostructures observed by the above method was about 18.

Example 9

Preparation of Thin Film j-1 of the Composition

About 1.0% by weight of the silver nanostructure A was mixed with about 0.2% by weight of the conjugated compound P-1 and about 98.8% by weight of methanol, and the resultant mixture was stirred for 1 hour to obtain a dispersion liquid. By this process, the composite C obtained in Example 3 was produced. The resultant dispersion liquid was applied onto a glass substrate by a casting method. The glass substrate on which a film was formed was heated in air at 130° C. for 15 minutes to evaporate the solvent, and then was cooled down to room temperature, thus obtaining a thin film j-1 having a thickness of about 1 µm. The measurement result of the sheet resistance for the obtained thin film is shown in Table 1.

Example 10

Preparation of Thin Film j-2 of the Composition

About 1.0% by weight of the silver nanostructure A was mixed with about 0.2% by weight of the conjugated compound P-4 and about 98.8% by weight of benzyl alcohol, and the resultant mixture was stirred for 1 hour to obtain a dispersion liquid. By this process, the composite F obtained in Example 8 was produced. The resultant dispersion liquid was applied onto a glass substrate by a casting method. The glass substrate on which a film was formed was heated in air at 200° C. for 15 minutes to evaporate the solvent, and then was cooled down to room temperature, thus obtaining a thin film j-2 having a thickness of about 1 µm. The measurement result of the sheet resistance for the obtained thin film is shown in Table 1.

Example 11

Preparation of Thin Film j-3 of the Composition

A thin film j-3 having a thickness of about 200 nm was prepared in the same manner as in Example 9, except that the casting method was changed to a spin coating method. The measurement results of the total light transmittance and the sheet resistance for the obtained thin film are shown in Table 1. The total light transmittance of the thin film j-3 was 84.3%.

Comparative Example 2

About 1.0% by weight of the silver nanostructure A was mixed with about 99.0% by weight of methanol, and the resultant mixture was stirred for 1 hour. The resultant solution was applied onto a glass substrate by a spin coating method. The glass substrate on which a film was formed was heated in air at 130° C. for 15 minutes to evaporate the solvent, and then was cooled down to room temperature, thus obtaining a thin film cj-1 having a thickness of about 200 nm. The measurement result of the sheet resistance for the obtained thin film cj-1 is shown in Table 1. The obtained thin film had low uniformity.

TABLE 1

| | Thin film | Conjugated compound in composition | Application method | Sheet resistance Ω/ |
|---|---|---|---|---|
| Example 9 | j-1 | conjugated compound P-1 | casting method | 52 |
| Example 10 | j-2 | conjugated compound P-4 | casting method | 50 |
| Example 11 | j-3 | conjugated compound P-1 | spin coating method | 35 |
| Comparative Example 2 | cj-1 | none | spin coating method | 3,000 |

Example 12

Preparation of Electroluminescent Device k-1

On ITO of a glass substrate having a film of ITO formed as an anode, 0.5 mL of poly(3,4-ethylenedioxythiophene)/polystyrenesulfonic acid (manufactured by H. C. Starck GmbH; PEDOT:PSS solution; trade name: CLEVIOS (registered trade mark) P VP Al 4083) as a solution of a hole injecting material was applied, and a hole injecting material layer was formed into a film by a spin coating method so that the layer had a thickness of 70 nm. The glass substrate on which the hole injecting material layer was thus formed was heated in air at 200° C. for 10 minutes to make the hole injection layer insoluble, and the substrate was allowed to cool down to room temperature, thus obtaining a glass substrate A having the hole injection layer formed thereon.

5.2 mg of a hole transporting material and 1 mL of xylene were mixed to prepare a composition for a hole transport layer having a content of the hole transporting material of 0.6% by weight. The hole transporting material was synthesized by the method below.

Into a 1 L three-neck round-bottom flask equipped with a reflux cooler and an overhead stirrer, 2,7-bis(1,3,2-dioxyborole)-9,9-di(1-octyl)fluorene (3.863 g, 7.283 mmol), N,N-di(p-bromophenyl)-N-(4-(butane-2-yl)phenyl)amine (3.177 g, 6.919 mmol), and di(4-bromophenyl)benzocyclobutaneamine (156.3 mg, 0.364 mmol) were charged. Then, trade name: Aliquat 336 (registered trade name) (manufactured by Sigma-Aldrich Corporation) (2.29 g) was added, and then 50 mL of toluene was added. A $PdCl_2(PPh_3)_2$ catalyst (4.9 mg) was added and the resultant mixture was stirred in an oil bath at 105° C. for 15 minutes. Thereto, an aqueous solution of sodium carbonate (2.0 M, 14 mL) was added and the resultant reaction product was stirred in an oil bath at 105° C. for 16.5 hours. Subsequently, phenylboronic acid (0.5 g) was added and the resultant reaction product was stirred for 7 hours. An aqueous layer was removed and an organic layer was washed with 50 mL of water. The organic layer was returned to the reaction flask, and 0.75 g of sodium diethyldithiocarbamate and 50 mL of water were added thereto. The resultant reaction product was stirred in an oil bath at 85° C. for 16 hours. An aqueous layer was removed and an organic layer was washed with 100 mL of water three times, followed by passing the organic layer through a column of silica gel and basic alumina. Then, an operation of precipitating a toluene solution containing the objective hole transporting material in methanol was repeated twice, and the resultant precipitate was vacuum-dried at 60° C., thus obtaining 4.2 g of a macromolecular compound, a hole transporting material. The polystyrene equivalent number average molecular weight of the hole transporting material was $4.4 \times 10^4$.

Next, the composition for a hole transport layer was applied by a spin coating method onto the glass substrate A having the hole injection layer formed thereon to form a coating film having a thickness of 25 nm. This glass substrate on which the coating film was formed was heated in a nitrogen atmosphere at 200° C. for 20 minutes to make the coating film insoluble, and then was allowed to cool down to room temperature, thus obtaining a glass substrate B having the hole transport layer formed thereon.

Subsequently, BP 361 (manufactured by SUMATION Co., Ltd.) (11.3 mg) that is a light-emitting material and 1 mL of xylene were mixed to prepare a composition for a light-emitting layer having the content of the light-emitting material of 1.3% by weight.

This composition for a light-emitting layer was applied by a spin coating method onto the glass substrate B having the hole transport layer formed thereon to form a coating film having a thickness of 80 nm. The substrate on which the coating film was formed was heated in a nitrogen atmosphere at 130° C. for 15 minutes to evaporate the solvent, and then was allowed to cool down to room temperature, thus obtaining a glass substrate C having the light-emitting layer formed thereon.

Then, on the glass substrate C having the light-emitting layer formed thereon, a thin film j-1 was prepared in the same manner as in Example 9, thus obtaining a layered structure m-1 in which the metallic composite of the present invention was formed. The thin film j-1 serves as a cathode.

The layered structure m-1 in which the cathode was formed was sealed with a sealing glass and a two liquid mixing-type epoxy resin in a nitrogen atmosphere, thus preparing an electroluminescent device k-1.

A forward voltage of 12 V was applied to the electroluminescent device k-1, and the luminance thereof was measured. The obtained result is shown in Table 2.

Example 13

Preparation of Electroluminescent Device k-2

An electroluminescent device k-2 was prepared in the same manner as in Example 12, except that the thin film j-3 prepared by a spin coating method was used instead of the thin film j-1 prepared by a casting method. The prepared electroluminescent device k-2 is a both side light-emitting device. A forward voltage of 12 V was applied to the electroluminescent device k-2, and the luminance thereof was measured. The obtained result is shown in Table 2.

Comparative Example 3

Preparation of Electroluminescent Device k-3

An electroluminescent device k-3 was prepared in the same manner as in Example 12, except that the thin film cj-1 prepared by a spin coating method was used instead of the thin film j-1 prepared by a casting method. Although a forward voltage of 12 V was applied to the electroluminescent device k-3, no luminescence was observed.

TABLE 2

| | EL device | Conjugated compound in composition | Application method | Luminance (cd/m$^2$) |
|---|---|---|---|---|
| Example 12 | k-1 | conjugated | casting | 172 |
| Example 13 | k-2 | compound P-1 conjugated compound P-1 | spin coating method | 463 |
| Comparative Example 3 | k-3 | none | spin coating method | (unmeasurable) |

<Evaluation>

The metallic composite of the present invention is excellent in dispersibility in a non-polar solvent, and as is apparent from Table 1, an electrode material produced with using the metallic composite or the composition of the present invention has a small sheet resistance and excellent conductivity in comparison with an electrode material not using the metallic composite or composition of the present invention. As is apparent from Table 2, an electroluminescent device produced with using the metallic composite or the composition of the present invention is excellent in luminance in comparison with an electroluminescent device not using the metallic composite or composition of the present invention. This is because a charge injection from the metallic composite or the composition of the present invention is excellent.

INDUSTRIAL APPLICABILITY

The metallic composite and the composition of the present invention are excellent in dispersibility in a non-polar solvent and therefore can be applied to an application method using a non-polar solvent, and are excellent in conductivity and charge injecting properties. Therefore, the metallic composite and the composition of the present invention are useful, for example, as a coating electrode, a transparent electrode, a conductive coating, a wiring material, an adhesive, a binder, an electrically conductive coating, a circuit, an integrated circuit, an electromagnetic wave shielding material, a sensor, an antenna, an antistatic agent, a fiber, a packaging material, an antibacterial agent, a deodorant, a heating element, a radiator, and a medical material. In addition, the layered structure of the present invention is excellent in conductivity and transparency in a layer produced with using the metallic composite, and therefore the layered structure is useful for an electronic device such as a light-emitting device, a solar cell and an organic transistor, particularly an electrode.

The invention claimed is:

1. A metallic composite in which a conjugated compound having a molecular weight of 200 or more is adsorbed to a metallic nanosheet, a metallic nanorod, or a metallic nanowire having an aspect ratio of 10 or more and a largest diameter of 2000 nm or more.

2. The metallic composite of claim 1, wherein the conjugated compound is an aromatic compound and the metallic nanosheet, the metallic nanorod, or the metallic nanowire is a metallic nanosheet, a metallic nanorod, or a metallic nanowire of a metal of Group 11 of the Periodic Table, respectively.

3. The metallic composite of claim 1, wherein the conjugated compound is an aromatic compound having a hetero atom-containing group and the metallic nanosheet, the metallic nanorod, or the metallic nanowire is a metallic nanosheet, a metallic nanorod, or a metallic nanowire of a metal of Group 11 of the Periodic Table, respectively.

4. The metallic composite of claim 3, wherein the hetero atom-containing group is a monovalent group selected from Group 1, wherein the groups of the Group 1 are a mercapto group, a mercaptocarbonyl group, a mercaptothiocarbonyl group, an optionally substituted hydrocarbylthio group, an optionally substituted hydrocarbylthiocarbonyl group, an optionally substituted hydrocarbyldithio group, a hydroxy group, an optionally substituted hydrocarbyloxy group, a carboxyl group, an optionally substituted hydrocarbylcarbonyl group, a cyano group, an amino group, an (optionally substituted hydrocarbyl)amino group, an (optionally substituted dihydrocarbyl)amino group, a phosphino group, an (optionally substituted hydrocarbyl)phosphino group, an (optionally substituted dihydrocarbyl)phosphino group, a group represented by formula: —P(=O)(OH)$_2$, a sulfo group, a heterocyclic group, a halogen atom, a formyl group, an optionally substituted hydrocarbyloxycarbonyl group, an optionally substituted hydrocarbylcarbonyloxy group, a nitro group, a group represented by formula: —OP(=O)(OH)$_2$, a phosphono group, a carbamoyl group, an optionally substituted hydrocarbylcarbamoyl group, an (optionally substituted dihydrocarbyl)carbamoyl group, a group represented by formula: —C(=S)NR$_2$, a group represented by formula: —B(OH)$_2$, a group represented by formula: —BR$_2$, a boric acid ester group, a group represented by formula: —Si(OR)$_3$, an optionally substituted hydrocarbylsulfo group, an optionally substituted hydrocarbylsulfonyl group, a sulfino group, an optionally substituted hydrocarbylsulfino group, a group represented by formula: —NRC(=O)OR, a group represented by formula: —NRC(=O)SR, a group represented by formula: —NRC(=S)OR, a group represented by formula:
—NRC(=S)SR, a group represented by formula: —OC(=O)NR$_2$, a group represented by formula: —SC(=O)NR$_2$, a group represented by formula: —OC(=S)NR$_2$, a group represented by formula: —SC(=S)NR$_2$, a group represented by formula:
—NRC(=O)NR$_2$, and a group represented by formula: —NRC(=S)NR$_2$, wherein R represents a hydrogen atom or an optionally substituted hydrocarbyl group.

5. The metallic composite of claim 3, wherein the hetero atom-containing group is a monovalent group selected from Group 2, wherein the groups of the Group 2 are a hydrocarbyl group having two or more ether bonds, a hydrocarbyl group having two or more ester bonds, a hydrocarbyl group having two or more amido bonds, a group represented by formula: —SM, a group represented by formula: —C(=O)SM, a group represented by formula: —CS$_2$M, a group represented by formula: —OM, a group represented by formula: —CO$_2$M, a group represented by formula: —NM$_2$, a group represented by formula: —NHM, a group represented by formula: —NRM, a group represented by formula: —PO$_3$M, a group represented by formula: —OP(=O)(OM)$_2$, a group represented by formula: —P(=O)(OM)$_2$, a group represented by formula: —C(=O)NM$_2$, a group represented by formula:
—C(=O)NHM, a group represented by formula: —C(=O)NRM, a group represented by formula: —C(=S)NHM, a group represented by formula: —C(=S)NRM, a group represented by formula: —C(=S)NM$_2$, a group represented by formula: —B(OM)$_2$, a group represented by formula: —BR$_3$M, a group represented by formula: —B(OR)$_3$M, a group represented by formula: —SO$_3$M, a group represented by formula: —SO$_2$M, a group represented by formula: —NRC(=O)OM, a group represented by formula:
—NRC(=O)SM, a group represented by formula: —NRC(=S)OM, a group represented by formula: —NRC(=S)SM, a group represented by formula: —OC(=O)NM$_2$, a group represented by formula: —OC(=O)NRM, a group represented by formula:
—OC(=S)NM$_2$, a group represented by formula: —OC(=S)NRM, a group represented by formula: —SC(=O)NM$_2$, a group represented by formula: —SC(=O)NRM, a group represented by formula: —SC(=S)NM$_2$, a group represented by formula:
—SC(=S)NRM, a group represented by formula: —NRC(=O)NM$_2$, a group represented by formula: —NRC(=O)NRM, a group represented by formula: —NRC(=S)NM$_2$, a group represented by formula: —NRC(=S)NRM, a group represented by formula:
—NR$_3$M', a group represented by formula: —PR$_3$M', a group represented by formula: —OR$_2$M', a group represented by formula: —SR$_2$M', a group represented by formula: —IRM', and a heterocyclic group having a cationized nitrogen atom within the heterocycle, wherein R represents a hydrogen atom or an optionally substituted hydrocarbyl group, M represents a metal cation or an optionally substituted ammonium cation, and M' represents an anion.

6. The metallic composite of claim 3, wherein the conjugated compound comprises at least one type of group in the Group 1 and at least one type of group in the Group 2.

7. The metallic composite of claim 1, wherein the conjugated compound comprises a group represented by the formula (I) below, or a repeating unit represented by the formula (II) below, or both of them:

wherein
Ar$^1$ is an (n$^1$+1) valent aromatic group,
R$^1$ is a direct bond or an (m$^1$+1) valent group,
X$^1$ is a hetero atom-containing group,
m$^1$ and n$^1$, which are the same as or different from each other, are an integer of 1 or more, and
when R$^1$, X$^1$ and m$^1$ are plurally present, they each may be the same as or different from each other;

wherein
Ar$^2$ is an (n$^2$+2) valent aromatic group,
R$^2$ is a direct bond or an (m$^2$+1) valent group,
X$^2$ is a hetero atom-containing group,
m$^2$ and n$^2$, which are the same as or different from each other, are an integer of 1 or more, and
when R$^2$, X$^2$ and m$^2$ are plurally present, they each may be the same as or different from each other.

8. The metallic composite of claim 7, wherein the (n$^1$+1) valent aromatic group represented by Ar$^1$ is a residue remaining after removing (n$^1$+1) hydrogen atoms on an aromatic ring of aromatic compounds of the formulae below, the (n$^2$+2) valent aromatic group represented by Ar$^2$ is a residue remaining after removing (n$^2$+2) hydrogen atoms on an aromatic ring of aromatic compounds of the formulae below, and the aromatic groups are optionally substituted.

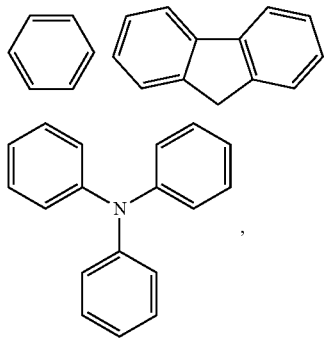

9. The metallic composite of claim 8, wherein the conjugated compound comprises at least one type of group in the Group 1 and at least one type of group in the Group 2.

10. The metallic composite of claim 1, wherein the conjugated compound is a macromolecular compound having a repeating unit represented by the following formulae:

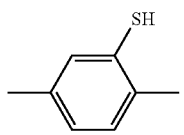 (a-1)

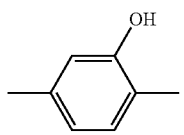 (a-2)

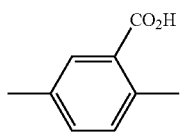 (a-3)

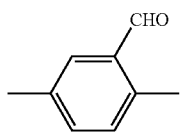 (a-4)

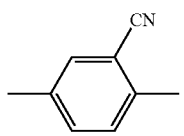 (a-5)

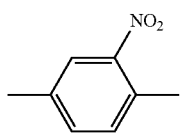 (a-6)

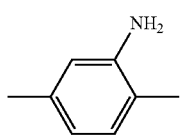 (a-7)

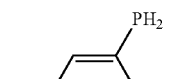 (a-8)

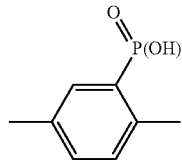 (a-9)

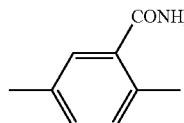 (a-10)

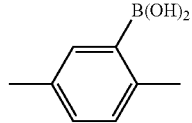 (a-11)

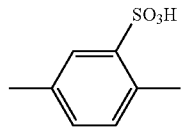 (a-12)

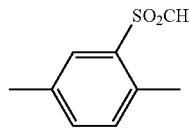 (a-13)

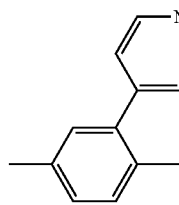 (a-14)

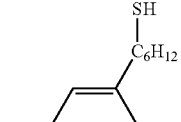 (a-15)

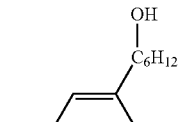 (a-16)

(a-17)

-continued
(a-18)
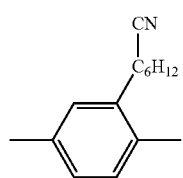
(a-19)
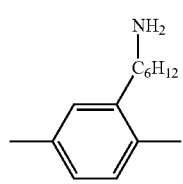
(a-20)
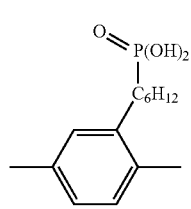
(a-21)
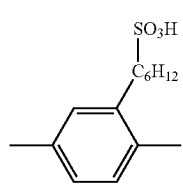
(a-22)
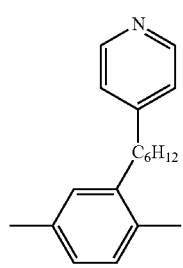
(a-23)
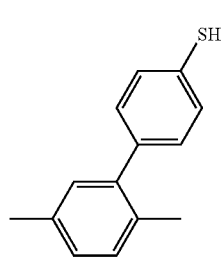
(a-24)
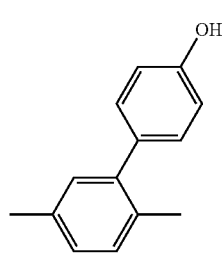
-continued
(a-25)
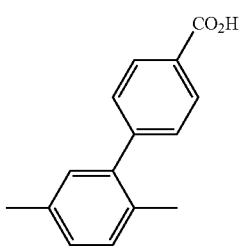
(a-26)
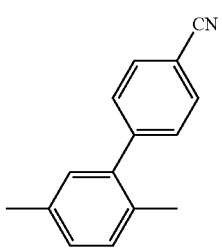
(a-27)
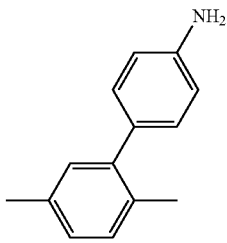
(a-28)
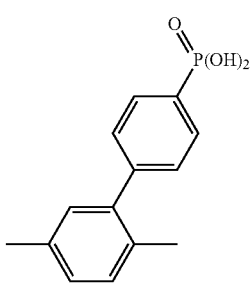
(a-29)
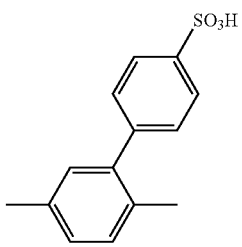
(a-30)
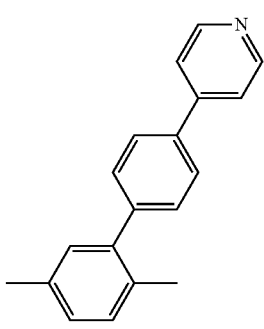

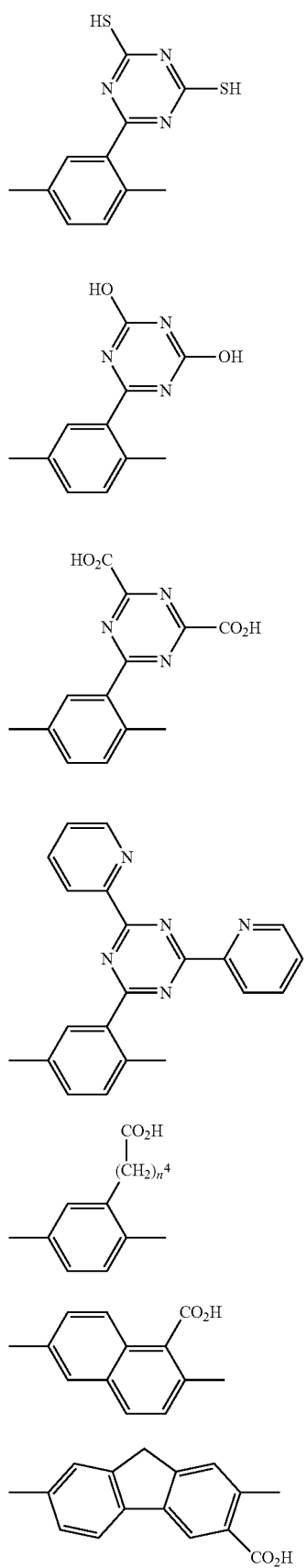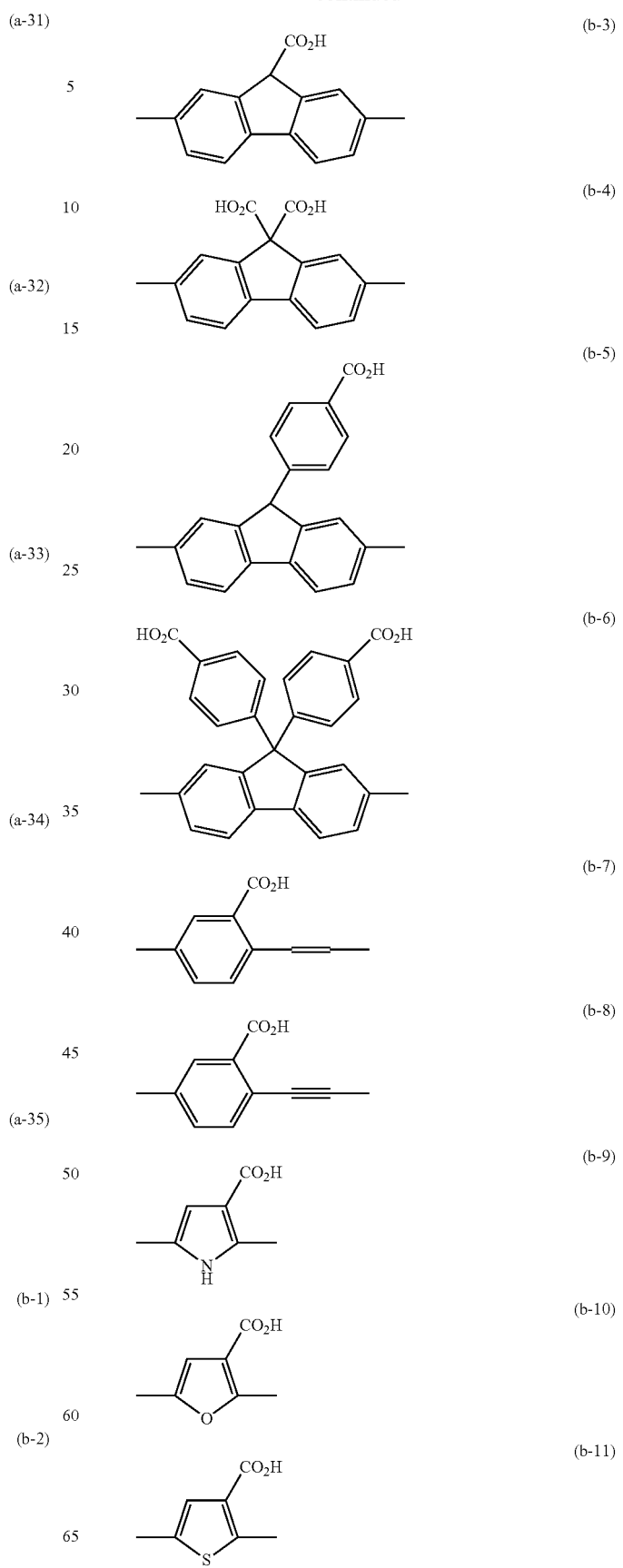

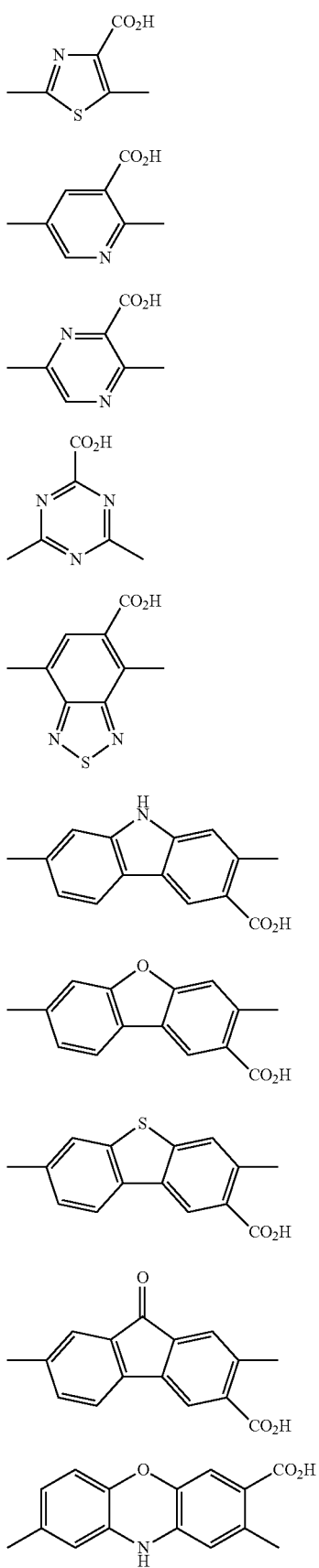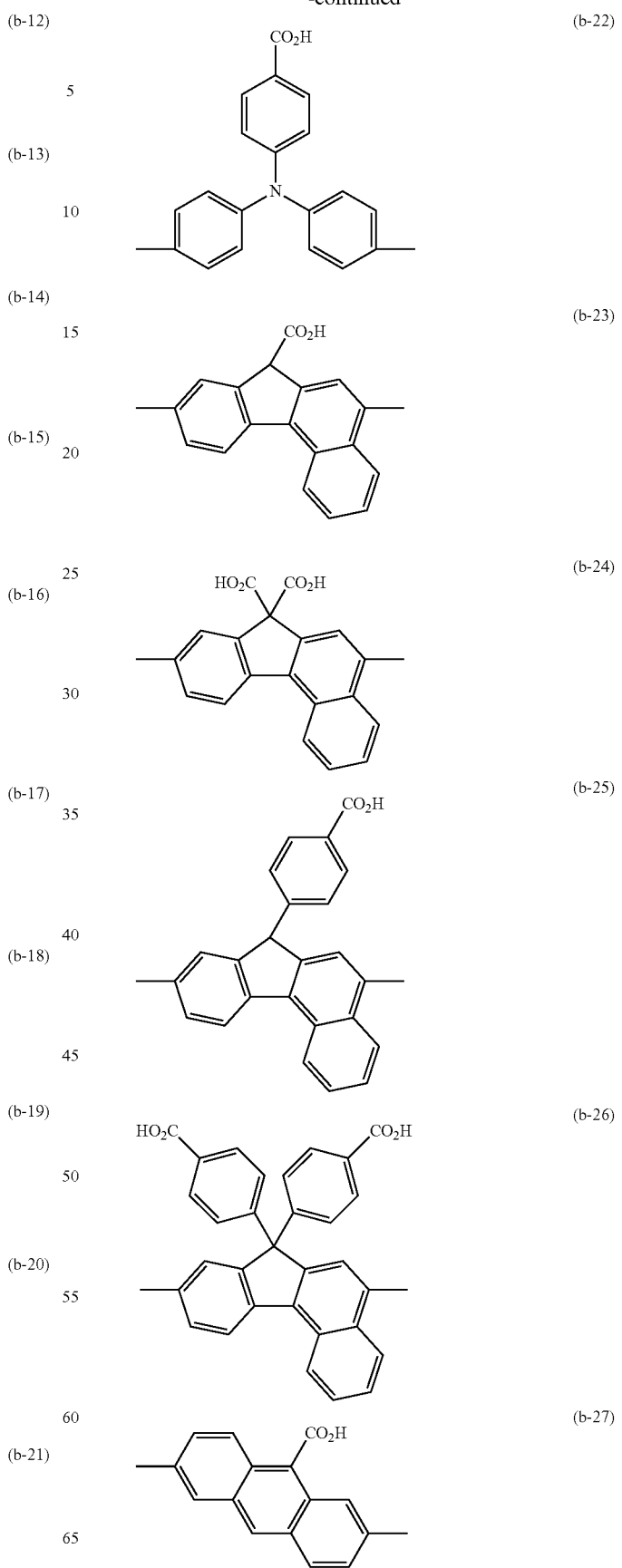

(b-28) 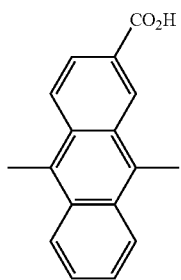
(b-29) 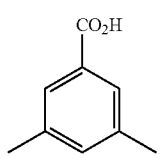
(b-30) 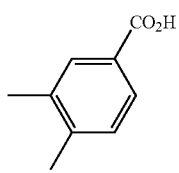
(b-31) 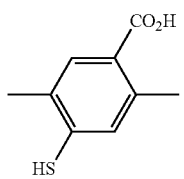
(b-32) 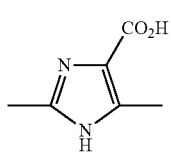
(b-33) 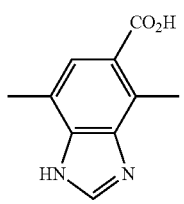
(b-34) 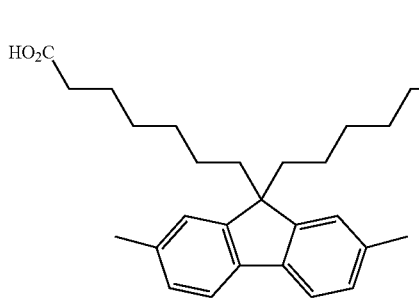
(b-35) 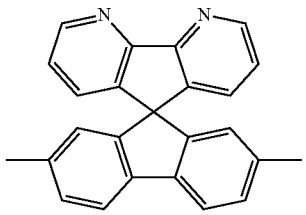
(b-36) 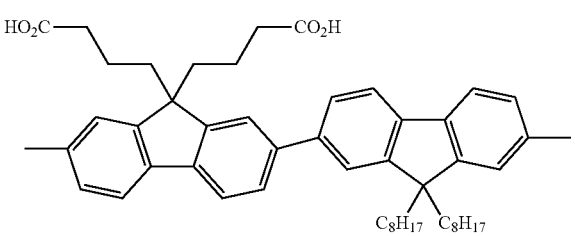
(b-37) 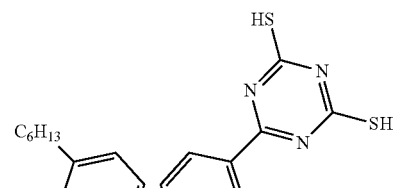
(b-38) 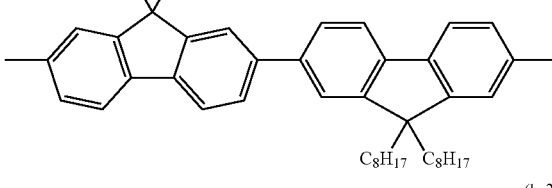
(b-39) 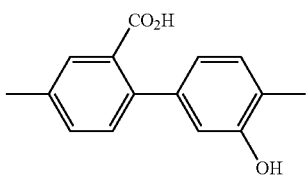
(c-1) 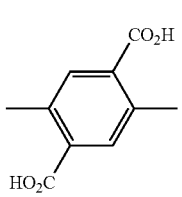
(c-2) 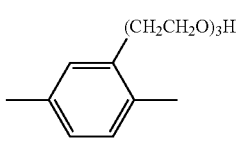

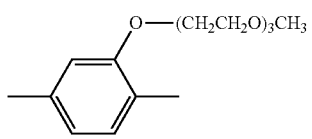 (c-3)
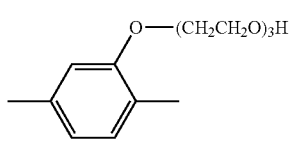 (c-4)
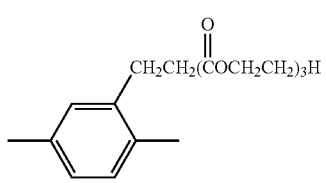 (c-5)
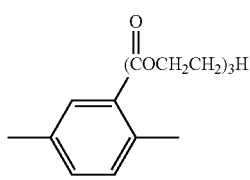 (c-6)
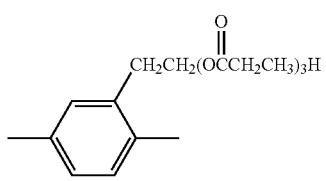 (c-7)
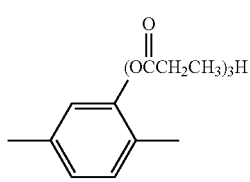 (c-8)
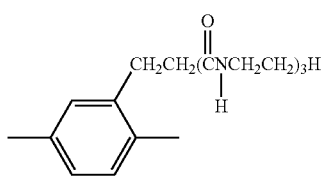 (c-9)
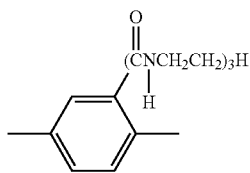 (c-10)
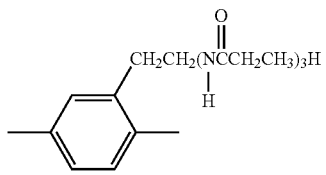 (c-11)
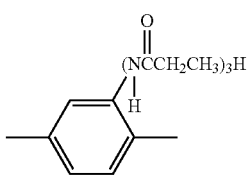 (c-12)
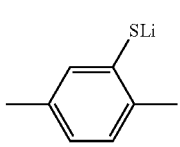 (c-13)
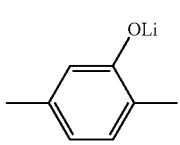 (c-14)
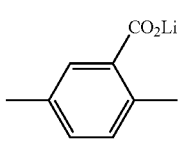 (c-15)
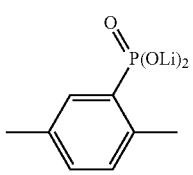 (c-16)
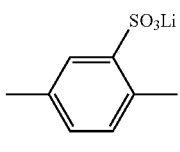 (c-17)
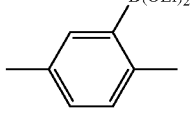 (c-18)
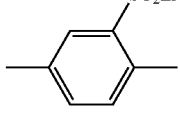 (c-19)
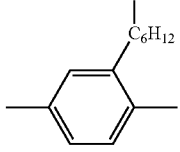 (c-20)
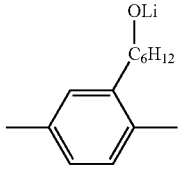 (c-21)

(c-22) 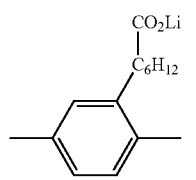
(c-23) 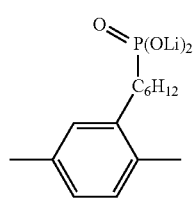
(c-24) 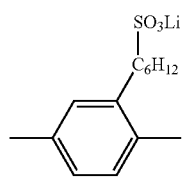
(c-25) 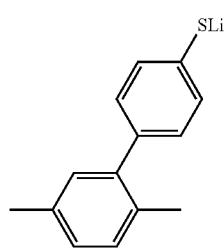
(c-26) 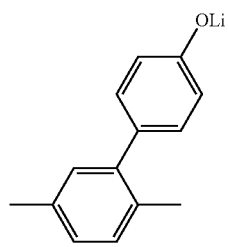
(c-27) 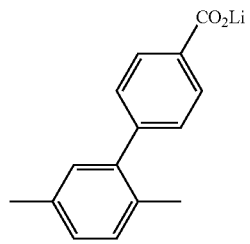
(c-28) 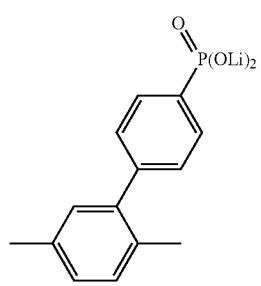
(c-29) 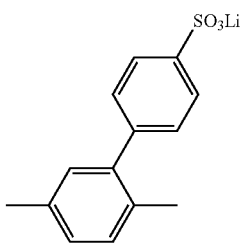
(c-30) 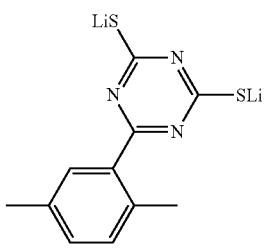
(c-31) 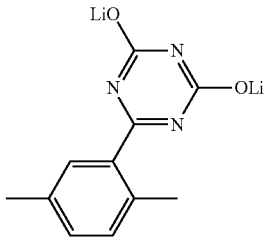
(c-32) 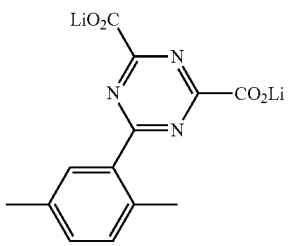
(c-33) 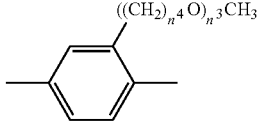
(c-34) 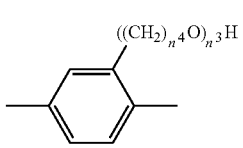
(c-35) 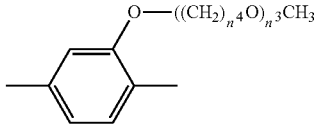
(c-36) 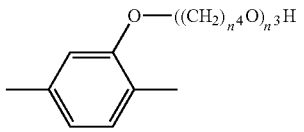

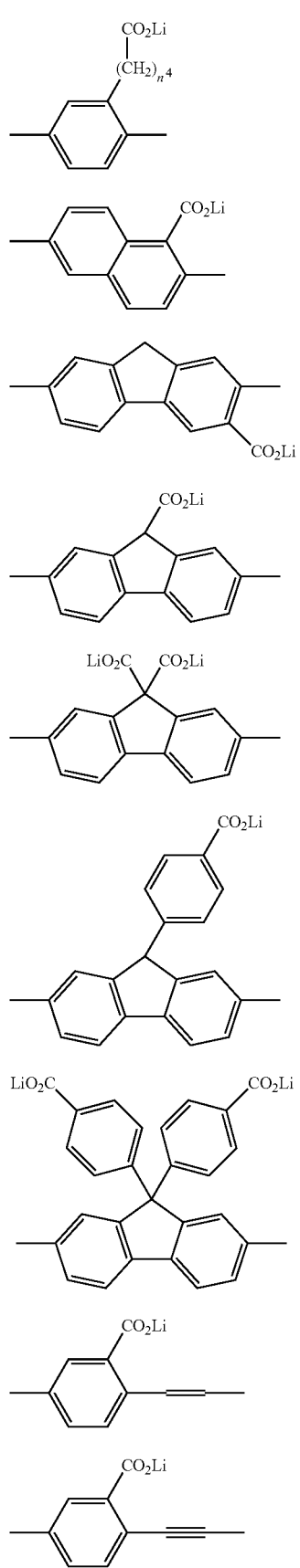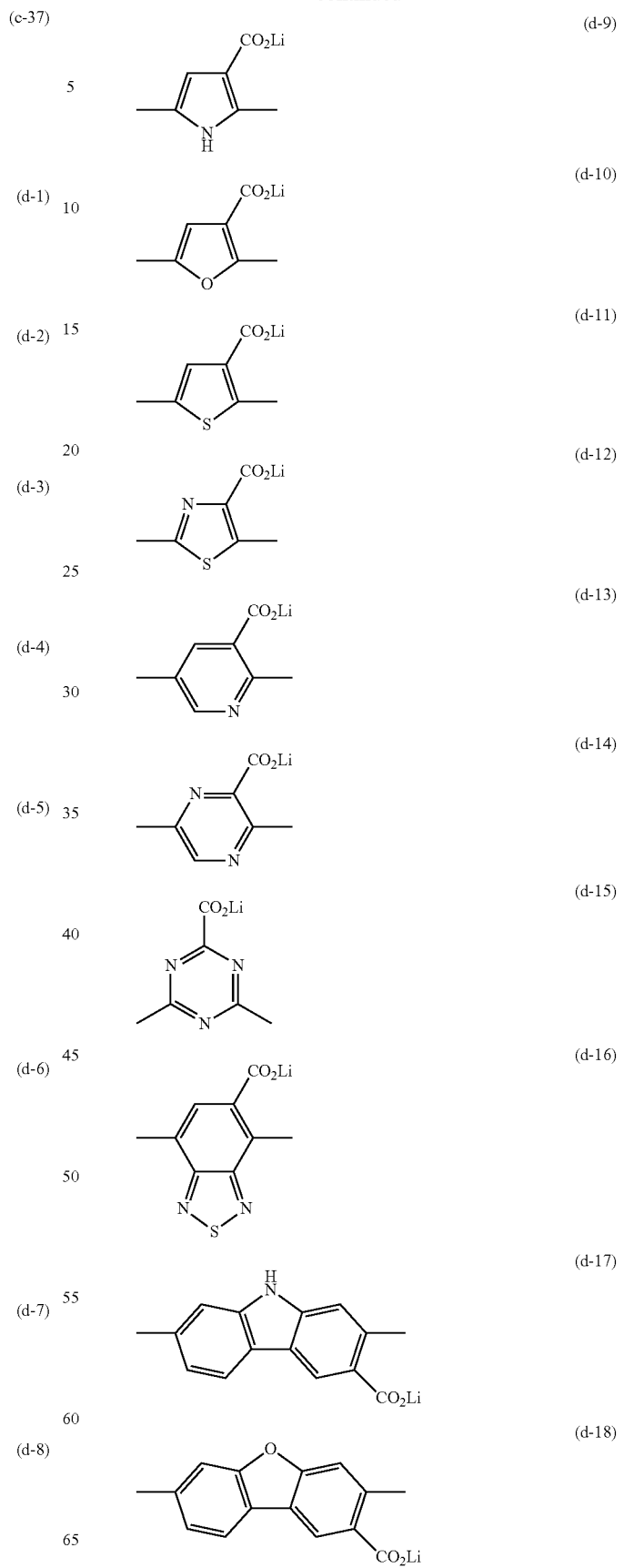

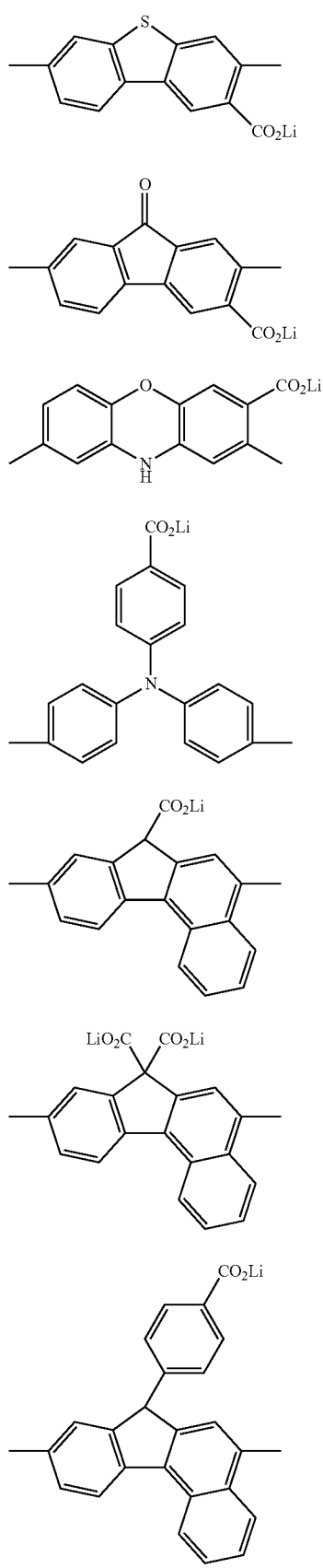
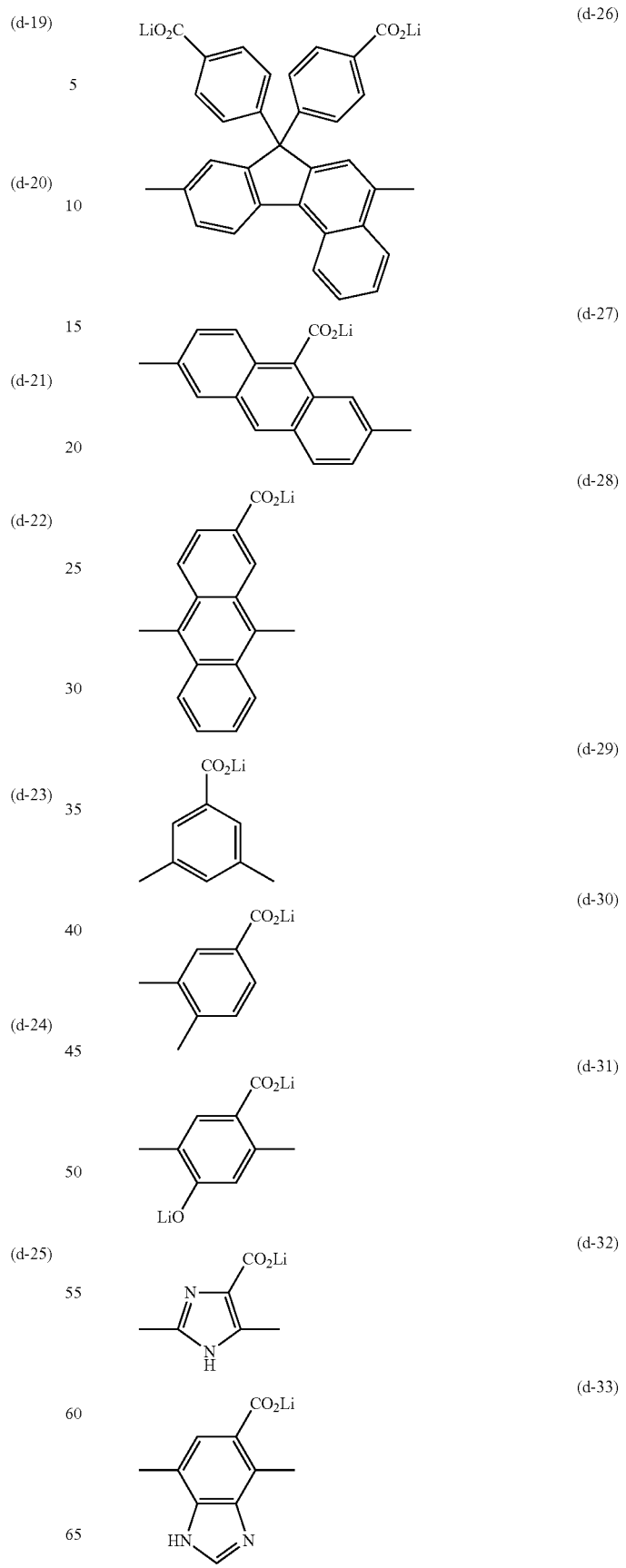

(d-34) 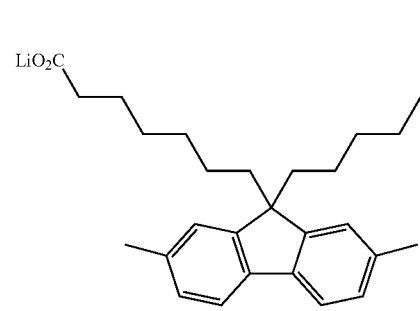
(d-35) 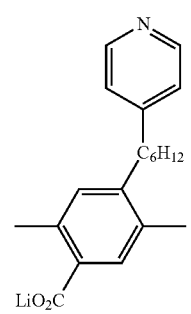
(d-36) 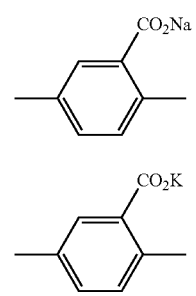
(d-37) 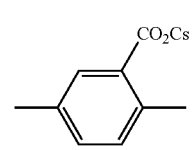
(d-38) 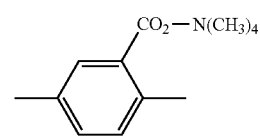
(d-39) 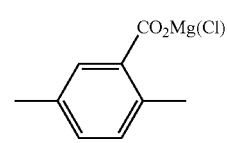
(d-40) 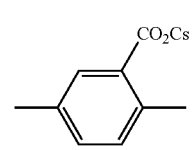
(d-41) 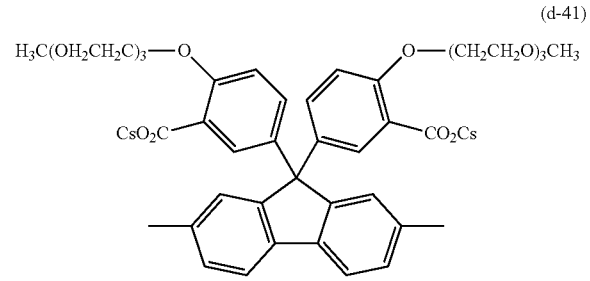
(d-42) 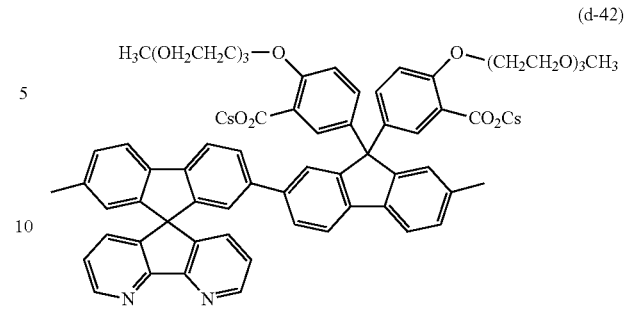
(d-43) 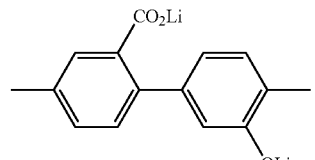
(d-44) 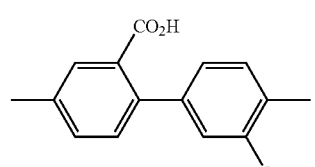
(d-45) 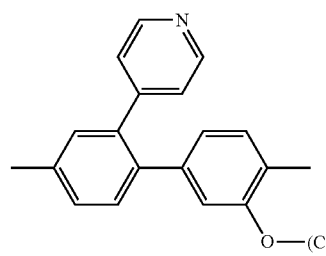
(d-46) 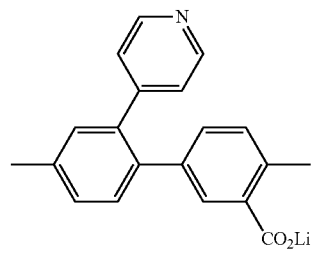
(d-47) 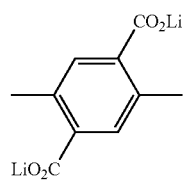
(e-1) 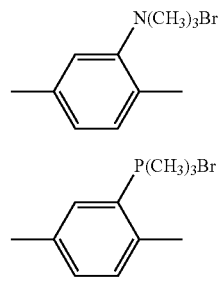
(e-2) 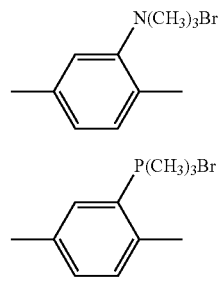

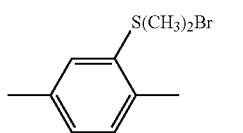 (e-3)
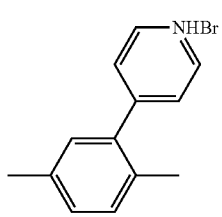 (e-4)
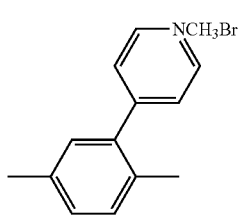 (e-5)
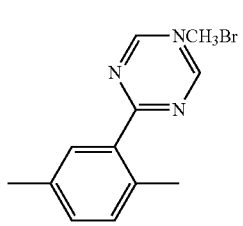 (e-6)
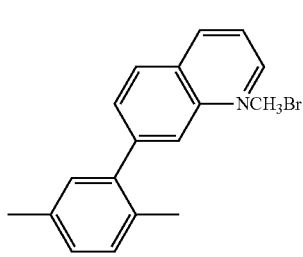 (e-7)
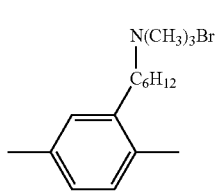 (e-8)
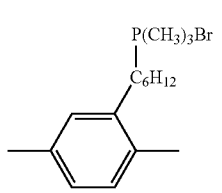 (e-9)
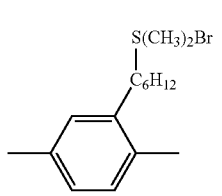 (e-10)
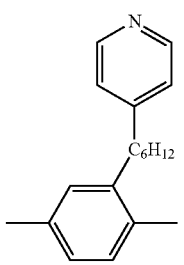 (e-11)
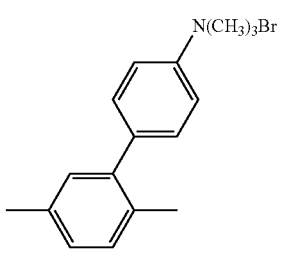 (e-12)
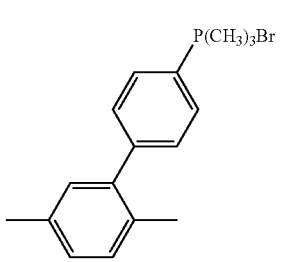 (e-13)
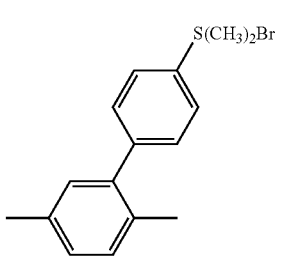 (e-14)
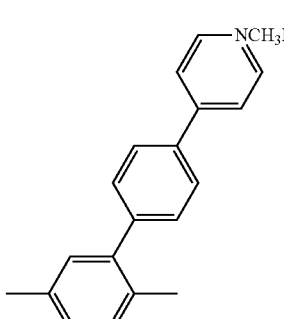 (e-15)
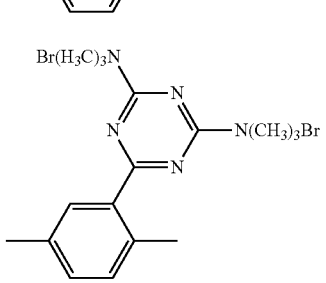 (e-16)

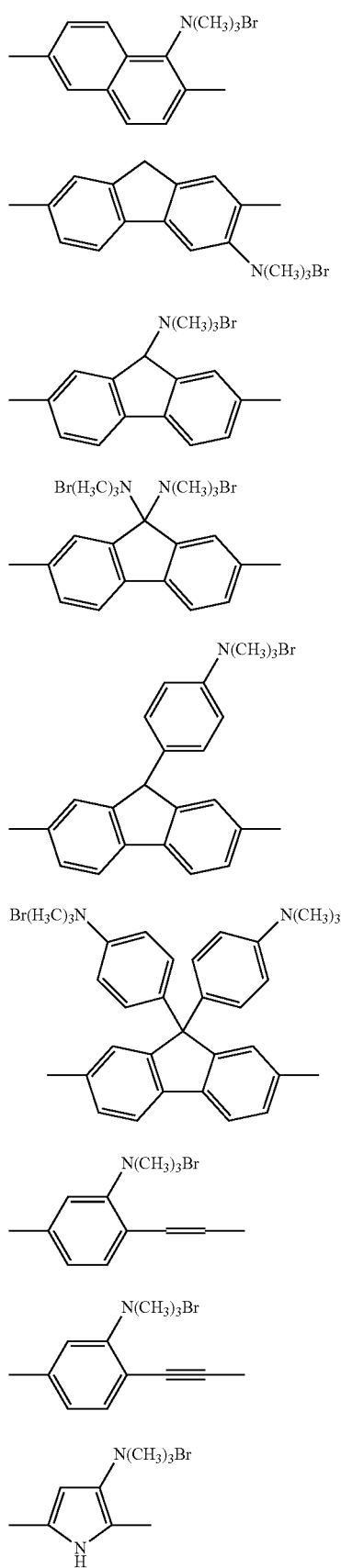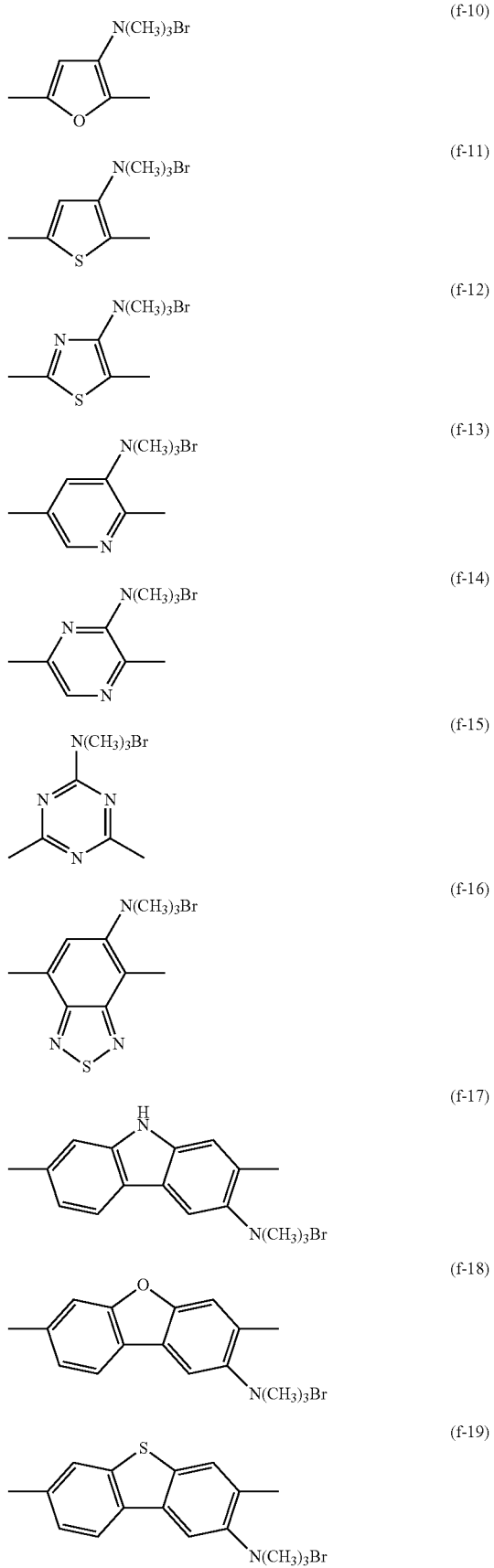

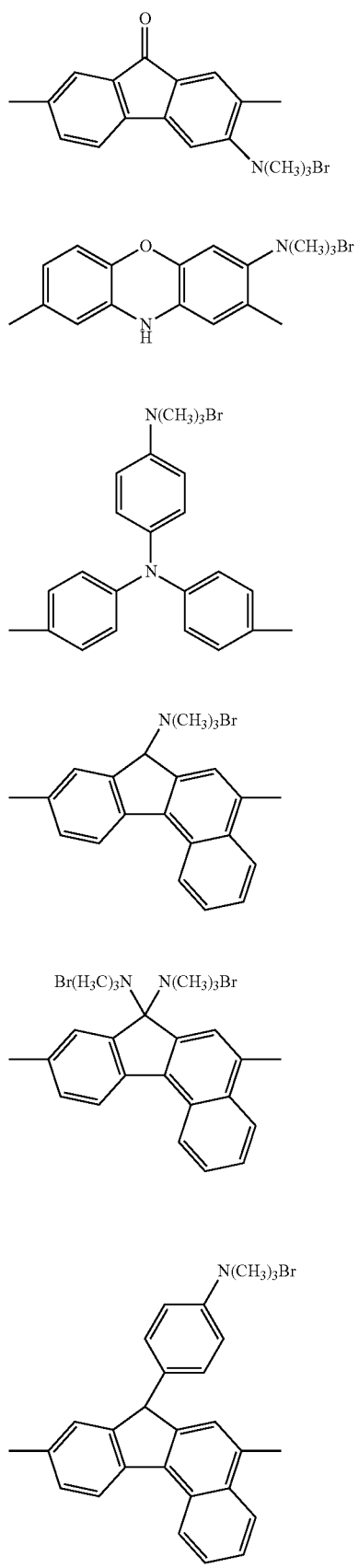
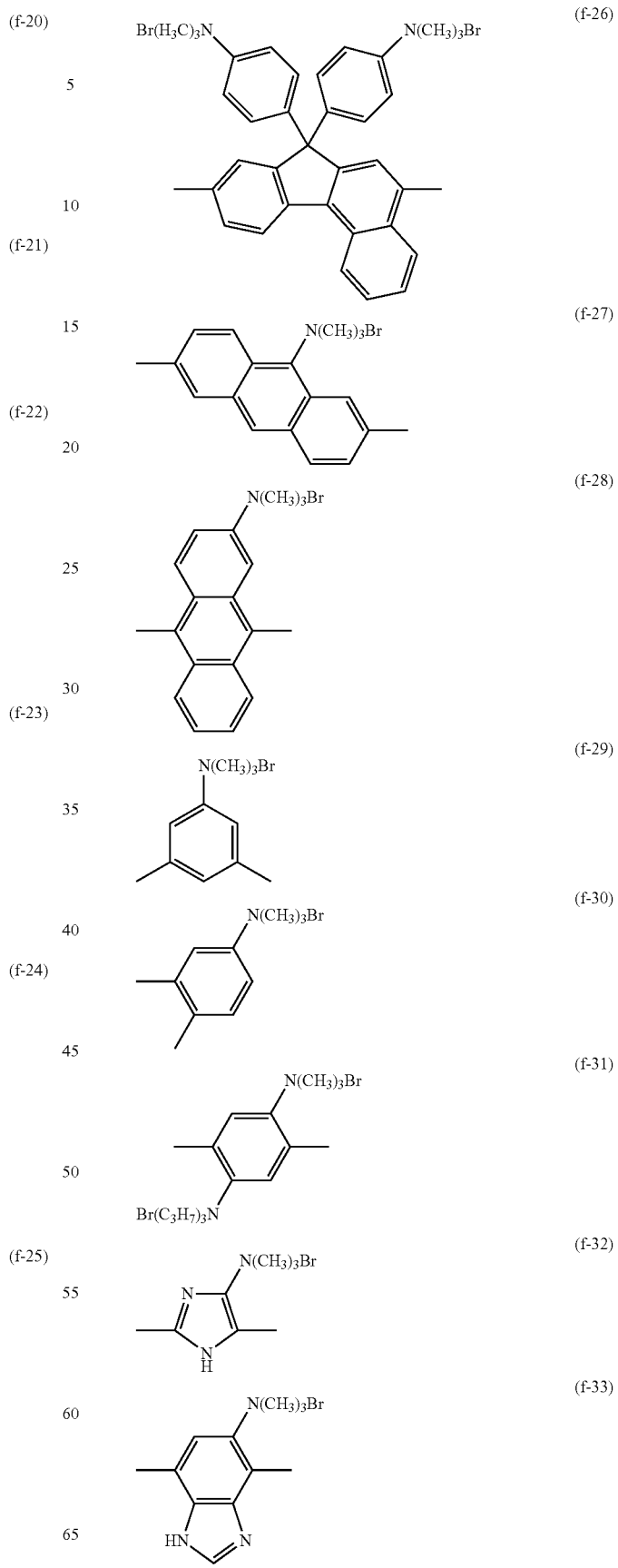

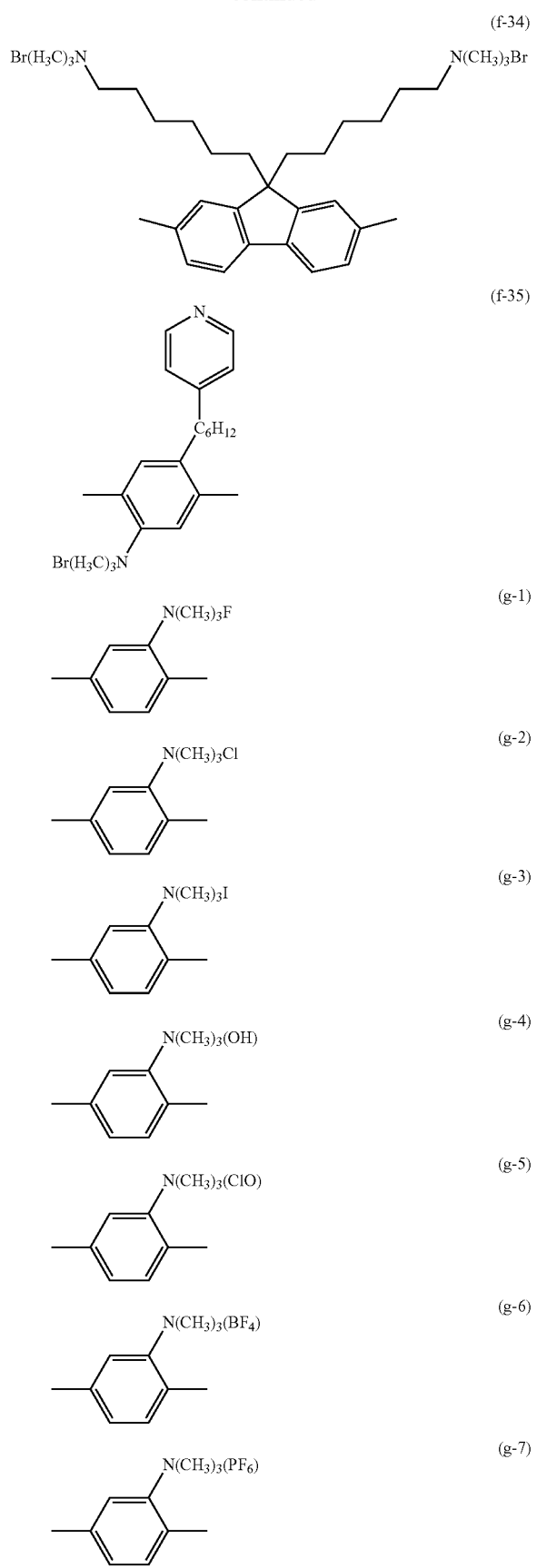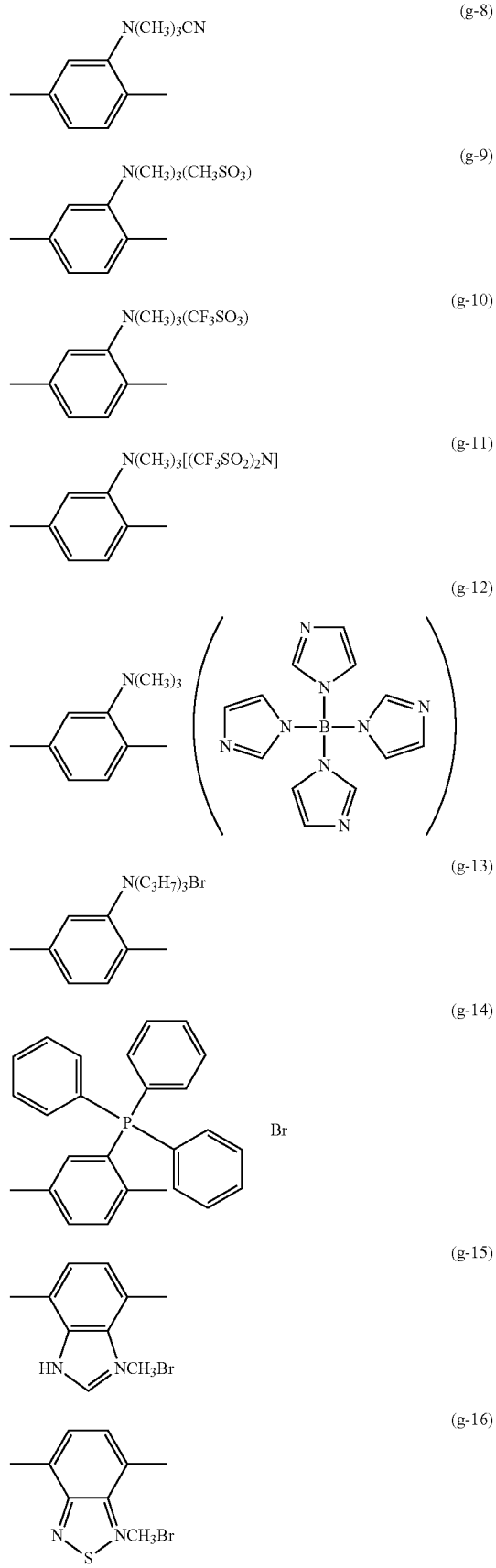

-continued

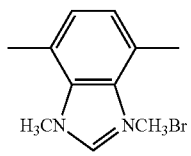 (g-17)

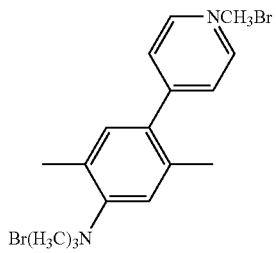 (g-18)

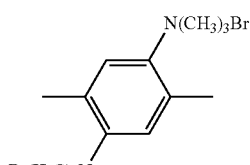 (g-19)

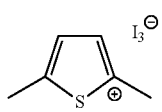 (g-20)

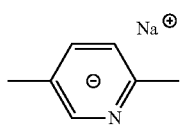 (g-21)

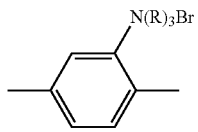 (g-22)

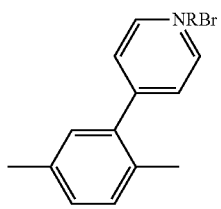 (g-23)

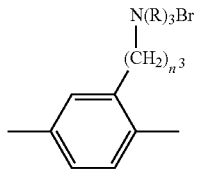 (g-24)

wherein $n^3$ represents an integer of 2 to 30, $n^4$ represents an integer of 1 to 10, and R represents a hydrogen atom or an optionally substituted hydrocarbyl group.

11. The metallic composite of claim 10, wherein the conjugated compound is a macromolecular compound having a repeating unit represented by the formula (b-6), (b-34), (b-37), (c-1), (c-2), (c-3), (c-4), (d-38), (d-41) or (d-42).

12. The metallic composite of claim 10, wherein the metallic nanosheet, the metallic nanorod, or the metallic nanowire is a metallic nanosheet, a metallic nanorod, or a metallic nanowire of a metal of Group 11 of the Periodic Table, respectively.

13. The metallic composite of claim 10, wherein the metallic nanosheet, the metallic nanorod, or the metallic nanowire is a silver nanosheet, a silver nanorod, or a silver nanowire, respectively.

14. The metallic composite of claim 11, wherein the metallic nanosheet, the metallic nanorod, or the metallic nanowire is a silver nanosheet, a silver nanorod, or a silver nanowire, respectively.

15. The metallic composite of claim 1, wherein a peak position measured by an X-ray photoelectron spectrometry for one or more atoms existing in the composite is detected at a peak position attributed to the conjugated compound as well as at a peak position of atoms existing in the metallic nanosheet, the metallic nanorod, or the metallic nanowire and a precursor of metallic nanosheet, metallic nanorod, or metallic nanowire, on a basis of a peak position of Ag3d.

16. The metallic composite of claim 1, wherein a highest occupied molecular orbital (HOMO) level of the conjugated compound is −4.5 eV or less, where the highest occupied molecular orbital is a value obtained by attaching "− (minus)" to a value of an ionization potential of the conjugated compound measured by a photoelectron spectrometer in the atmosphere.

17. The metallic composite of claim 1, wherein a lowest unoccupied molecular orbital (LUMO) level of the conjugated compound is −3.5 eV or more, where the lowest unoccupied molecular orbital is a value obtained from an ionization potential of the conjugated compound measured by a photoelectron spectrometer and a HOMO-LUMO gap measured by an ultraviolet-visible-near-infrared spectrophotometer.

18. A composition comprising the metallic composite of claim 1 and a conjugated compound having a molecular weight of 200 or more.

19. A cathode material comprising the metallic composite of claim 1.

20. A light-emitting device comprising a light-emitting layer between an anode and a cathode, in which the cathode is the metallic composite of claim 1.

21. A light-emitting device comprising a light-emitting layer between an anode and a cathode, in which the cathode is the composition of claim 18.

22. A photoelectric conversion device comprising a charge separation layer between an anode and a cathode, in which the cathode is the metallic composite of claim 1.

23. A photoelectric conversion device comprising a charge separation layer between an anode and a cathode, in which the cathode is the composition of claim 18.

24. A layered structure comprising a substrate and a layer produced with using the metallic composite of claim 1 formed on the substrate.

25. A method for manufacturing a transparent cathode, characterized by forming a transparent cathode by an application method with using a dispersion liquid of a conductive material having an aspect ratio of 10 or more and a largest diameter of 2000 nm or more.

* * * * *